US012800587B2

(12) United States Patent
Yang et al.

(10) Patent No.: US 12,800,587 B2
(45) Date of Patent: Nov. 17, 2026

(54) ARGININE FLUORESCENT PROBE, PREPARATION METHOD THEREFOR AND APPLICATION THEREOF

(71) Applicant: East China University of Science and Technology, Shanghai (CN)

(72) Inventors: Yi Yang, Shanghai (CN); Yuzheng Zhao, Shanghai (CN); Rui Li, Shanghai (CN); Yejun Zou, Shanghai (CN); Li Huang, Shanghai (CN); Xie Li, Shanghai (CN); Kun Jiang, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 985 days.

(21) Appl. No.: 17/904,498

(22) PCT Filed: Feb. 9, 2021

(86) PCT No.: PCT/CN2021/076314

§ 371 (c)(1),
(2) Date: Mar. 3, 2023

(87) PCT Pub. No.: WO2021/164665

PCT Pub. Date: Aug. 26, 2021

(65) Prior Publication Data

US 2023/0296616 A1 Sep. 21, 2023

(30) Foreign Application Priority Data

Feb. 18, 2020 (CN) ......................... 202010098995.5

(51) Int. Cl.
*G01N 33/68* (2006.01)
*C07K 14/00* (2006.01)
*G01N 33/533* (2006.01)

(52) U.S. Cl.
CPC ....... *G01N 33/6812* (2013.01); *C07K 14/001* (2013.01); *G01N 33/533* (2013.01)

(58) Field of Classification Search
CPC .................................................... G01N 33/533
See application file for complete search history.

(56) References Cited

U.S. PATENT DOCUMENTS

2015/0111222 A1* 4/2015 Marvin ................ C07K 14/195 435/254.11

OTHER PUBLICATIONS

Altschul et al., "Gapped BLAST and PSI-BLAST: A New Generation of Protein Database Search Programs," Nucleic Acids Research, 1997, vol. 25, No. 17, pp. 3389-3402.

Altschul et al., "Basic Local Alignment Search Tool," Journal of Molecular Biology, Oct. 1990, vol. 215, No. 3, pp. 403-410.

Chen et al., "arginine ABC transporter substrate-binding protein [*Salmonella enterica*]," GenBank: KUC12014.1, retrieved from NCBI.

Delforge et al., "The Regulation of Arginine Biosynthesis in *Saccharomyces cerevisiae*: The Specificity of argR-Mutations and the General Control of Amino-Acid Biosynthesis," European Journal of Biochemistry, Sep. 1975, vol. 57, No. 1 pp. 231-239.

Du et al., "Highly Selective Fluorescent Recognition of Histidine by a Crown Ether-Terpyridine-Zn(II) Sensor," Chemical Communications, 2013, vol. 49, No. 47, pp. 5399-5401.

Engeser et al., "A Fluorescent Molecular Thermometer Based on the Nickel(II) High-Spin/Low-Spin Interconversion," Chemical Communications, 1999, No. 13, pp. 1191-1192.

Fernandez-Murga et al., "Arginine Biosynthesis in Thermotoga maritima: Characterization of the Arginine-Sensitive N-Acetyl-L-Glutamate Kinase," Journal of Bacteriology, Sep. 2004, vol. 186, No. 18, pp. 6142-6149.

Fernandez-Murga et al., "Basis of Arginine Sensitivity of Microbial N-Acetyl-L-Glutamate Kinases: Mutagenesis and Protein Engineering Study with Pseudomonas aeruginosa and *Escherichia coli* Enzymes," Journal of Bacteriology, Apr. 2008, vol. 190 No. 8, pp. 3018-3025.

Hortala et al., "Designing the Selectivity of the Fluorescent Detection of Amino Acids: A Chemosensing Ensemble for Histidine," Journal of the American Chemical Society, Jan. 2003, vol. 125, No. 1, pp. 20-21.

Li et al., "Determination of Amino Acids in Panax notoginseng by Microwave Hydrolysis and Derivatization Coupled with Capillary Zone Electrophoresis Detection," Chemical Research in Chinese Universities, Jun. 2013, vol. 29, No. 3, pp. 434-438.

Mcclelland et al., "putative arginine-binding periplasmic protein [*Salmonella enterica* subsp. *enterica serovar Typhimurium* str. LT2]," Ncbi Reference Sequence: NP_463215.3, retrieved from NCBI.

Meng et al., "Moving Affinity Boundary Electrophoresis and its Selective Isolation of Histidine in Urine," Analyst, 2010, vol. 135, No. 7, pp. 1592-1599.

(Continued)

*Primary Examiner* — Suzanne M Noakes
(74) *Attorney, Agent, or Firm* — Greenberg Traurig, LLP; Melissa Hunter-Ensor; Nathan Hsu

(57) ABSTRACT

Provided is an arginine fluorescent probe, comprising a polypeptide B that responds to arginine and a fluorescent protein A that expresses arginine; the fluorescent protein A is inserted into the polypeptide B, B is divided into an upper structural part and a lower structural part, B1 and B2, and a probe structure represented by the formula B1-A-B2 is formed; optimized mutants are likewise obtained by truncation and site-directed mutagenesis at different positions, and specific binding of the polypeptide B and arginine leads to a change in the fluorescence signal of the fluorescent protein A; and the polypeptide B is an arginine binding protein or a mutant thereof. The arginine fluorescent probe provided by the present invention has a relatively small protein molecular weight, is easy to express, experiences large dynamic changes in fluorescence, has good specificity, can be expressed, by means of genetic manipulation, in different subcellular organelles of cells, and can be used for the high-throughput, quantitative detection of arginine inside and outside of cells.

17 Claims, 20 Drawing Sheets

Specification includes a Sequence Listing.

(56) References Cited

OTHER PUBLICATIONS

Nadler et al., "Rapid Construction of Metabolite Biosensors Using Domain-Insertion Profiling," Nature Communications, Jul. 2016, vol. 7, Article No. 12266, pp. 1-11.
Pu et al., "DNA/Ligand/Ion-Based Ensemble for Fluorescence Turn on Detection of Cysteine and Histidine with Tunable Dynamic Range," Analytical Chemistry, Oct. 2010, vol. 82, No. 19, pp. 8211-8216.
Stamp et al., "Crystallographic and microcalorimetric analyses reveal the structural basis for high arginine specificity in the *Salmonella enterica* serovar Typhimurium periplasmic binding protein STM4351," Proteins: Structure, Function, and Bioinformatics, 2011, vol. 79, No. 7, pp. 2352-2357.
Tateda et al., "Simultaneous Determination of Urocanic Acid Isomers and Histidine in Human Stratum Corneum by High-Performance Liquid Chromatography," Analytical Sciences, 2001, vol. 17, No. 6, pp. 775-778.
Wadud et al., "Method for Determination of Histidine in Tissues by Isocratic High-Performance Liquid Chromatography and its Application to the Measurement of Histidinol Dehydrogenase Activity in Six Cattle Organs," Journal of Chromatography B, 2002, vol. 767, pp. 369-374.
Weigel et al., "*Arabidopsis*: A Laboratory Manual," Genetics Research, Cambridge, 2002, vol. 80, p. 77, Book Review.
International Search Report and Written Opinion mailed May 11, 2021 in corresponding International PCT Patent Application No. PCT/CN2021/076314.

* cited by examiner

SEQUENCE LISTING

<160> NUMBER OF SEQ ID NOS: 42

<210> SEQ ID NO 1
<211> LENGTH: 229
<212> TYPE: PRT
<213> ORGANISM: Salmonella typhimurium

<400> SEQUENCE: 1

```
Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Tyr Glu Gly Leu Ser Ala Val
                85                  90                  95

Val Val Thr Arg Lys Gly Ala Tyr His Thr Phe Ala Asp Leu Lys Gly
            100                 105                 110

Lys Lys Val Gly Leu Glu Asn Gly Thr Thr His Gln Arg Tyr Leu Gln
        115                 120                 125

Asp Lys Gln Gln Ala Ile Thr Pro Val Ala Tyr Asp Ser Tyr Leu Asn
    130                 135                 140

Ala Phe Thr Asp Leu Lys Asn Asn Arg Leu Glu Gly Val Phe Gly Asp
145                 150                 155                 160

Val Ala Ala Ile Gly Lys Trp Leu Lys Asn Asn Pro Asp Tyr Ala Ile
                165                 170                 175

Met Asp Glu Arg Ala Ser Asp Pro Asp Tyr Tyr Gly Lys Gly Leu Gly
            180                 185                 190

Ile Ala Val Arg Lys Asp Asn Asp Ala Leu Leu Gln Glu Ile Asn Ala
        195                 200                 205

Ala Leu Asp Lys Val Lys Ala Ser Pro Glu Tyr Ala Gln Met Gln Glu
    210                 215                 220

Lys Trp Phe Thr Gln
225
```

<210> SEQ ID NO 2
<211> LENGTH: 246
<212> TYPE: PRT
<213> ORGANISM: Artificial Sequence
<220> FEATURE:
<223> OTHER INFORMATION: cpYFP

<400> SEQUENCE: 2

```
Tyr Asn Ser Asp Asn Val Tyr Ile Met Ala Asp Lys Gln Lys Asn Gly
1               5                   10                  15

Ile Lys Ala Asn Phe Lys Ile Arg His Asn Val Glu Asp Gly Ser Val
            20                  25                  30

Gln Leu Ala Asp His Tyr Gln Gln Asn Thr Pro Ile Gly Asp Gly Pro
        35                  40                  45

Val Leu Leu Pro Asp Asn His Tyr Leu Ser Phe Gln Ser Val Leu Ser
    50                  55                  60

Lys Asp Pro Asn Glu Lys Arg Asp His Met Val Leu Leu Glu Phe Val
65                  70                  75                  80
```

```
Thr Ala Ala Gly Ile Thr Leu Gly Met Asp Glu Leu Tyr Asn Val Asp
                85                  90                  95

Gly Gly Ser Gly Gly Thr Gly Ser Lys Gly Glu Glu Leu Phe Thr Gly
            100                 105                 110

Val Val Pro Ile Leu Val Glu Leu Asp Gly Asp Val Asn Gly His Lys
        115                 120                 125

Phe Ser Val Ser Gly Glu Gly Glu Gly Asp Ala Thr Tyr Gly Lys Leu
    130                 135                 140

Thr Leu Lys Leu Ile Cys Thr Thr Gly Lys Leu Pro Val Pro Trp Pro
145                 150                 155                 160

Thr Leu Val Thr Thr Leu Gly Tyr Gly Leu Lys Cys Phe Ala Arg Tyr
                165                 170                 175

Pro Asp His Met Lys Gln His Asp Phe Phe Lys Ser Ala Met Pro Glu
            180                 185                 190

Gly Tyr Val Gln Glu Arg Thr Ile Phe Phe Lys Asp Asp Gly Asn Tyr
        195                 200                 205

Lys Thr Arg Ala Glu Val Lys Phe Glu Gly Asp Thr Leu Val Asn Arg
    210                 215                 220

Ile Glu Leu Lys Gly Ile Asp Phe Lys Glu Asp Gly Asn Ile Leu Gly
225                 230                 235                 240

His Lys Leu Glu Tyr Asn
                245


<210> SEQ ID NO 3
<211> LENGTH: 241
<212> TYPE: PRT
<213> ORGANISM: Artificial Sequence
<220> FEATURE:
<223> OTHER INFORMATION: cpGFP

<400> SEQUENCE: 3

Asn Val Tyr Ile Lys Ala Asp Lys Gln Lys Asn Gly Ile Lys Ala Asn
1               5                   10                  15

Phe Lys Ile Arg His Asn Ile Glu Asp Gly Gly Val Gln Leu Ala Tyr
            20                  25                  30

His Tyr Gln Gln Asn Thr Pro Ile Gly Asp Gly Pro Val Leu Leu Pro
        35                  40                  45

Asp Asn His Tyr Leu Ser Val Gln Ser Ile Leu Ser Lys Asp Pro Asn
    50                  55                  60

Glu Lys Arg Asp His Met Val Leu Leu Glu Phe Val Thr Ala Ala Gly
65                  70                  75                  80

Ile Thr Leu Gly Met Asp Glu Leu Tyr Lys Gly Gly Thr Gly Gly Ser
                85                  90                  95

Met Val Ser Lys Gly Glu Glu Leu Phe Thr Gly Val Val Pro Ile Gln
            100                 105                 110

Val Glu Leu Asp Gly Asp Val Asn Gly His Lys Phe Ser Val Ser Gly
        115                 120                 125

Glu Gly Glu Gly Asp Ala Thr Tyr Gly Lys Leu Thr Leu Lys Phe Ile
    130                 135                 140

Cys Thr Thr Gly Lys Leu Pro Val Pro Trp Pro Thr Leu Val Thr Thr
145                 150                 155                 160

Leu Thr Tyr Gly Val Gln Cys Phe Ser Arg Tyr Pro Asp His Met Lys
                165                 170                 175

Gln His Asp Phe Phe Lys Ser Ala Met Pro Glu Gly Tyr Ile Gln Glu
            180                 185                 190
```

```
Arg Thr Ile Phe Phe Lys Asp Asp Gly Asn Tyr Lys Thr Arg Ala Glu
        195                 200                 205

Val Lys Phe Glu Gly Asp Thr Leu Val Asn Arg Ile Glu Leu Lys Gly
    210                 215                 220

Ile Asp Phe Lys Glu Asp Gly Asn Ile Leu Gly His Lys Leu Glu Tyr
225                 230                 235                 240

Asn


<210> SEQ ID NO 4
<211> LENGTH: 243
<212> TYPE: PRT
<213> ORGANISM: Artificial Sequence
<220> FEATURE:
<223> OTHER INFORMATION: cpBFP

<400> SEQUENCE: 4

Asn Val Tyr Ile Lys Ala Asp Lys Gln Lys Asn Gly Ile Lys Ala Asn
1               5                   10                  15

Phe Lys Ile Arg His Asn Ile Glu Gly Gly Gly Val Gln Leu Ala Tyr
            20                  25                  30

His Tyr Gln Gln Asn Thr Pro Ile Gly Asp Gly Pro Val Leu Leu Pro
        35                  40                  45

Asp Asn His Tyr Leu Ser Val Gln Ser Ile Leu Ser Lys Asp Pro Asn
    50                  55                  60

Glu Lys Arg Asp His Met Val Leu Leu Glu Phe Val Thr Ala Ala Gly
65                  70                  75                  80

Ile Thr Leu Gly Met Asp Glu Leu Tyr Lys Gly Gly Thr Gly Gly Ser
                85                  90                  95

Glu Ser Met Val Ser Lys Gly Glu Glu Leu Phe Thr Gly Val Val Pro
            100                 105                 110

Ile Gln Val Glu Leu Asp Gly Asp Val Asn Gly His Lys Phe Ser Val
        115                 120                 125

Ser Gly Glu Gly Glu Gly Asp Ala Thr Tyr Gly Lys Leu Thr Leu Lys
    130                 135                 140

Phe Ile Cys Thr Thr Gly Lys Leu Pro Val Pro Trp Pro Thr Leu Val
145                 150                 155                 160

Thr Thr Leu Ser His Gly Val Gln Cys Phe Ser Arg Tyr Pro Asp His
                165                 170                 175

Met Lys Gln His Asp Phe Phe Lys Ser Ala Met Pro Gly Gly Tyr Ile
            180                 185                 190

Gln Glu Arg Thr Ile Phe Phe Lys Asp Asp Gly Asn Tyr Lys Thr Arg
        195                 200                 205

Ala Glu Val Lys Phe Glu Gly Asp Thr Leu Val Asn Arg Ile Glu Leu
    210                 215                 220

Lys Gly Ile Asp Phe Lys Glu Asp Gly Asn Ile Leu Gly His Lys Leu
225                 230                 235                 240

Glu Tyr Asn


<210> SEQ ID NO 5
<211> LENGTH: 242
<212> TYPE: PRT
<213> ORGANISM: Artificial Sequence
<220> FEATURE:
<223> OTHER INFORMATION: cpmApple
```

<400> SEQUENCE: 5

```
Val Ser Glu Arg Met Tyr Pro Glu Asp Gly Ala Leu Lys Ser Glu Ile
1               5                   10                  15

Lys Lys Gly Leu Arg Leu Lys Asp Gly Gly His Tyr Ala Ala Glu Val
            20                  25                  30

Lys Thr Thr Tyr Lys Ala Lys Lys Pro Val Gln Leu Pro Gly Ala Tyr
        35                  40                  45

Ile Val Asp Ile Lys Leu Asp Ile Val Ser His Asn Glu Asp Tyr Thr
    50                  55                  60

Ile Val Glu Gln Cys Glu Arg Ala Glu Gly Arg His Ser Thr Gly Gly
65                  70                  75                  80

Met Asp Glu Leu Tyr Lys Gly Gly Thr Gly Gly Ser Leu Val Ser Lys
                85                  90                  95

Gly Glu Glu Asp Asn Met Ala Ile Ile Lys Glu Phe Met Arg Phe Lys
            100                 105                 110

Val His Met Glu Gly Ser Val Asn Gly His Glu Phe Glu Ile Glu Gly
        115                 120                 125

Glu Gly Glu Gly Arg Pro Tyr Glu Ala Phe Gln Thr Ala Lys Leu Lys
    130                 135                 140

Val Thr Lys Gly Gly Pro Leu Pro Phe Ala Trp Asp Ile Leu Ser Pro
145                 150                 155                 160

Gln Phe Met Tyr Gly Ser Lys Ala Tyr Ile Lys His Pro Ala Asp Ile
                165                 170                 175

Pro Asp Tyr Phe Lys Leu Ser Phe Pro Glu Gly Phe Arg Trp Glu Arg
            180                 185                 190

Val Met Asn Phe Glu Asp Gly Gly Ile Ile His Val Asn Gln Asp Ser
        195                 200                 205

Ser Leu Gln Asp Gly Val Phe Ile Tyr Lys Val Lys Leu Arg Gly Thr
    210                 215                 220

Asn Phe Pro Pro Asp Gly Pro Val Met Gln Lys Lys Thr Met Gly Trp
225                 230                 235                 240

Glu Ala
```

<210> SEQ ID NO 6
<211> LENGTH: 471
<212> TYPE: PRT
<213> ORGANISM: Artificial Sequence
<220> FEATURE:
<223> OTHER INFORMATION: sensor

<400> SEQUENCE: 6

```
Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Tyr Asn Ser Asp Asn Val Tyr Ile Met
                85                  90                  95
```

```
Ala Asp Lys Gln Lys Asn Gly Ile Lys Ala Asn Phe Lys Ile Arg His
            100                 105                 110

Asn Val Glu Asp Gly Ser Val Gln Leu Ala Asp His Tyr Gln Gln Asn
        115                 120                 125

Thr Pro Ile Gly Asp Gly Pro Val Leu Leu Pro Asp Asn His Tyr Leu
    130                 135                 140

Ser Phe Gln Ser Val Leu Ser Lys Asp Pro Asn Glu Lys Arg Asp His
145                 150                 155                 160

Met Val Leu Leu Glu Phe Val Thr Ala Ala Gly Ile Thr Leu Gly Met
                165                 170                 175

Asp Glu Leu Tyr Asn Val Asp Gly Gly Ser Gly Gly Thr Gly Ser Lys
            180                 185                 190

Gly Glu Glu Leu Phe Thr Gly Val Val Pro Ile Leu Val Glu Leu Asp
        195                 200                 205

Gly Asp Val Asn Gly His Lys Phe Ser Val Ser Gly Glu Gly Glu Gly
    210                 215                 220

Asp Ala Thr Tyr Gly Lys Leu Thr Leu Lys Leu Ile Cys Thr Thr Gly
225                 230                 235                 240

Lys Leu Pro Val Pro Trp Pro Thr Leu Val Thr Thr Leu Gly Tyr Gly
                245                 250                 255

Leu Lys Cys Phe Ala Arg Tyr Pro Asp His Met Lys Gln His Asp Phe
            260                 265                 270

Phe Lys Ser Ala Met Pro Glu Gly Tyr Val Gln Glu Arg Thr Ile Phe
        275                 280                 285

Phe Lys Asp Asp Gly Asn Tyr Lys Thr Arg Ala Glu Val Lys Phe Glu
    290                 295                 300

Gly Asp Thr Leu Val Asn Arg Ile Glu Leu Lys Gly Ile Gly Phe Lys
305                 310                 315                 320

Glu Asp Gly Asn Ile Leu Gly His Lys Leu Glu Tyr Asn Gly Leu Ser
                325                 330                 335

Ala Val Val Val Thr Arg Lys Gly Ala Tyr His Thr Phe Ala Asp Leu
            340                 345                 350

Lys Gly Lys Lys Val Gly Leu Glu Asn Gly Thr Thr His Gln Arg Tyr
        355                 360                 365

Leu Gln Asp Lys Gln Gln Ala Ile Thr Pro Val Ala Tyr Asp Ser Tyr
    370                 375                 380

Leu Asn Ala Phe Thr Asp Leu Lys Asn Asn Arg Leu Glu Gly Val Phe
385                 390                 395                 400

Gly Asp Val Ala Ala Ile Gly Lys Trp Leu Lys Asn Asn Pro Asp Tyr
                405                 410                 415

Ala Ile Met Asp Glu Arg Ala Ser Asp Pro Asp Tyr Tyr Gly Lys Gly
            420                 425                 430

Leu Gly Ile Ala Val Arg Lys Asp Asn Asp Ala Leu Leu Gln Glu Ile
        435                 440                 445

Asn Ala Ala Leu Asp Lys Val Lys Ala Ser Pro Glu Tyr Ala Gln Met
    450                 455                 460

Gln Glu Lys Trp Phe Thr Gln
465                 470
```

<210> SEQ ID NO 7
<211> LENGTH: 470
<212> TYPE: PRT
<213> ORGANISM: Artificial Sequence
<220> FEATURE:

<223> OTHER INFORMATION: sensor

<400> SEQUENCE: 7

```
Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Tyr Asn Ser Asp Asn Val Tyr Ile Met
                85                  90                  95

Ala Asp Lys Gln Lys Asn Gly Ile Lys Ala Asn Phe Lys Ile Arg His
            100                 105                 110

Asn Val Glu Asp Gly Ser Val Gln Leu Ala Asp His Tyr Gln Gln Asn
        115                 120                 125

Thr Pro Ile Gly Asp Gly Pro Val Leu Leu Pro Asp Asn His Tyr Leu
    130                 135                 140

Ser Phe Gln Ser Val Leu Ser Lys Asp Pro Asn Glu Lys Arg Asp His
145                 150                 155                 160

Met Val Leu Leu Glu Phe Val Thr Ala Ala Gly Ile Thr Leu Gly Met
                165                 170                 175

Asp Glu Leu Tyr Asn Val Asp Gly Gly Ser Gly Gly Thr Gly Ser Lys
            180                 185                 190

Gly Glu Glu Leu Phe Thr Gly Val Val Pro Ile Leu Val Glu Leu Asp
        195                 200                 205

Gly Asp Val Asn Gly His Lys Phe Ser Val Ser Gly Glu Gly Glu Gly
    210                 215                 220

Asp Ala Thr Tyr Gly Lys Leu Thr Leu Lys Leu Ile Cys Thr Thr Gly
225                 230                 235                 240

Lys Leu Pro Val Pro Trp Pro Thr Leu Val Thr Thr Leu Gly Tyr Gly
                245                 250                 255

Leu Lys Cys Phe Ala Arg Tyr Pro Asp His Met Lys Gln His Asp Phe
            260                 265                 270

Phe Lys Ser Ala Met Pro Glu Gly Tyr Val Gln Glu Arg Thr Ile Phe
        275                 280                 285

Phe Lys Asp Asp Gly Asn Tyr Lys Thr Arg Ala Glu Val Lys Phe Glu
    290                 295                 300

Gly Asp Thr Leu Val Asn Arg Ile Glu Leu Lys Gly Ile Gly Phe Lys
305                 310                 315                 320

Glu Asp Gly Asn Ile Leu Gly His Lys Leu Glu Tyr Asn Leu Ser Ala
                325                 330                 335

Val Val Val Thr Arg Lys Gly Ala Tyr His Thr Phe Ala Asp Leu Lys
            340                 345                 350

Gly Lys Lys Val Gly Leu Glu Asn Gly Thr Thr His Gln Arg Tyr Leu
        355                 360                 365

Gln Asp Lys Gln Gln Ala Ile Thr Pro Val Ala Tyr Asp Ser Tyr Leu
    370                 375                 380

Asn Ala Phe Thr Asp Leu Lys Asn Asn Arg Leu Glu Gly Val Phe Gly
385                 390                 395                 400
```

-continued

Asp Val Ala Ala Ile Gly Lys Trp Leu Lys Asn Asn Pro Asp Tyr Ala
405 410 415

Ile Met Asp Glu Arg Ala Ser Asp Pro Asp Tyr Tyr Gly Lys Gly Leu
420 425 430

Gly Ile Ala Val Arg Lys Asp Asn Asp Ala Leu Leu Gln Glu Ile Asn
435 440 445

Ala Ala Leu Asp Lys Val Lys Ala Ser Pro Glu Tyr Ala Gln Met Gln
450 455 460

Glu Lys Trp Phe Thr Gln
465 470

<210> SEQ ID NO 8
<211> LENGTH: 469
<212> TYPE: PRT
<213> ORGANISM: Artificial Sequence
<220> FEATURE:
<223> OTHER INFORMATION: sensor

<400> SEQUENCE: 8

Ala Ser Val Ser Ala Arg Thr Leu His Phe Gly Thr Ser Ala Thr Tyr
1 5 10 15

Ala Pro Tyr Glu Phe Val Asp Ala Asp Asn Lys Ile Val Gly Phe Asp
20 25 30

Ile Asp Val Ala Asn Ala Val Cys Lys Glu Met Gln Ala Glu Cys Ser
35 40 45

Phe Thr Asn Gln Ser Phe Asp Ser Leu Ile Pro Ser Leu Arg Phe Lys
50 55 60

Lys Phe Asp Ala Val Ile Ala Gly Met Asp Met Thr Pro Lys Arg Glu
65 70 75 80

Gln Gln Val Ser Phe Ser Gln Tyr Asn Ser Asp Asn Val Tyr Ile Met
85 90 95

Ala Asp Lys Gln Lys Asn Gly Ile Lys Ala Asn Phe Lys Ile Arg His
100 105 110

Asn Val Glu Asp Gly Ser Val Gln Leu Ala Asp His Tyr Gln Gln Asn
115 120 125

Thr Pro Ile Gly Asp Gly Pro Val Leu Leu Pro Asp Asn His Tyr Leu
130 135 140

Ser Phe Gln Ser Val Leu Ser Lys Asp Pro Asn Glu Lys Arg Asp His
145 150 155 160

Met Val Leu Leu Glu Phe Val Thr Ala Ala Gly Ile Thr Leu Gly Met
165 170 175

Asp Glu Leu Tyr Asn Val Asp Gly Gly Ser Gly Gly Thr Gly Ser Lys
180 185 190

Gly Glu Glu Leu Phe Thr Gly Val Val Pro Ile Leu Val Glu Leu Asp
195 200 205

Gly Asp Val Asn Gly His Lys Phe Ser Val Ser Gly Glu Gly Glu Gly
210 215 220

Asp Ala Thr Tyr Gly Lys Leu Thr Leu Lys Leu Ile Cys Thr Thr Gly
225 230 235 240

Lys Leu Pro Val Pro Trp Pro Thr Leu Val Thr Thr Leu Gly Tyr Gly
245 250 255

Leu Lys Cys Phe Ala Arg Tyr Pro Asp His Met Lys Gln His Asp Phe
260 265 270

Phe Lys Ser Ala Met Pro Glu Gly Tyr Val Gln Glu Arg Thr Ile Phe
275 280 285

```
Phe Lys Asp Asp Gly Asn Tyr Lys Thr Arg Ala Glu Val Lys Phe Glu
    290                 295                 300

Gly Asp Thr Leu Val Asn Arg Ile Glu Leu Lys Gly Ile Gly Phe Lys
305                 310                 315                 320

Glu Asp Gly Asn Ile Leu Gly His Lys Leu Glu Tyr Asn Ser Ala Val
                325                 330                 335

Val Val Thr Arg Lys Gly Ala Tyr His Thr Phe Ala Asp Leu Lys Gly
            340                 345                 350

Lys Lys Val Gly Leu Glu Asn Gly Thr Thr His Gln Arg Tyr Leu Gln
        355                 360                 365

Asp Lys Gln Gln Ala Ile Thr Pro Val Ala Tyr Asp Ser Tyr Leu Asn
    370                 375                 380

Ala Phe Thr Asp Leu Lys Asn Asn Arg Leu Glu Gly Val Phe Gly Asp
385                 390                 395                 400

Val Ala Ala Ile Gly Lys Trp Leu Lys Asn Asn Pro Asp Tyr Ala Ile
                405                 410                 415

Met Asp Glu Arg Ala Ser Asp Pro Asp Tyr Tyr Gly Lys Gly Leu Gly
            420                 425                 430

Ile Ala Val Arg Lys Asp Asn Asp Ala Leu Leu Gln Glu Ile Asn Ala
        435                 440                 445

Ala Leu Asp Lys Val Lys Ala Ser Pro Glu Tyr Ala Gln Met Gln Glu
    450                 455                 460

Lys Trp Phe Thr Gln
465


<210> SEQ ID NO 9
<211> LENGTH: 475
<212> TYPE: PRT
<213> ORGANISM: Artificial Sequence
<220> FEATURE:
<223> OTHER INFORMATION: sensor

<400> SEQUENCE: 9

Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Asn Ser Asp Asn Val Tyr Ile
                85                  90                  95

Met Ala Asp Lys Gln Lys Asn Gly Ile Lys Ala Asn Phe Lys Ile Arg
            100                 105                 110

His Asn Val Glu Asp Gly Ser Val Gln Leu Ala Asp His Tyr Gln Gln
        115                 120                 125

Asn Thr Pro Ile Gly Asp Gly Pro Val Leu Leu Pro Asp Asn His Tyr
    130                 135                 140

Leu Ser Phe Gln Ser Val Leu Ser Lys Asp Pro Asn Glu Lys Arg Asp
145                 150                 155                 160

His Met Val Leu Leu Glu Phe Val Thr Ala Ala Gly Ile Thr Leu Gly
                165                 170                 175
```

Met Asp Glu Leu Tyr Asn Val Asp Gly Gly Ser Gly Gly Thr Gly Ser
180 185 190

Lys Gly Glu Glu Leu Phe Thr Gly Val Val Pro Ile Leu Val Glu Leu
195 200 205

Asp Gly Asp Val Asn Gly His Lys Phe Ser Val Ser Gly Glu Gly Glu
210 215 220

Gly Asp Ala Thr Tyr Gly Lys Leu Thr Leu Lys Leu Ile Cys Thr Thr
225 230 235 240

Gly Lys Leu Pro Val Pro Trp Pro Thr Leu Val Thr Thr Leu Gly Tyr
245 250 255

Gly Leu Lys Cys Phe Ala Arg Tyr Pro Asp His Met Lys Gln His Asp
260 265 270

Phe Phe Lys Ser Ala Met Pro Glu Gly Tyr Val Gln Glu Arg Thr Ile
275 280 285

Phe Phe Lys Asp Asp Gly Asn Tyr Lys Thr Arg Ala Glu Val Lys Phe
290 295 300

Glu Gly Asp Thr Leu Val Asn Arg Ile Glu Leu Lys Gly Ile Gly Phe
305 310 315 320

Lys Glu Asp Gly Asn Ile Leu Gly His Lys Leu Glu Tyr Asn Tyr Tyr
325 330 335

Glu Gly Leu Ser Ala Val Val Val Thr Arg Lys Gly Ala Tyr His Thr
340 345 350

Phe Ala Asp Leu Lys Gly Lys Lys Val Gly Leu Glu Asn Gly Thr Thr
355 360 365

His Gln Arg Tyr Leu Gln Asp Lys Gln Gln Ala Ile Thr Pro Val Ala
370 375 380

Tyr Asp Ser Tyr Leu Asn Ala Phe Thr Asp Leu Lys Asn Asn Arg Leu
385 390 395 400

Glu Gly Val Phe Gly Asp Val Ala Ala Ile Gly Lys Trp Leu Lys Asn
405 410 415

Asn Pro Asp Tyr Ala Ile Met Asp Glu Arg Ala Ser Asp Pro Asp Tyr
420 425 430

Tyr Gly Lys Gly Leu Gly Ile Ala Val Arg Lys Asp Asn Asp Ala Leu
435 440 445

Leu Gln Glu Ile Asn Ala Ala Leu Asp Lys Val Lys Ala Ser Pro Glu
450 455 460

Tyr Ala Gln Met Gln Glu Lys Trp Phe Thr Gln
465 470 475

<210> SEQ ID NO 10
<211> LENGTH: 474
<212> TYPE: PRT
<213> ORGANISM: Artificial Sequence
<220> FEATURE:
<223> OTHER INFORMATION: sensor

<400> SEQUENCE: 10

Ala Ser Val Ser Ala Arg Thr Leu His Phe Gly Thr Ser Ala Thr Tyr
1 5 10 15

Ala Pro Tyr Glu Phe Val Asp Ala Asp Asn Lys Ile Val Gly Phe Asp
20 25 30

Ile Asp Val Ala Asn Ala Val Cys Lys Glu Met Gln Ala Glu Cys Ser
35 40 45

Phe Thr Asn Gln Ser Phe Asp Ser Leu Ile Pro Ser Leu Arg Phe Lys
50 55 60

```
Lys Phe Asp Ala Val Ile Ala Gly Met Asp Met Thr Pro Lys Arg Glu
65                  70                  75                  80

Gln Gln Val Ser Phe Ser Gln Pro Tyr Asn Ser Asp Asn Val Tyr Ile
                85                  90                  95

Met Ala Asp Lys Gln Lys Asn Gly Ile Lys Ala Asn Phe Lys Ile Arg
            100                 105                 110

His Asn Val Glu Asp Gly Ser Val Gln Leu Ala Asp His Tyr Gln Gln
        115                 120                 125

Asn Thr Pro Ile Gly Asp Gly Pro Val Leu Leu Pro Asp Asn His Tyr
    130                 135                 140

Leu Ser Phe Gln Ser Val Leu Ser Lys Asp Pro Asn Glu Lys Arg Asp
145                 150                 155                 160

His Met Val Leu Leu Glu Phe Val Thr Ala Ala Gly Ile Thr Leu Gly
                165                 170                 175

Met Asp Glu Leu Tyr Asn Val Asp Gly Gly Ser Gly Gly Thr Gly Ser
            180                 185                 190

Lys Gly Glu Glu Leu Phe Thr Gly Val Val Pro Ile Leu Val Glu Leu
        195                 200                 205

Asp Gly Asp Val Asn Gly His Lys Phe Ser Val Ser Gly Glu Gly Glu
    210                 215                 220

Gly Asp Ala Thr Tyr Gly Lys Leu Thr Leu Lys Leu Ile Cys Thr Thr
225                 230                 235                 240

Gly Lys Leu Pro Val Pro Trp Pro Thr Leu Val Thr Thr Leu Gly Tyr
                245                 250                 255

Gly Leu Lys Cys Phe Ala Arg Tyr Pro Asp His Met Lys Gln His Asp
            260                 265                 270

Phe Phe Lys Ser Ala Met Pro Glu Gly Tyr Val Gln Glu Arg Thr Ile
        275                 280                 285

Phe Phe Lys Asp Asp Gly Asn Tyr Lys Thr Arg Ala Glu Val Lys Phe
    290                 295                 300

Glu Gly Asp Thr Leu Val Asn Arg Ile Glu Leu Lys Gly Ile Gly Phe
305                 310                 315                 320

Lys Glu Asp Gly Asn Ile Leu Gly His Lys Leu Glu Tyr Asn Tyr Glu
                325                 330                 335

Gly Leu Ser Ala Val Val Val Thr Arg Lys Gly Ala Tyr His Thr Phe
            340                 345                 350

Ala Asp Leu Lys Gly Lys Lys Val Gly Leu Glu Asn Gly Thr Thr His
        355                 360                 365

Gln Arg Tyr Leu Gln Asp Lys Gln Gln Ala Ile Thr Pro Val Ala Tyr
    370                 375                 380

Asp Ser Tyr Leu Asn Ala Phe Thr Asp Leu Lys Asn Asn Arg Leu Glu
385                 390                 395                 400

Gly Val Phe Gly Asp Val Ala Ala Ile Gly Lys Trp Leu Lys Asn Asn
                405                 410                 415

Pro Asp Tyr Ala Ile Met Asp Glu Arg Ala Ser Asp Pro Asp Tyr Tyr
            420                 425                 430

Gly Lys Gly Leu Gly Ile Ala Val Arg Lys Asp Asn Asp Ala Leu Leu
        435                 440                 445

Gln Glu Ile Asn Ala Ala Leu Asp Lys Val Lys Ala Ser Pro Glu Tyr
    450                 455                 460

Ala Gln Met Gln Glu Lys Trp Phe Thr Gln
465                 470
```

-continued

<210> SEQ ID NO 11
<211> LENGTH: 471
<212> TYPE: PRT
<213> ORGANISM: Artificial Sequence
<220> FEATURE:
<223> OTHER INFORMATION: sensor

<400> SEQUENCE: 11

Ala Ser Val Ser Ala Arg Thr Leu His Phe Gly Thr Ser Ala Thr Tyr
1 5 10 15

Ala Pro Tyr Glu Phe Val Asp Ala Asp Asn Lys Ile Val Gly Phe Asp
20 25 30

Ile Asp Val Ala Asn Ala Val Cys Lys Glu Met Gln Ala Glu Cys Ser
35 40 45

Phe Thr Asn Gln Ser Phe Asp Ser Leu Ile Pro Ser Leu Arg Phe Lys
50 55 60

Lys Phe Asp Ala Val Ile Ala Gly Met Asp Met Thr Pro Lys Arg Glu
65 70 75 80

Gln Gln Val Ser Phe Ser Gln Pro Tyr Asn Ser Asp Asn Val Tyr Ile
85 90 95

Met Ala Asp Lys Gln Lys Asn Gly Ile Lys Ala Asn Phe Lys Ile Arg
100 105 110

His Asn Val Glu Asp Gly Ser Val Gln Leu Ala Asp His Tyr Gln Gln
115 120 125

Asn Thr Pro Ile Gly Asp Gly Pro Val Leu Leu Pro Asp Asn His Tyr
130 135 140

Leu Ser Phe Gln Ser Val Leu Ser Lys Asp Pro Asn Glu Lys Arg Asp
145 150 155 160

His Met Val Leu Leu Glu Phe Val Thr Ala Ala Gly Ile Thr Leu Gly
165 170 175

Met Asp Glu Leu Tyr Asn Val Asp Gly Gly Ser Gly Gly Thr Gly Ser
180 185 190

Lys Gly Glu Glu Leu Phe Thr Gly Val Val Pro Ile Leu Val Glu Leu
195 200 205

Asp Gly Asp Val Asn Gly His Lys Phe Ser Val Ser Gly Glu Gly Glu
210 215 220

Gly Asp Ala Thr Tyr Gly Lys Leu Thr Leu Lys Leu Ile Cys Thr Thr
225 230 235 240

Gly Lys Leu Pro Val Pro Trp Pro Thr Leu Val Thr Thr Leu Gly Tyr
245 250 255

Gly Leu Lys Cys Phe Ala Arg Tyr Pro Asp His Met Lys Gln His Asp
260 265 270

Phe Phe Lys Ser Ala Met Pro Glu Gly Tyr Val Gln Glu Arg Thr Ile
275 280 285

Phe Phe Lys Asp Asp Gly Asn Tyr Lys Thr Arg Ala Glu Val Lys Phe
290 295 300

Glu Gly Asp Thr Leu Val Asn Arg Ile Glu Leu Lys Gly Ile Gly Phe
305 310 315 320

Lys Glu Asp Gly Asn Ile Leu Gly His Lys Leu Glu Tyr Asn Leu Ser
325 330 335

Ala Val Val Val Thr Arg Lys Gly Ala Tyr His Thr Phe Ala Asp Leu
340 345 350

Lys Gly Lys Lys Val Gly Leu Glu Asn Gly Thr Thr His Gln Arg Tyr
355 360 365

```
Leu Gln Asp Lys Gln Gln Ala Ile Thr Pro Val Ala Tyr Asp Ser Tyr
    370                 375                 380

Leu Asn Ala Phe Thr Asp Leu Lys Asn Asn Arg Leu Glu Gly Val Phe
385                 390                 395                 400

Gly Asp Val Ala Ala Ile Gly Lys Trp Leu Lys Asn Asn Pro Asp Tyr
                405                 410                 415

Ala Ile Met Asp Glu Arg Ala Ser Asp Pro Asp Tyr Tyr Gly Lys Gly
            420                 425                 430

Leu Gly Ile Ala Val Arg Lys Asp Asn Asp Ala Leu Leu Gln Glu Ile
        435                 440                 445

Asn Ala Ala Leu Asp Lys Val Lys Ala Ser Pro Glu Tyr Ala Gln Met
    450                 455                 460

Gln Glu Lys Trp Phe Thr Gln
465                 470


<210> SEQ ID NO 12
<211> LENGTH: 474
<212> TYPE: PRT
<213> ORGANISM: Artificial Sequence
<220> FEATURE:
<223> OTHER INFORMATION: sensor

<400> SEQUENCE: 12

Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Tyr Asn Ser Asp Asn Val Tyr
                85                  90                  95

Ile Met Ala Asp Lys Gln Lys Asn Gly Ile Lys Ala Asn Phe Lys Ile
            100                 105                 110

Arg His Asn Val Glu Asp Gly Ser Val Gln Leu Ala Asp His Tyr Gln
        115                 120                 125

Gln Asn Thr Pro Ile Gly Asp Gly Pro Val Leu Leu Pro Asp Asn His
    130                 135                 140

Tyr Leu Ser Phe Gln Ser Val Leu Ser Lys Asp Pro Asn Glu Lys Arg
145                 150                 155                 160

Asp His Met Val Leu Leu Glu Phe Val Thr Ala Ala Gly Ile Thr Leu
                165                 170                 175

Gly Met Asp Glu Leu Tyr Asn Val Asp Gly Gly Ser Gly Gly Thr Gly
            180                 185                 190

Ser Lys Gly Glu Glu Leu Phe Thr Gly Val Val Pro Ile Leu Val Glu
        195                 200                 205

Leu Asp Gly Asp Val Asn Gly His Lys Phe Ser Val Ser Gly Glu Gly
    210                 215                 220

Glu Gly Asp Ala Thr Tyr Gly Lys Leu Thr Leu Lys Leu Ile Cys Thr
225                 230                 235                 240

Thr Gly Lys Leu Pro Val Pro Trp Pro Thr Leu Val Thr Thr Leu Gly
                245                 250                 255
```

```
Tyr Gly Leu Lys Cys Phe Ala Arg Tyr Pro Asp His Met Lys Gln His
            260                 265                 270

Asp Phe Phe Lys Ser Ala Met Pro Glu Gly Tyr Val Gln Glu Arg Thr
        275                 280                 285

Ile Phe Phe Lys Asp Asp Gly Asn Tyr Lys Thr Arg Ala Glu Val Lys
    290                 295                 300

Phe Glu Gly Asp Thr Leu Val Asn Arg Ile Glu Leu Lys Gly Ile Gly
305                 310                 315                 320

Phe Lys Glu Asp Gly Asn Ile Leu Gly His Lys Leu Glu Tyr Asn Glu
                325                 330                 335

Gly Leu Ser Ala Val Val Val Thr Arg Lys Gly Ala Tyr His Thr Phe
            340                 345                 350

Ala Asp Leu Lys Gly Lys Lys Val Gly Leu Glu Asn Gly Thr Thr His
        355                 360                 365

Gln Arg Tyr Leu Gln Asp Lys Gln Gln Ala Ile Thr Pro Val Ala Tyr
    370                 375                 380

Asp Ser Tyr Leu Asn Ala Phe Thr Asp Leu Lys Asn Asn Arg Leu Glu
385                 390                 395                 400

Gly Val Phe Gly Asp Val Ala Ala Ile Gly Lys Trp Leu Lys Asn Asn
                405                 410                 415

Pro Asp Tyr Ala Ile Met Asp Glu Arg Ala Ser Asp Pro Asp Tyr Tyr
            420                 425                 430

Gly Lys Gly Leu Gly Ile Ala Val Arg Lys Asp Asn Asp Ala Leu Leu
        435                 440                 445

Gln Glu Ile Asn Ala Ala Leu Asp Lys Val Lys Ala Ser Pro Glu Tyr
    450                 455                 460

Ala Gln Met Gln Glu Lys Trp Phe Thr Gln
465                 470
```

<210> SEQ ID NO 13
<211> LENGTH: 473
<212> TYPE: PRT
<213> ORGANISM: Artificial Sequence
<220> FEATURE:
<223> OTHER INFORMATION: sensor

<400> SEQUENCE: 13

```
Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Tyr Asn Ser Asp Asn Val Tyr
                85                  90                  95

Ile Met Ala Asp Lys Gln Lys Asn Gly Ile Lys Ala Asn Phe Lys Ile
            100                 105                 110

Arg His Asn Val Glu Asp Gly Ser Val Gln Leu Ala Asp His Tyr Gln
        115                 120                 125

Gln Asn Thr Pro Ile Gly Asp Gly Pro Val Leu Leu Pro Asp Asn His
    130                 135                 140
```

```
Tyr Leu Ser Phe Gln Ser Val Leu Ser Lys Asp Pro Asn Glu Lys Arg
145                 150                 155                 160

Asp His Met Val Leu Leu Glu Phe Val Thr Ala Ala Gly Ile Thr Leu
                165                 170                 175

Gly Met Asp Glu Leu Tyr Asn Val Asp Gly Gly Ser Gly Gly Thr Gly
            180                 185                 190

Ser Lys Gly Glu Glu Leu Phe Thr Gly Val Val Pro Ile Leu Val Glu
        195                 200                 205

Leu Asp Gly Asp Val Asn Gly His Lys Phe Ser Val Ser Gly Glu Gly
    210                 215                 220

Glu Gly Asp Ala Thr Tyr Gly Lys Leu Thr Leu Lys Leu Ile Cys Thr
225                 230                 235                 240

Thr Gly Lys Leu Pro Val Pro Trp Pro Thr Leu Val Thr Thr Leu Gly
                245                 250                 255

Tyr Gly Leu Lys Cys Phe Ala Arg Tyr Pro Asp His Met Lys Gln His
            260                 265                 270

Asp Phe Phe Lys Ser Ala Met Pro Glu Gly Tyr Val Gln Glu Arg Thr
        275                 280                 285

Ile Phe Phe Lys Asp Asp Gly Asn Tyr Lys Thr Arg Ala Glu Val Lys
    290                 295                 300

Phe Glu Gly Asp Thr Leu Val Asn Arg Ile Glu Leu Lys Gly Ile Gly
305                 310                 315                 320

Phe Lys Glu Asp Gly Asn Ile Leu Gly His Lys Leu Glu Tyr Asn Gly
                325                 330                 335

Leu Ser Ala Val Val Val Thr Arg Lys Gly Ala Tyr His Thr Phe Ala
            340                 345                 350

Asp Leu Lys Gly Lys Lys Val Gly Leu Glu Asn Gly Thr Thr His Gln
        355                 360                 365

Arg Tyr Leu Gln Asp Lys Gln Gln Ala Ile Thr Pro Val Ala Tyr Asp
    370                 375                 380

Ser Tyr Leu Asn Ala Phe Thr Asp Leu Lys Asn Asn Arg Leu Glu Gly
385                 390                 395                 400

Val Phe Gly Asp Val Ala Ala Ile Gly Lys Trp Leu Lys Asn Asn Pro
                405                 410                 415

Asp Tyr Ala Ile Met Asp Glu Arg Ala Ser Asp Pro Asp Tyr Tyr Gly
            420                 425                 430

Lys Gly Leu Gly Ile Ala Val Arg Lys Asp Asn Asp Ala Leu Leu Gln
        435                 440                 445

Glu Ile Asn Ala Ala Leu Asp Lys Val Lys Ala Ser Pro Glu Tyr Ala
    450                 455                 460

Gln Met Gln Glu Lys Trp Phe Thr Gln
465                 470
```

<210> SEQ ID NO 14
<211> LENGTH: 474
<212> TYPE: PRT
<213> ORGANISM: Artificial Sequence
<220> FEATURE:
<223> OTHER INFORMATION: sensor

<400> SEQUENCE: 14

```
Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30
```

-continued

```
Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Tyr Tyr Asn Ser Asp Asn Val
                85                  90                  95

Tyr Ile Met Ala Asp Lys Gln Lys Asn Gly Ile Lys Ala Asn Phe Lys
            100                 105                 110

Ile Arg His Asn Val Glu Asp Gly Ser Val Gln Leu Ala Asp His Tyr
        115                 120                 125

Gln Gln Asn Thr Pro Ile Gly Asp Gly Pro Val Leu Leu Pro Asp Asn
    130                 135                 140

His Tyr Leu Ser Phe Gln Ser Val Leu Ser Lys Asp Pro Asn Glu Lys
145                 150                 155                 160

Arg Asp His Met Val Leu Leu Glu Phe Val Thr Ala Ala Gly Ile Thr
                165                 170                 175

Leu Gly Met Asp Glu Leu Tyr Asn Val Asp Gly Gly Ser Gly Gly Thr
            180                 185                 190

Gly Ser Lys Gly Glu Glu Leu Phe Thr Gly Val Val Pro Ile Leu Val
        195                 200                 205

Glu Leu Asp Gly Asp Val Asn Gly His Lys Phe Ser Val Ser Gly Glu
    210                 215                 220

Gly Glu Gly Asp Ala Thr Tyr Gly Lys Leu Thr Leu Lys Leu Ile Cys
225                 230                 235                 240

Thr Thr Gly Lys Leu Pro Val Pro Trp Pro Thr Leu Val Thr Thr Leu
                245                 250                 255

Gly Tyr Gly Leu Lys Cys Phe Ala Arg Tyr Pro Asp His Met Lys Gln
            260                 265                 270

His Asp Phe Phe Lys Ser Ala Met Pro Glu Gly Tyr Val Gln Glu Arg
        275                 280                 285

Thr Ile Phe Phe Lys Asp Asp Gly Asn Tyr Lys Thr Arg Ala Glu Val
    290                 295                 300

Lys Phe Glu Gly Asp Thr Leu Val Asn Arg Ile Glu Leu Lys Gly Ile
305                 310                 315                 320

Gly Phe Lys Glu Asp Gly Asn Ile Leu Gly His Lys Leu Glu Tyr Asn
                325                 330                 335

Gly Leu Ser Ala Val Val Val Thr Arg Lys Gly Ala Tyr His Thr Phe
            340                 345                 350

Ala Asp Leu Lys Gly Lys Lys Val Gly Leu Glu Asn Gly Thr Thr His
        355                 360                 365

Gln Arg Tyr Leu Gln Asp Lys Gln Gln Ala Ile Thr Pro Val Ala Tyr
    370                 375                 380

Asp Ser Tyr Leu Asn Ala Phe Thr Asp Leu Lys Asn Asn Arg Leu Glu
385                 390                 395                 400

Gly Val Phe Gly Asp Val Ala Ala Ile Gly Lys Trp Leu Lys Asn Asn
                405                 410                 415

Pro Asp Tyr Ala Ile Met Asp Glu Arg Ala Ser Asp Pro Asp Tyr Tyr
            420                 425                 430

Gly Lys Gly Leu Gly Ile Ala Val Arg Lys Asp Asn Asp Ala Leu Leu
        435                 440                 445
```

```
Gln Glu Ile Asn Ala Ala Leu Asp Lys Val Lys Ala Ser Pro Glu Tyr
    450                 455                 460

Ala Gln Met Gln Glu Lys Trp Phe Thr Gln
465                 470


<210> SEQ ID NO 15
<211> LENGTH: 472
<212> TYPE: PRT
<213> ORGANISM: Artificial Sequence
<220> FEATURE:
<223> OTHER INFORMATION: sensor

<400> SEQUENCE: 15

Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Tyr Tyr Asn Ser Asp Asn Val
                85                  90                  95

Tyr Ile Met Ala Asp Lys Gln Lys Asn Gly Ile Lys Ala Asn Phe Lys
            100                 105                 110

Ile Arg His Asn Val Glu Asp Gly Ser Val Gln Leu Ala Asp His Tyr
        115                 120                 125

Gln Gln Asn Thr Pro Ile Gly Asp Gly Pro Val Leu Leu Pro Asp Asn
    130                 135                 140

His Tyr Leu Ser Phe Gln Ser Val Leu Ser Lys Asp Pro Asn Glu Lys
145                 150                 155                 160

Arg Asp His Met Val Leu Leu Glu Phe Val Thr Ala Ala Gly Ile Thr
                165                 170                 175

Leu Gly Met Asp Glu Leu Tyr Asn Val Asp Gly Gly Ser Gly Gly Thr
            180                 185                 190

Gly Ser Lys Gly Glu Glu Leu Phe Thr Gly Val Val Pro Ile Leu Val
        195                 200                 205

Glu Leu Asp Gly Asp Val Asn Gly His Lys Phe Ser Val Ser Gly Glu
    210                 215                 220

Gly Glu Gly Asp Ala Thr Tyr Gly Lys Leu Thr Leu Lys Leu Ile Cys
225                 230                 235                 240

Thr Thr Gly Lys Leu Pro Val Pro Trp Pro Thr Leu Val Thr Thr Leu
                245                 250                 255

Gly Tyr Gly Leu Lys Cys Phe Ala Arg Tyr Pro Asp His Met Lys Gln
            260                 265                 270

His Asp Phe Phe Lys Ser Ala Met Pro Glu Gly Tyr Val Gln Glu Arg
        275                 280                 285

Thr Ile Phe Phe Lys Asp Asp Gly Asn Tyr Lys Thr Arg Ala Glu Val
    290                 295                 300

Lys Phe Glu Gly Asp Thr Leu Val Asn Arg Ile Glu Leu Lys Gly Ile
305                 310                 315                 320

Gly Phe Lys Glu Asp Gly Asn Ile Leu Gly His Lys Leu Glu Tyr Asn
                325                 330                 335
```

```
Ser Ala Val Val Val Thr Arg Lys Gly Ala Tyr His Thr Phe Ala Asp
            340                 345                 350

Leu Lys Gly Lys Lys Val Gly Leu Glu Asn Gly Thr Thr His Gln Arg
        355                 360                 365

Tyr Leu Gln Asp Lys Gln Gln Ala Ile Thr Pro Val Ala Tyr Asp Ser
    370                 375                 380

Tyr Leu Asn Ala Phe Thr Asp Leu Lys Asn Asn Arg Leu Glu Gly Val
385                 390                 395                 400

Phe Gly Asp Val Ala Ala Ile Gly Lys Trp Leu Lys Asn Asn Pro Asp
                405                 410                 415

Tyr Ala Ile Met Asp Glu Arg Ala Ser Asp Pro Asp Tyr Tyr Gly Lys
            420                 425                 430

Gly Leu Gly Ile Ala Val Arg Lys Asp Asn Asp Ala Leu Leu Gln Glu
        435                 440                 445

Ile Asn Ala Ala Leu Asp Lys Val Lys Ala Ser Pro Glu Tyr Ala Gln
    450                 455                 460

Met Gln Glu Lys Trp Phe Thr Gln
465                 470


<210> SEQ ID NO 16
<211> LENGTH: 475
<212> TYPE: PRT
<213> ORGANISM: Artificial Sequence
<220> FEATURE:
<223> OTHER INFORMATION: sensor

<400> SEQUENCE: 16

Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Tyr Glu Gly Leu Tyr Asn Ser
                85                  90                  95

Asp Asn Val Tyr Ile Met Ala Asp Lys Gln Lys Asn Gly Ile Lys Ala
            100                 105                 110

Asn Phe Lys Ile Arg His Asn Val Glu Asp Gly Ser Val Gln Leu Ala
        115                 120                 125

Asp His Tyr Gln Gln Asn Thr Pro Ile Gly Asp Gly Pro Val Leu Leu
    130                 135                 140

Pro Asp Asn His Tyr Leu Ser Phe Gln Ser Val Leu Ser Lys Asp Pro
145                 150                 155                 160

Asn Glu Lys Arg Asp His Met Val Leu Leu Glu Phe Val Thr Ala Ala
                165                 170                 175

Gly Ile Thr Leu Gly Met Asp Glu Leu Tyr Asn Val Asp Gly Gly Ser
            180                 185                 190

Gly Gly Thr Gly Ser Lys Gly Glu Glu Leu Phe Thr Gly Val Val Pro
        195                 200                 205

Ile Leu Val Glu Leu Asp Gly Asp Val Asn Gly His Lys Phe Ser Val
    210                 215                 220
```

```
Ser Gly Glu Gly Glu Gly Asp Ala Thr Tyr Gly Lys Leu Thr Leu Lys
225                 230                 235                 240

Leu Ile Cys Thr Thr Gly Lys Leu Pro Val Pro Trp Pro Thr Leu Val
                245                 250                 255

Thr Thr Leu Gly Tyr Gly Leu Lys Cys Phe Ala Arg Tyr Pro Asp His
            260                 265                 270

Met Lys Gln His Asp Phe Phe Lys Ser Ala Met Pro Glu Gly Tyr Val
        275                 280                 285

Gln Glu Arg Thr Ile Phe Phe Lys Asp Asp Gly Asn Tyr Lys Thr Arg
    290                 295                 300

Ala Glu Val Lys Phe Glu Gly Asp Thr Leu Val Asn Arg Ile Glu Leu
305                 310                 315                 320

Lys Gly Ile Gly Phe Lys Glu Asp Gly Asn Ile Leu Gly His Lys Leu
                325                 330                 335

Glu Tyr Asn Ser Ala Val Val Val Thr Arg Lys Gly Ala Tyr His Thr
            340                 345                 350

Phe Ala Asp Leu Lys Gly Lys Lys Val Gly Leu Glu Asn Gly Thr Thr
        355                 360                 365

His Gln Arg Tyr Leu Gln Asp Lys Gln Gln Ala Ile Thr Pro Val Ala
    370                 375                 380

Tyr Asp Ser Tyr Leu Asn Ala Phe Thr Asp Leu Lys Asn Asn Arg Leu
385                 390                 395                 400

Glu Gly Val Phe Gly Asp Val Ala Ala Ile Gly Lys Trp Leu Lys Asn
                405                 410                 415

Asn Pro Asp Tyr Ala Ile Met Asp Glu Arg Ala Ser Asp Pro Asp Tyr
            420                 425                 430

Tyr Gly Lys Gly Leu Gly Ile Ala Val Arg Lys Asp Asn Asp Ala Leu
        435                 440                 445

Leu Gln Glu Ile Asn Ala Ala Leu Asp Lys Val Lys Ala Ser Pro Glu
    450                 455                 460

Tyr Ala Gln Met Gln Glu Lys Trp Phe Thr Gln
465                 470                 475


<210> SEQ ID NO 17
<211> LENGTH: 474
<212> TYPE: PRT
<213> ORGANISM: Artificial Sequence
<220> FEATURE:
<223> OTHER INFORMATION: sensor

<400> SEQUENCE: 17

Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Tyr Glu Gly Leu Ser Ala Val
                85                  90                  95

Val Val Thr Arg Lys Gly Ala Tyr His Thr Phe Ala Asp Leu Lys Gly
            100                 105                 110
```

```
Lys Lys Val Gly Leu Glu Asn Gly Thr Thr His Gln Arg Tyr Leu Gln
        115                 120                 125

Asp Lys Gln Gln Ala Ile Thr Pro Val Ala Tyr Asp Ser Tyr Leu Asn
    130                 135                 140

Ala Phe Thr Asp Leu Lys Asn Asn Arg Leu Glu Gly Val Phe Gly Asp
145                 150                 155                 160

Val Ala Ala Ile Gly Lys Trp Leu Lys Asn Asn Pro Asp Tyr Ala Ile
                165                 170                 175

Met Asp Glu Arg Tyr Asn Ser Asp Asn Val Tyr Ile Met Ala Asp Lys
            180                 185                 190

Gln Lys Asn Gly Ile Lys Ala Asn Phe Lys Ile Arg His Asn Val Glu
        195                 200                 205

Asp Gly Ser Val Gln Leu Ala Asp His Tyr Gln Gln Asn Thr Pro Ile
    210                 215                 220

Gly Asp Gly Pro Val Leu Leu Pro Asp Asn His Tyr Leu Ser Phe Gln
225                 230                 235                 240

Ser Val Leu Ser Lys Asp Pro Asn Glu Lys Arg Asp His Met Val Leu
                245                 250                 255

Leu Glu Phe Val Thr Ala Ala Gly Ile Thr Leu Gly Met Asp Glu Leu
            260                 265                 270

Tyr Asn Val Asp Gly Gly Ser Gly Gly Thr Gly Ser Lys Gly Glu Glu
        275                 280                 285

Leu Phe Thr Gly Val Val Pro Ile Leu Val Glu Leu Asp Gly Asp Val
    290                 295                 300

Asn Gly His Lys Phe Ser Val Ser Gly Glu Gly Glu Gly Asp Ala Thr
305                 310                 315                 320

Tyr Gly Lys Leu Thr Leu Lys Leu Ile Cys Thr Thr Gly Lys Leu Pro
                325                 330                 335

Val Pro Trp Pro Thr Leu Val Thr Thr Leu Gly Tyr Gly Leu Lys Cys
            340                 345                 350

Phe Ala Arg Tyr Pro Asp His Met Lys Gln His Asp Phe Phe Lys Ser
        355                 360                 365

Ala Met Pro Glu Gly Tyr Val Gln Glu Arg Thr Ile Phe Phe Lys Asp
    370                 375                 380

Asp Gly Asn Tyr Lys Thr Arg Ala Glu Val Lys Phe Glu Gly Asp Thr
385                 390                 395                 400

Leu Val Asn Arg Ile Glu Leu Lys Gly Ile Gly Phe Lys Glu Asp Gly
                405                 410                 415

Asn Ile Leu Gly His Lys Leu Glu Tyr Asn Ser Asp Pro Asp Tyr Tyr
            420                 425                 430

Gly Lys Gly Leu Gly Ile Ala Val Arg Lys Asp Asn Asp Ala Leu Leu
        435                 440                 445

Gln Glu Ile Asn Ala Ala Leu Asp Lys Val Lys Ala Ser Pro Glu Tyr
    450                 455                 460

Ala Gln Met Gln Glu Lys Trp Phe Thr Gln
465                 470
```

<210> SEQ ID NO 18
<211> LENGTH: 470
<212> TYPE: PRT
<213> ORGANISM: Artificial Sequence
<220> FEATURE:
<223> OTHER INFORMATION: sensor

<400> SEQUENCE: 18

```
Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Tyr Glu Gly Leu Ser Ala Val
                85                  90                  95

Val Val Thr Arg Lys Gly Ala Tyr His Thr Phe Ala Asp Leu Lys Gly
            100                 105                 110

Lys Lys Val Gly Leu Glu Asn Gly Thr Thr His Gln Arg Tyr Leu Gln
        115                 120                 125

Asp Lys Gln Gln Ala Ile Thr Pro Val Ala Tyr Asp Ser Tyr Leu Asn
    130                 135                 140

Ala Phe Thr Asp Leu Lys Asn Asn Arg Leu Glu Gly Val Phe Gly Asp
145                 150                 155                 160

Val Ala Ala Ile Gly Lys Trp Leu Lys Asn Asn Pro Asp Tyr Ala Ile
                165                 170                 175

Met Asp Glu Arg Tyr Asn Ser Asp Asn Val Tyr Ile Met Ala Asp Lys
            180                 185                 190

Gln Lys Asn Gly Ile Lys Ala Asn Phe Lys Ile Arg His Asn Val Glu
        195                 200                 205

Asp Gly Ser Val Gln Leu Ala Asp His Tyr Gln Gln Asn Thr Pro Ile
    210                 215                 220

Gly Asp Gly Pro Val Leu Leu Pro Asp Asn His Tyr Leu Ser Phe Gln
225                 230                 235                 240

Ser Val Leu Ser Lys Asp Pro Asn Glu Lys Arg Asp His Met Val Leu
                245                 250                 255

Leu Glu Phe Val Thr Ala Ala Gly Ile Thr Leu Gly Met Asp Glu Leu
            260                 265                 270

Tyr Asn Val Asp Gly Gly Ser Gly Gly Thr Gly Ser Lys Gly Glu Glu
        275                 280                 285

Leu Phe Thr Gly Val Val Pro Ile Leu Val Glu Leu Asp Gly Asp Val
    290                 295                 300

Asn Gly His Lys Phe Ser Val Ser Gly Glu Gly Glu Gly Asp Ala Thr
305                 310                 315                 320

Tyr Gly Lys Leu Thr Leu Lys Leu Ile Cys Thr Thr Gly Lys Leu Pro
                325                 330                 335

Val Pro Trp Pro Thr Leu Val Thr Thr Leu Gly Tyr Gly Leu Lys Cys
            340                 345                 350

Phe Ala Arg Tyr Pro Asp His Met Lys Gln His Asp Phe Phe Lys Ser
        355                 360                 365

Ala Met Pro Glu Gly Tyr Val Gln Glu Arg Thr Ile Phe Phe Lys Asp
    370                 375                 380

Asp Gly Asn Tyr Lys Thr Arg Ala Glu Val Lys Phe Glu Gly Asp Thr
385                 390                 395                 400
```

```
Leu Val Asn Arg Ile Glu Leu Lys Gly Ile Gly Phe Lys Glu Asp Gly
                405                 410                 415

Asn Ile Leu Gly His Lys Leu Glu Tyr Asn Tyr Tyr Gly Lys Gly Leu
            420                 425                 430

Gly Ile Ala Val Arg Lys Asp Asn Asp Ala Leu Leu Gln Glu Ile Asn
        435                 440                 445

Ala Ala Leu Asp Lys Val Lys Ala Ser Pro Glu Tyr Ala Gln Met Gln
    450                 455                 460

Glu Lys Trp Phe Thr Gln
465                 470


<210> SEQ ID NO 19
<211> LENGTH: 469
<212> TYPE: PRT
<213> ORGANISM: Artificial Sequence
<220> FEATURE:
<223> OTHER INFORMATION: sensor

<400> SEQUENCE: 19

Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Tyr Glu Gly Leu Ser Ala Val
                85                  90                  95

Val Val Thr Arg Lys Gly Ala Tyr His Thr Phe Ala Asp Leu Lys Gly
            100                 105                 110

Lys Lys Val Gly Leu Glu Asn Gly Thr Thr His Gln Arg Tyr Leu Gln
        115                 120                 125

Asp Lys Gln Gln Ala Ile Thr Pro Val Ala Tyr Asp Ser Tyr Leu Asn
    130                 135                 140

Ala Phe Thr Asp Leu Lys Asn Asn Arg Leu Glu Gly Val Phe Gly Asp
145                 150                 155                 160

Val Ala Ala Ile Gly Lys Trp Leu Lys Asn Asn Pro Asp Tyr Ala Ile
                165                 170                 175

Met Asp Glu Arg Tyr Asn Ser Asp Asn Val Tyr Ile Met Ala Asp Lys
            180                 185                 190

Gln Lys Asn Gly Ile Lys Ala Asn Phe Lys Ile Arg His Asn Val Glu
        195                 200                 205

Asp Gly Ser Val Gln Leu Ala Asp His Tyr Gln Gln Asn Thr Pro Ile
    210                 215                 220

Gly Asp Gly Pro Val Leu Leu Pro Asp Asn His Tyr Leu Ser Phe Gln
225                 230                 235                 240

Ser Val Leu Ser Lys Asp Pro Asn Glu Lys Arg Asp His Met Val Leu
                245                 250                 255

Leu Glu Phe Val Thr Ala Ala Gly Ile Thr Leu Gly Met Asp Glu Leu
            260                 265                 270

Tyr Asn Val Asp Gly Gly Ser Gly Gly Thr Gly Ser Lys Gly Glu Glu
        275                 280                 285
```

```
Leu Phe Thr Gly Val Val Pro Ile Leu Val Glu Leu Asp Gly Asp Val
    290                 295                 300

Asn Gly His Lys Phe Ser Val Ser Gly Glu Gly Glu Gly Asp Ala Thr
305                 310                 315                 320

Tyr Gly Lys Leu Thr Leu Lys Leu Ile Cys Thr Thr Gly Lys Leu Pro
                325                 330                 335

Val Pro Trp Pro Thr Leu Val Thr Thr Leu Gly Tyr Gly Leu Lys Cys
            340                 345                 350

Phe Ala Arg Tyr Pro Asp His Met Lys Gln His Asp Phe Phe Lys Ser
        355                 360                 365

Ala Met Pro Glu Gly Tyr Val Gln Glu Arg Thr Ile Phe Phe Lys Asp
    370                 375                 380

Asp Gly Asn Tyr Lys Thr Arg Ala Glu Val Lys Phe Glu Gly Asp Thr
385                 390                 395                 400

Leu Val Asn Arg Ile Glu Leu Lys Gly Ile Gly Phe Lys Glu Asp Gly
                405                 410                 415

Asn Ile Leu Gly His Lys Leu Glu Tyr Asn Tyr Gly Lys Gly Leu Gly
            420                 425                 430

Ile Ala Val Arg Lys Asp Asn Asp Ala Leu Leu Gln Glu Ile Asn Ala
        435                 440                 445

Ala Leu Asp Lys Val Lys Ala Ser Pro Glu Tyr Ala Gln Met Gln Glu
    450                 455                 460

Lys Trp Phe Thr Gln
465
```

<210> SEQ ID NO 20
<211> LENGTH: 472
<212> TYPE: PRT
<213> ORGANISM: Artificial Sequence
<220> FEATURE:
<223> OTHER INFORMATION: sensor

<400> SEQUENCE: 20

```
Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Tyr Glu Gly Leu Ser Ala Val
                85                  90                  95

Val Val Thr Arg Lys Gly Ala Tyr His Thr Phe Ala Asp Leu Lys Gly
            100                 105                 110

Lys Lys Val Gly Leu Glu Asn Gly Thr Thr His Gln Arg Tyr Leu Gln
        115                 120                 125

Asp Lys Gln Gln Ala Ile Thr Pro Val Ala Tyr Asp Ser Tyr Leu Asn
    130                 135                 140

Ala Phe Thr Asp Leu Lys Asn Asn Arg Leu Glu Gly Val Phe Gly Asp
145                 150                 155                 160

Val Ala Ala Ile Gly Lys Trp Leu Lys Asn Asn Pro Asp Tyr Ala Ile
                165                 170                 175
```

Met Asp Glu Arg Ala Tyr Asn Ser Asp Asn Val Tyr Ile Met Ala Asp
180 185 190

Lys Gln Lys Asn Gly Ile Lys Ala Asn Phe Lys Ile Arg His Asn Val
195 200 205

Glu Asp Gly Ser Val Gln Leu Ala Asp His Tyr Gln Gln Asn Thr Pro
210 215 220

Ile Gly Asp Gly Pro Val Leu Leu Pro Asp Asn His Tyr Leu Ser Phe
225 230 235 240

Gln Ser Val Leu Ser Lys Asp Pro Asn Glu Lys Arg Asp His Met Val
245 250 255

Leu Leu Glu Phe Val Thr Ala Ala Gly Ile Thr Leu Gly Met Asp Glu
260 265 270

Leu Tyr Asn Val Asp Gly Gly Ser Gly Gly Thr Gly Ser Lys Gly Glu
275 280 285

Glu Leu Phe Thr Gly Val Val Pro Ile Leu Val Glu Leu Asp Gly Asp
290 295 300

Val Asn Gly His Lys Phe Ser Val Ser Gly Glu Gly Glu Gly Asp Ala
305 310 315 320

Thr Tyr Gly Lys Leu Thr Leu Lys Leu Ile Cys Thr Thr Gly Lys Leu
325 330 335

Pro Val Pro Trp Pro Thr Leu Val Thr Thr Leu Gly Tyr Gly Leu Lys
340 345 350

Cys Phe Ala Arg Tyr Pro Asp His Met Lys Gln His Asp Phe Phe Lys
355 360 365

Ser Ala Met Pro Glu Gly Tyr Val Gln Glu Arg Thr Ile Phe Phe Lys
370 375 380

Asp Asp Gly Asn Tyr Lys Thr Arg Ala Glu Val Lys Phe Glu Gly Asp
385 390 395 400

Thr Leu Val Asn Arg Ile Glu Leu Lys Gly Ile Gly Phe Lys Glu Asp
405 410 415

Gly Asn Ile Leu Gly His Lys Leu Glu Tyr Asn Asp Tyr Tyr Gly Lys
420 425 430

Gly Leu Gly Ile Ala Val Arg Lys Asp Asn Asp Ala Leu Leu Gln Glu
435 440 445

Ile Asn Ala Ala Leu Asp Lys Val Lys Ala Ser Pro Glu Tyr Ala Gln
450 455 460

Met Gln Glu Lys Trp Phe Thr Gln
465 470

<210> SEQ ID NO 21
<211> LENGTH: 471
<212> TYPE: PRT
<213> ORGANISM: Artificial Sequence
<220> FEATURE:
<223> OTHER INFORMATION: sensor

<400> SEQUENCE: 21

Ala Ser Val Ser Ala Arg Thr Leu His Phe Gly Thr Ser Ala Thr Tyr
1 5 10 15

Ala Pro Tyr Glu Phe Val Asp Ala Asp Asn Lys Ile Val Gly Phe Asp
20 25 30

Ile Asp Val Ala Asn Ala Val Cys Lys Glu Met Gln Ala Glu Cys Ser
35 40 45

Phe Thr Asn Gln Ser Phe Asp Ser Leu Ile Pro Ser Leu Arg Phe Lys
50 55 60

```
Lys Phe Asp Ala Val Ile Ala Gly Met Asp Met Thr Pro Lys Arg Glu
65                  70                  75                  80

Gln Gln Val Ser Phe Ser Gln Pro Tyr Tyr Glu Gly Leu Ser Ala Val
                85                  90                  95

Val Val Thr Arg Lys Gly Ala Tyr His Thr Phe Ala Asp Leu Lys Gly
            100                 105                 110

Lys Lys Val Gly Leu Glu Asn Gly Thr Thr His Gln Arg Tyr Leu Gln
        115                 120                 125

Asp Lys Gln Gln Ala Ile Thr Pro Val Ala Tyr Asp Ser Tyr Leu Asn
    130                 135                 140

Ala Phe Thr Asp Leu Lys Asn Asn Arg Leu Glu Gly Val Phe Gly Asp
145                 150                 155                 160

Val Ala Ala Ile Gly Lys Trp Leu Lys Asn Asn Pro Asp Tyr Ala Ile
                165                 170                 175

Met Asp Glu Arg Ala Tyr Asn Ser Asp Asn Val Tyr Ile Met Ala Asp
            180                 185                 190

Lys Gln Lys Asn Gly Ile Lys Ala Asn Phe Lys Ile Arg His Asn Val
        195                 200                 205

Glu Asp Gly Ser Val Gln Leu Ala Asp His Tyr Gln Gln Asn Thr Pro
    210                 215                 220

Ile Gly Asp Gly Pro Val Leu Leu Pro Asp Asn His Tyr Leu Ser Phe
225                 230                 235                 240

Gln Ser Val Leu Ser Lys Asp Pro Asn Glu Lys Arg Asp His Met Val
                245                 250                 255

Leu Leu Glu Phe Val Thr Ala Ala Gly Ile Thr Leu Gly Met Asp Glu
            260                 265                 270

Leu Tyr Asn Val Asp Gly Gly Ser Gly Gly Thr Gly Ser Lys Gly Glu
        275                 280                 285

Glu Leu Phe Thr Gly Val Val Pro Ile Leu Val Glu Leu Asp Gly Asp
    290                 295                 300

Val Asn Gly His Lys Phe Ser Val Ser Gly Glu Gly Glu Gly Asp Ala
305                 310                 315                 320

Thr Tyr Gly Lys Leu Thr Leu Lys Leu Ile Cys Thr Thr Gly Lys Leu
                325                 330                 335

Pro Val Pro Trp Pro Thr Leu Val Thr Thr Leu Gly Tyr Gly Leu Lys
            340                 345                 350

Cys Phe Ala Arg Tyr Pro Asp His Met Lys Gln His Asp Phe Phe Lys
        355                 360                 365

Ser Ala Met Pro Glu Gly Tyr Val Gln Glu Arg Thr Ile Phe Phe Lys
    370                 375                 380

Asp Asp Gly Asn Tyr Lys Thr Arg Ala Glu Val Lys Phe Glu Gly Asp
385                 390                 395                 400

Thr Leu Val Asn Arg Ile Glu Leu Lys Gly Ile Gly Phe Lys Glu Asp
                405                 410                 415

Gly Asn Ile Leu Gly His Lys Leu Glu Tyr Asn Tyr Tyr Gly Lys Gly
            420                 425                 430

Leu Gly Ile Ala Val Arg Lys Asp Asn Asp Ala Leu Leu Gln Glu Ile
        435                 440                 445

Asn Ala Ala Leu Asp Lys Val Lys Ala Ser Pro Glu Tyr Ala Gln Met
    450                 455                 460

Gln Glu Lys Trp Phe Thr Gln
465                 470
```

<210> SEQ ID NO 22
<211> LENGTH: 475
<212> TYPE: PRT
<213> ORGANISM: Artificial Sequence
<220> FEATURE:
<223> OTHER INFORMATION: sensor

<400> SEQUENCE: 22

Ala Ser Val Ser Ala Arg Thr Leu His Phe Gly Thr Ser Ala Thr Tyr
1 5 10 15

Ala Pro Tyr Glu Phe Val Asp Ala Asp Asn Lys Ile Val Gly Phe Asp
20 25 30

Ile Asp Val Ala Asn Ala Val Cys Lys Glu Met Gln Ala Glu Cys Ser
35 40 45

Phe Thr Asn Gln Ser Phe Asp Ser Leu Ile Pro Ser Leu Arg Phe Lys
50 55 60

Lys Phe Asp Ala Val Ile Ala Gly Met Asp Met Thr Pro Lys Arg Glu
65 70 75 80

Gln Gln Val Ser Phe Ser Gln Pro Tyr Tyr Glu Gly Leu Ser Ala Val
85 90 95

Val Val Thr Arg Lys Gly Ala Tyr His Thr Phe Ala Asp Leu Lys Gly
100 105 110

Lys Lys Val Gly Leu Glu Asn Gly Thr Thr His Gln Arg Tyr Leu Gln
115 120 125

Asp Lys Gln Gln Ala Ile Thr Pro Val Ala Tyr Asp Ser Tyr Leu Asn
130 135 140

Ala Phe Thr Asp Leu Lys Asn Asn Arg Leu Glu Gly Val Phe Gly Asp
145 150 155 160

Val Ala Ala Ile Gly Lys Trp Leu Lys Asn Asn Pro Asp Tyr Ala Ile
165 170 175

Met Asp Glu Arg Ala Ser Tyr Asn Ser Asp Asn Val Tyr Ile Met Ala
180 185 190

Asp Lys Gln Lys Asn Gly Ile Lys Ala Asn Phe Lys Ile Arg His Asn
195 200 205

Val Glu Asp Gly Ser Val Gln Leu Ala Asp His Tyr Gln Gln Asn Thr
210 215 220

Pro Ile Gly Asp Gly Pro Val Leu Leu Pro Asp Asn His Tyr Leu Ser
225 230 235 240

Phe Gln Ser Val Leu Ser Lys Asp Pro Asn Glu Lys Arg Asp His Met
245 250 255

Val Leu Leu Glu Phe Val Thr Ala Ala Gly Ile Thr Leu Gly Met Asp
260 265 270

Glu Leu Tyr Asn Val Asp Gly Gly Ser Gly Gly Thr Gly Ser Lys Gly
275 280 285

Glu Glu Leu Phe Thr Gly Val Val Pro Ile Leu Val Glu Leu Asp Gly
290 295 300

Asp Val Asn Gly His Lys Phe Ser Val Ser Gly Glu Gly Glu Gly Asp
305 310 315 320

Ala Thr Tyr Gly Lys Leu Thr Leu Lys Leu Ile Cys Thr Thr Gly Lys
325 330 335

Leu Pro Val Pro Trp Pro Thr Leu Val Thr Thr Leu Gly Tyr Gly Leu
340 345 350

Lys Cys Phe Ala Arg Tyr Pro Asp His Met Lys Gln His Asp Phe Phe
355 360 365

```
Lys Ser Ala Met Pro Glu Gly Tyr Val Gln Glu Arg Thr Ile Phe Phe
    370                 375                 380

Lys Asp Asp Gly Asn Tyr Lys Thr Arg Ala Glu Val Lys Phe Glu Gly
385                 390                 395                 400

Asp Thr Leu Val Asn Arg Ile Glu Leu Lys Gly Ile Gly Phe Lys Glu
                405                 410                 415

Asp Gly Asn Ile Leu Gly His Lys Leu Glu Tyr Asn Asp Pro Asp Tyr
            420                 425                 430

Tyr Gly Lys Gly Leu Gly Ile Ala Val Arg Lys Asp Asn Asp Ala Leu
        435                 440                 445

Leu Gln Glu Ile Asn Ala Ala Leu Asp Lys Val Lys Ala Ser Pro Glu
    450                 455                 460

Tyr Ala Gln Met Gln Glu Lys Trp Phe Thr Gln
465                 470                 475


<210> SEQ ID NO 23
<211> LENGTH: 474
<212> TYPE: PRT
<213> ORGANISM: Artificial Sequence
<220> FEATURE:
<223> OTHER INFORMATION: sensor

<400> SEQUENCE: 23

Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Tyr Glu Gly Leu Ser Ala Val
                85                  90                  95

Val Val Thr Arg Lys Gly Ala Tyr His Thr Phe Ala Asp Leu Lys Gly
            100                 105                 110

Lys Lys Val Gly Leu Glu Asn Gly Thr Thr His Gln Arg Tyr Leu Gln
        115                 120                 125

Asp Lys Gln Gln Ala Ile Thr Pro Val Ala Tyr Asp Ser Tyr Leu Asn
    130                 135                 140

Ala Phe Thr Asp Leu Lys Asn Asn Arg Leu Glu Gly Val Phe Gly Asp
145                 150                 155                 160

Val Ala Ala Ile Gly Lys Trp Leu Lys Asn Asn Pro Asp Tyr Ala Ile
                165                 170                 175

Met Asp Glu Arg Ala Ser Tyr Asn Ser Asp Asn Val Tyr Ile Met Ala
            180                 185                 190

Asp Lys Gln Lys Asn Gly Ile Lys Ala Asn Phe Lys Ile Arg His Asn
        195                 200                 205

Val Glu Asp Gly Ser Val Gln Leu Ala Asp His Tyr Gln Gln Asn Thr
    210                 215                 220

Pro Ile Gly Asp Gly Pro Val Leu Leu Pro Asp Asn His Tyr Leu Ser
225                 230                 235                 240

Phe Gln Ser Val Leu Ser Lys Asp Pro Asn Glu Lys Arg Asp His Met
                245                 250                 255
```

```
Val Leu Leu Glu Phe Val Thr Ala Ala Gly Ile Thr Leu Gly Met Asp
            260                 265                 270

Glu Leu Tyr Asn Val Asp Gly Gly Ser Gly Gly Thr Gly Ser Lys Gly
        275                 280                 285

Glu Glu Leu Phe Thr Gly Val Val Pro Ile Leu Val Glu Leu Asp Gly
    290                 295                 300

Asp Val Asn Gly His Lys Phe Ser Val Ser Gly Glu Gly Glu Gly Asp
305                 310                 315                 320

Ala Thr Tyr Gly Lys Leu Thr Leu Lys Leu Ile Cys Thr Thr Gly Lys
                325                 330                 335

Leu Pro Val Pro Trp Pro Thr Leu Val Thr Thr Leu Gly Tyr Gly Leu
            340                 345                 350

Lys Cys Phe Ala Arg Tyr Pro Asp His Met Lys Gln His Asp Phe Phe
        355                 360                 365

Lys Ser Ala Met Pro Glu Gly Tyr Val Gln Glu Arg Thr Ile Phe Phe
    370                 375                 380

Lys Asp Asp Gly Asn Tyr Lys Thr Arg Ala Glu Val Lys Phe Glu Gly
385                 390                 395                 400

Asp Thr Leu Val Asn Arg Ile Glu Leu Lys Gly Ile Gly Phe Lys Glu
                405                 410                 415

Asp Gly Asn Ile Leu Gly His Lys Leu Glu Tyr Asn Pro Asp Tyr Tyr
            420                 425                 430

Gly Lys Gly Leu Gly Ile Ala Val Arg Lys Asp Asn Asp Ala Leu Leu
        435                 440                 445

Gln Glu Ile Asn Ala Ala Leu Asp Lys Val Lys Ala Ser Pro Glu Tyr
    450                 455                 460

Ala Gln Met Gln Glu Lys Trp Phe Thr Gln
465                 470


<210> SEQ ID NO 24
<211> LENGTH: 473
<212> TYPE: PRT
<213> ORGANISM: Artificial Sequence
<220> FEATURE:
<223> OTHER INFORMATION: sensor

<400> SEQUENCE: 24

Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Tyr Glu Gly Leu Ser Ala Val
                85                  90                  95

Val Val Thr Arg Lys Gly Ala Tyr His Thr Phe Ala Asp Leu Lys Gly
            100                 105                 110

Lys Lys Val Gly Leu Glu Asn Gly Thr Thr His Gln Arg Tyr Leu Gln
        115                 120                 125

Asp Lys Gln Gln Ala Ile Thr Pro Val Ala Tyr Asp Ser Tyr Leu Asn
    130                 135                 140
```

```
Ala Phe Thr Asp Leu Lys Asn Asn Arg Leu Glu Gly Val Phe Gly Asp
145                 150                 155                 160

Val Ala Ala Ile Gly Lys Trp Leu Lys Asn Asn Pro Asp Tyr Ala Ile
                165                 170                 175

Met Asp Glu Arg Ala Ser Tyr Asn Ser Asp Asn Val Tyr Ile Met Ala
            180                 185                 190

Asp Lys Gln Lys Asn Gly Ile Lys Ala Asn Phe Lys Ile Arg His Asn
        195                 200                 205

Val Glu Asp Gly Ser Val Gln Leu Ala Asp His Tyr Gln Gln Asn Thr
    210                 215                 220

Pro Ile Gly Asp Gly Pro Val Leu Leu Pro Asp Asn His Tyr Leu Ser
225                 230                 235                 240

Phe Gln Ser Val Leu Ser Lys Asp Pro Asn Glu Lys Arg Asp His Met
                245                 250                 255

Val Leu Leu Glu Phe Val Thr Ala Ala Gly Ile Thr Leu Gly Met Asp
            260                 265                 270

Glu Leu Tyr Asn Val Asp Gly Gly Ser Gly Gly Thr Gly Ser Lys Gly
        275                 280                 285

Glu Glu Leu Phe Thr Gly Val Val Pro Ile Leu Val Glu Leu Asp Gly
    290                 295                 300

Asp Val Asn Gly His Lys Phe Ser Val Ser Gly Glu Gly Glu Gly Asp
305                 310                 315                 320

Ala Thr Tyr Gly Lys Leu Thr Leu Lys Leu Ile Cys Thr Thr Gly Lys
                325                 330                 335

Leu Pro Val Pro Trp Pro Thr Leu Val Thr Thr Leu Gly Tyr Gly Leu
            340                 345                 350

Lys Cys Phe Ala Arg Tyr Pro Asp His Met Lys Gln His Asp Phe Phe
        355                 360                 365

Lys Ser Ala Met Pro Glu Gly Tyr Val Gln Glu Arg Thr Ile Phe Phe
    370                 375                 380

Lys Asp Asp Gly Asn Tyr Lys Thr Arg Ala Glu Val Lys Phe Glu Gly
385                 390                 395                 400

Asp Thr Leu Val Asn Arg Ile Glu Leu Lys Gly Ile Gly Phe Lys Glu
                405                 410                 415

Asp Gly Asn Ile Leu Gly His Lys Leu Glu Tyr Asn Asp Tyr Tyr Gly
            420                 425                 430

Lys Gly Leu Gly Ile Ala Val Arg Lys Asp Asn Asp Ala Leu Leu Gln
        435                 440                 445

Glu Ile Asn Ala Ala Leu Asp Lys Val Lys Ala Ser Pro Glu Tyr Ala
    450                 455                 460

Gln Met Gln Glu Lys Trp Phe Thr Gln
465                 470
```

<210> SEQ ID NO 25
<211> LENGTH: 471
<212> TYPE: PRT
<213> ORGANISM: Artificial Sequence
<220> FEATURE:
<223> OTHER INFORMATION: sensor

<400> SEQUENCE: 25

```
Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30
```

-continued

```
Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Tyr Glu Gly Leu Ser Ala Val
                85                  90                  95

Val Val Thr Arg Lys Gly Ala Tyr His Thr Phe Ala Asp Leu Lys Gly
            100                 105                 110

Lys Lys Val Gly Leu Glu Asn Gly Thr Thr His Gln Arg Tyr Leu Gln
        115                 120                 125

Asp Lys Gln Gln Ala Ile Thr Pro Val Ala Tyr Asp Ser Tyr Leu Asn
    130                 135                 140

Ala Phe Thr Asp Leu Lys Asn Asn Arg Leu Glu Gly Val Phe Gly Asp
145                 150                 155                 160

Val Ala Ala Ile Gly Lys Trp Leu Lys Asn Asn Pro Asp Tyr Ala Ile
                165                 170                 175

Met Asp Glu Arg Ala Ser Tyr Asn Ser Asp Asn Val Tyr Ile Met Ala
            180                 185                 190

Asp Lys Gln Lys Asn Gly Ile Lys Ala Asn Phe Lys Ile Arg His Asn
        195                 200                 205

Val Glu Asp Gly Ser Val Gln Leu Ala Asp His Tyr Gln Gln Asn Thr
    210                 215                 220

Pro Ile Gly Asp Gly Pro Val Leu Leu Pro Asp Asn His Tyr Leu Ser
225                 230                 235                 240

Phe Gln Ser Val Leu Ser Lys Asp Pro Asn Glu Lys Arg Asp His Met
                245                 250                 255

Val Leu Leu Glu Phe Val Thr Ala Ala Gly Ile Thr Leu Gly Met Asp
            260                 265                 270

Glu Leu Tyr Asn Val Asp Gly Gly Ser Gly Gly Thr Gly Ser Lys Gly
        275                 280                 285

Glu Glu Leu Phe Thr Gly Val Val Pro Ile Leu Val Glu Leu Asp Gly
    290                 295                 300

Asp Val Asn Gly His Lys Phe Ser Val Ser Gly Glu Gly Glu Gly Asp
305                 310                 315                 320

Ala Thr Tyr Gly Lys Leu Thr Leu Lys Leu Ile Cys Thr Thr Gly Lys
                325                 330                 335

Leu Pro Val Pro Trp Pro Thr Leu Val Thr Thr Leu Gly Tyr Gly Leu
            340                 345                 350

Lys Cys Phe Ala Arg Tyr Pro Asp His Met Lys Gln His Asp Phe Phe
        355                 360                 365

Lys Ser Ala Met Pro Glu Gly Tyr Val Gln Glu Arg Thr Ile Phe Phe
    370                 375                 380

Lys Asp Asp Gly Asn Tyr Lys Thr Arg Ala Glu Val Lys Phe Glu Gly
385                 390                 395                 400

Asp Thr Leu Val Asn Arg Ile Glu Leu Lys Gly Ile Gly Phe Lys Glu
                405                 410                 415

Asp Gly Asn Ile Leu Gly His Lys Leu Glu Tyr Asn Tyr Gly Lys Gly
            420                 425                 430

Leu Gly Ile Ala Val Arg Lys Asp Asn Asp Ala Leu Leu Gln Glu Ile
        435                 440                 445
```

```
Asn Ala Ala Leu Asp Lys Val Lys Ala Ser Pro Glu Tyr Ala Gln Met
    450                 455                 460

Gln Glu Lys Trp Phe Thr Gln
465                 470


<210> SEQ ID NO 26
<211> LENGTH: 470
<212> TYPE: PRT
<213> ORGANISM: Artificial Sequence
<220> FEATURE:
<223> OTHER INFORMATION: sensor

<400> SEQUENCE: 26

Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Tyr Glu Gly Leu Ser Ala Val
                85                  90                  95

Val Val Thr Arg Lys Gly Ala Tyr His Thr Phe Ala Asp Leu Lys Gly
            100                 105                 110

Lys Lys Val Gly Leu Glu Asn Gly Thr Thr His Gln Arg Tyr Leu Gln
        115                 120                 125

Asp Lys Gln Gln Ala Ile Thr Pro Val Ala Tyr Asp Ser Tyr Leu Asn
    130                 135                 140

Ala Phe Thr Asp Leu Lys Asn Asn Arg Leu Glu Gly Val Phe Gly Asp
145                 150                 155                 160

Val Ala Ala Ile Gly Lys Trp Leu Lys Asn Asn Pro Asp Tyr Ala Ile
                165                 170                 175

Met Asp Glu Arg Ala Ser Tyr Asn Ser Asp Asn Val Tyr Ile Met Ala
            180                 185                 190

Asp Lys Gln Lys Asn Gly Ile Lys Ala Asn Phe Lys Ile Arg His Asn
        195                 200                 205

Val Glu Asp Gly Ser Val Gln Leu Ala Asp His Tyr Gln Gln Asn Thr
    210                 215                 220

Pro Ile Gly Asp Gly Pro Val Leu Leu Pro Asp Asn His Tyr Leu Ser
225                 230                 235                 240

Phe Gln Ser Val Leu Ser Lys Asp Pro Asn Glu Lys Arg Asp His Met
                245                 250                 255

Val Leu Leu Glu Phe Val Thr Ala Ala Gly Ile Thr Leu Gly Met Asp
            260                 265                 270

Glu Leu Tyr Asn Val Asp Gly Gly Ser Gly Gly Thr Gly Ser Lys Gly
        275                 280                 285

Glu Glu Leu Phe Thr Gly Val Val Pro Ile Leu Val Glu Leu Asp Gly
    290                 295                 300

Asp Val Asn Gly His Lys Phe Ser Val Ser Gly Glu Gly Glu Gly Asp
305                 310                 315                 320

Ala Thr Tyr Gly Lys Leu Thr Leu Lys Leu Ile Cys Thr Thr Gly Lys
                325                 330                 335
```

```
Leu Pro Val Pro Trp Pro Thr Leu Val Thr Thr Leu Gly Tyr Gly Leu
            340                 345                 350

Lys Cys Phe Ala Arg Tyr Pro Asp His Met Lys Gln His Asp Phe Phe
        355                 360                 365

Lys Ser Ala Met Pro Glu Gly Tyr Val Gln Glu Arg Thr Ile Phe Phe
    370                 375                 380

Lys Asp Asp Gly Asn Tyr Lys Thr Arg Ala Glu Val Lys Phe Glu Gly
385                 390                 395                 400

Asp Thr Leu Val Asn Arg Ile Glu Leu Lys Gly Ile Gly Phe Lys Glu
                405                 410                 415

Asp Gly Asn Ile Leu Gly His Lys Leu Glu Tyr Asn Gly Lys Gly Leu
            420                 425                 430

Gly Ile Ala Val Arg Lys Asp Asn Asp Ala Leu Leu Gln Glu Ile Asn
        435                 440                 445

Ala Ala Leu Asp Lys Val Lys Ala Ser Pro Glu Tyr Ala Gln Met Gln
    450                 455                 460

Glu Lys Trp Phe Thr Gln
465                 470


<210> SEQ ID NO 27
<211> LENGTH: 473
<212> TYPE: PRT
<213> ORGANISM: Artificial Sequence
<220> FEATURE:
<223> OTHER INFORMATION: sensor

<400> SEQUENCE: 27

Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Tyr Glu Gly Leu Ser Ala Val
                85                  90                  95

Val Val Thr Arg Lys Gly Ala Tyr His Thr Phe Ala Asp Leu Lys Gly
            100                 105                 110

Lys Lys Val Gly Leu Glu Asn Gly Thr Thr His Gln Arg Tyr Leu Gln
        115                 120                 125

Asp Lys Gln Gln Ala Ile Thr Pro Val Ala Tyr Asp Ser Tyr Leu Asn
    130                 135                 140

Ala Phe Thr Asp Leu Lys Asn Asn Arg Leu Glu Gly Val Phe Gly Asp
145                 150                 155                 160

Val Ala Ala Ile Gly Lys Trp Leu Lys Asn Asn Pro Asp Tyr Ala Ile
                165                 170                 175

Met Asp Glu Arg Ala Ser Asp Tyr Asn Ser Asp Asn Val Tyr Ile Met
            180                 185                 190

Ala Asp Lys Gln Lys Asn Gly Ile Lys Ala Asn Phe Lys Ile Arg His
        195                 200                 205

Asn Val Glu Asp Gly Ser Val Gln Leu Ala Asp His Tyr Gln Gln Asn
    210                 215                 220
```

Thr Pro Ile Gly Asp Gly Pro Val Leu Leu Pro Asp Asn His Tyr Leu
225 230 235 240

Ser Phe Gln Ser Val Leu Ser Lys Asp Pro Asn Glu Lys Arg Asp His
245 250 255

Met Val Leu Leu Glu Phe Val Thr Ala Ala Gly Ile Thr Leu Gly Met
260 265 270

Asp Glu Leu Tyr Asn Val Asp Gly Gly Ser Gly Gly Thr Gly Ser Lys
275 280 285

Gly Glu Glu Leu Phe Thr Gly Val Val Pro Ile Leu Val Glu Leu Asp
290 295 300

Gly Asp Val Asn Gly His Lys Phe Ser Val Ser Gly Glu Gly Glu Gly
305 310 315 320

Asp Ala Thr Tyr Gly Lys Leu Thr Leu Lys Leu Ile Cys Thr Thr Gly
325 330 335

Lys Leu Pro Val Pro Trp Pro Thr Leu Val Thr Thr Leu Gly Tyr Gly
340 345 350

Leu Lys Cys Phe Ala Arg Tyr Pro Asp His Met Lys Gln His Asp Phe
355 360 365

Phe Lys Ser Ala Met Pro Glu Gly Tyr Val Gln Glu Arg Thr Ile Phe
370 375 380

Phe Lys Asp Asp Gly Asn Tyr Lys Thr Arg Ala Glu Val Lys Phe Glu
385 390 395 400

Gly Asp Thr Leu Val Asn Arg Ile Glu Leu Lys Gly Ile Gly Phe Lys
405 410 415

Glu Asp Gly Asn Ile Leu Gly His Lys Leu Glu Tyr Asn Tyr Tyr Gly
420 425 430

Lys Gly Leu Gly Ile Ala Val Arg Lys Asp Asn Asp Ala Leu Leu Gln
435 440 445

Glu Ile Asn Ala Ala Leu Asp Lys Val Lys Ala Ser Pro Glu Tyr Ala
450 455 460

Gln Met Gln Glu Lys Trp Phe Thr Gln
465 470

<210> SEQ ID NO 28
<211> LENGTH: 472
<212> TYPE: PRT
<213> ORGANISM: Artificial Sequence
<220> FEATURE:
<223> OTHER INFORMATION: sensor

<400> SEQUENCE: 28

Ala Ser Val Ser Ala Arg Thr Leu His Phe Gly Thr Ser Ala Thr Tyr
1 5 10 15

Ala Pro Tyr Glu Phe Val Asp Ala Asp Asn Lys Ile Val Gly Phe Asp
20 25 30

Ile Asp Val Ala Asn Ala Val Cys Lys Glu Met Gln Ala Glu Cys Ser
35 40 45

Phe Thr Asn Gln Ser Phe Asp Ser Leu Ile Pro Ser Leu Arg Phe Lys
50 55 60

Lys Phe Asp Ala Val Ile Ala Gly Met Asp Met Thr Pro Lys Arg Glu
65 70 75 80

Gln Gln Val Ser Phe Ser Gln Pro Tyr Tyr Glu Gly Leu Ser Ala Val
85 90 95

Val Val Thr Arg Lys Gly Ala Tyr His Thr Phe Ala Asp Leu Lys Gly
100 105 110

```
Lys Lys Val Gly Leu Glu Asn Gly Thr Thr His Gln Arg Tyr Leu Gln
        115                 120                 125

Asp Lys Gln Gln Ala Ile Thr Pro Val Ala Tyr Asp Ser Tyr Leu Asn
    130                 135                 140

Ala Phe Thr Asp Leu Lys Asn Asn Arg Leu Glu Gly Val Phe Gly Asp
145                 150                 155                 160

Val Ala Ala Ile Gly Lys Trp Leu Lys Asn Asn Pro Asp Tyr Ala Ile
                165                 170                 175

Met Asp Glu Arg Ala Ser Asp Tyr Asn Ser Asp Asn Val Tyr Ile Met
            180                 185                 190

Ala Asp Lys Gln Lys Asn Gly Ile Lys Ala Asn Phe Lys Ile Arg His
        195                 200                 205

Asn Val Glu Asp Gly Ser Val Gln Leu Ala Asp His Tyr Gln Gln Asn
    210                 215                 220

Thr Pro Ile Gly Asp Gly Pro Val Leu Leu Pro Asp Asn His Tyr Leu
225                 230                 235                 240

Ser Phe Gln Ser Val Leu Ser Lys Asp Pro Asn Glu Lys Arg Asp His
                245                 250                 255

Met Val Leu Leu Glu Phe Val Thr Ala Ala Gly Ile Thr Leu Gly Met
            260                 265                 270

Asp Glu Leu Tyr Asn Val Asp Gly Gly Ser Gly Gly Thr Gly Ser Lys
        275                 280                 285

Gly Glu Glu Leu Phe Thr Gly Val Val Pro Ile Leu Val Glu Leu Asp
    290                 295                 300

Gly Asp Val Asn Gly His Lys Phe Ser Val Ser Gly Glu Gly Glu Gly
305                 310                 315                 320

Asp Ala Thr Tyr Gly Lys Leu Thr Leu Lys Leu Ile Cys Thr Thr Gly
                325                 330                 335

Lys Leu Pro Val Pro Trp Pro Thr Leu Val Thr Thr Leu Gly Tyr Gly
            340                 345                 350

Leu Lys Cys Phe Ala Arg Tyr Pro Asp His Met Lys Gln His Asp Phe
        355                 360                 365

Phe Lys Ser Ala Met Pro Glu Gly Tyr Val Gln Glu Arg Thr Ile Phe
    370                 375                 380

Phe Lys Asp Asp Gly Asn Tyr Lys Thr Arg Ala Glu Val Lys Phe Glu
385                 390                 395                 400

Gly Asp Thr Leu Val Asn Arg Ile Glu Leu Lys Gly Ile Gly Phe Lys
                405                 410                 415

Glu Asp Gly Asn Ile Leu Gly His Lys Leu Glu Tyr Asn Tyr Gly Lys
            420                 425                 430

Gly Leu Gly Ile Ala Val Arg Lys Asp Asn Asp Ala Leu Leu Gln Glu
        435                 440                 445

Ile Asn Ala Ala Leu Asp Lys Val Lys Ala Ser Pro Glu Tyr Ala Gln
    450                 455                 460

Met Gln Glu Lys Trp Phe Thr Gln
465                 470
```

<210> SEQ ID NO 29
<211> LENGTH: 471
<212> TYPE: PRT
<213> ORGANISM: Artificial Sequence
<220> FEATURE:
<223> OTHER INFORMATION: sensor

<400> SEQUENCE: 29

Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Tyr Glu Gly Leu Ser Ala Val
                85                  90                  95

Val Val Thr Arg Lys Gly Ala Tyr His Thr Phe Ala Asp Leu Lys Gly
            100                 105                 110

Lys Lys Val Gly Leu Glu Asn Gly Thr Thr His Gln Arg Tyr Leu Gln
        115                 120                 125

Asp Lys Gln Gln Ala Ile Thr Pro Val Ala Tyr Asp Ser Tyr Leu Asn
    130                 135                 140

Ala Phe Thr Asp Leu Lys Asn Asn Arg Leu Glu Gly Val Phe Gly Asp
145                 150                 155                 160

Val Ala Ala Ile Gly Lys Trp Leu Lys Asn Asn Pro Asp Tyr Ala Ile
                165                 170                 175

Met Asp Glu Arg Ala Ser Asp Tyr Asn Ser Asp Asn Val Tyr Ile Met
            180                 185                 190

Ala Asp Lys Gln Lys Asn Gly Ile Lys Ala Asn Phe Lys Ile Arg His
        195                 200                 205

Asn Val Glu Asp Gly Ser Val Gln Leu Ala Asp His Tyr Gln Gln Asn
    210                 215                 220

Thr Pro Ile Gly Asp Gly Pro Val Leu Leu Pro Asp Asn His Tyr Leu
225                 230                 235                 240

Ser Phe Gln Ser Val Leu Ser Lys Asp Pro Asn Glu Lys Arg Asp His
                245                 250                 255

Met Val Leu Leu Glu Phe Val Thr Ala Ala Gly Ile Thr Leu Gly Met
            260                 265                 270

Asp Glu Leu Tyr Asn Val Asp Gly Gly Ser Gly Gly Thr Gly Ser Lys
        275                 280                 285

Gly Glu Glu Leu Phe Thr Gly Val Val Pro Ile Leu Val Glu Leu Asp
    290                 295                 300

Gly Asp Val Asn Gly His Lys Phe Ser Val Ser Gly Glu Gly Glu Gly
305                 310                 315                 320

Asp Ala Thr Tyr Gly Lys Leu Thr Leu Lys Leu Ile Cys Thr Thr Gly
                325                 330                 335

Lys Leu Pro Val Pro Trp Pro Thr Leu Val Thr Thr Leu Gly Tyr Gly
            340                 345                 350

Leu Lys Cys Phe Ala Arg Tyr Pro Asp His Met Lys Gln His Asp Phe
        355                 360                 365

Phe Lys Ser Ala Met Pro Glu Gly Tyr Val Gln Glu Arg Thr Ile Phe
    370                 375                 380

Phe Lys Asp Asp Gly Asn Tyr Lys Thr Arg Ala Glu Val Lys Phe Glu
385                 390                 395                 400

```
Gly Asp Thr Leu Val Asn Arg Ile Glu Leu Lys Gly Ile Gly Phe Lys
                405                 410                 415

Glu Asp Gly Asn Ile Leu Gly His Lys Leu Glu Tyr Asn Gly Lys Gly
            420                 425                 430

Leu Gly Ile Ala Val Arg Lys Asp Asn Asp Ala Leu Leu Gln Glu Ile
        435                 440                 445

Asn Ala Ala Leu Asp Lys Val Lys Ala Ser Pro Glu Tyr Ala Gln Met
    450                 455                 460

Gln Glu Lys Trp Phe Thr Gln
465                 470


<210> SEQ ID NO 30
<211> LENGTH: 470
<212> TYPE: PRT
<213> ORGANISM: Artificial Sequence
<220> FEATURE:
<223> OTHER INFORMATION: sensor

<400> SEQUENCE: 30

Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Tyr Glu Gly Leu Ser Ala Val
                85                  90                  95

Val Val Thr Arg Lys Gly Ala Tyr His Thr Phe Ala Asp Leu Lys Gly
            100                 105                 110

Lys Lys Val Gly Leu Glu Asn Gly Thr Thr His Gln Arg Tyr Leu Gln
        115                 120                 125

Asp Lys Gln Gln Ala Ile Thr Pro Val Ala Tyr Asp Ser Tyr Leu Asn
    130                 135                 140

Ala Phe Thr Asp Leu Lys Asn Asn Arg Leu Glu Gly Val Phe Gly Asp
145                 150                 155                 160

Val Ala Ala Ile Gly Lys Trp Leu Lys Asn Asn Pro Asp Tyr Ala Ile
                165                 170                 175

Met Asp Glu Arg Ala Ser Asp Tyr Asn Ser Asp Asn Val Tyr Ile Met
            180                 185                 190

Ala Asp Lys Gln Lys Asn Gly Ile Lys Ala Asn Phe Lys Ile Arg His
        195                 200                 205

Asn Val Glu Asp Gly Ser Val Gln Leu Ala Asp His Tyr Gln Gln Asn
    210                 215                 220

Thr Pro Ile Gly Asp Gly Pro Val Leu Leu Pro Asp Asn His Tyr Leu
225                 230                 235                 240

Ser Phe Gln Ser Val Leu Ser Lys Asp Pro Asn Glu Lys Arg Asp His
                245                 250                 255

Met Val Leu Leu Glu Phe Val Thr Ala Ala Gly Ile Thr Leu Gly Met
            260                 265                 270

Asp Glu Leu Tyr Asn Val Asp Gly Gly Ser Gly Gly Thr Gly Ser Lys
        275                 280                 285
```

```
Gly Glu Glu Leu Phe Thr Gly Val Val Pro Ile Leu Val Glu Leu Asp
    290                 295                 300

Gly Asp Val Asn Gly His Lys Phe Ser Val Ser Gly Glu Gly Glu Gly
305                 310                 315                 320

Asp Ala Thr Tyr Gly Lys Leu Thr Leu Lys Leu Ile Cys Thr Thr Gly
                325                 330                 335

Lys Leu Pro Val Pro Trp Pro Thr Leu Val Thr Thr Leu Gly Tyr Gly
            340                 345                 350

Leu Lys Cys Phe Ala Arg Tyr Pro Asp His Met Lys Gln His Asp Phe
        355                 360                 365

Phe Lys Ser Ala Met Pro Glu Gly Tyr Val Gln Glu Arg Thr Ile Phe
    370                 375                 380

Phe Lys Asp Asp Gly Asn Tyr Lys Thr Arg Ala Glu Val Lys Phe Glu
385                 390                 395                 400

Gly Asp Thr Leu Val Asn Arg Ile Glu Leu Lys Gly Ile Gly Phe Lys
                405                 410                 415

Glu Asp Gly Asn Ile Leu Gly His Lys Leu Glu Tyr Asn Lys Gly Leu
            420                 425                 430

Gly Ile Ala Val Arg Lys Asp Asn Asp Ala Leu Leu Gln Glu Ile Asn
        435                 440                 445

Ala Ala Leu Asp Lys Val Lys Ala Ser Pro Glu Tyr Ala Gln Met Gln
    450                 455                 460

Glu Lys Trp Phe Thr Gln
465                 470
```

<210> SEQ ID NO 31
<211> LENGTH: 475
<212> TYPE: PRT
<213> ORGANISM: Artificial Sequence
<220> FEATURE:
<223> OTHER INFORMATION: sensor

<400> SEQUENCE: 31

```
Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Tyr Glu Gly Leu Ser Ala Val
                85                  90                  95

Val Val Thr Arg Lys Gly Ala Tyr His Thr Phe Ala Asp Leu Lys Gly
            100                 105                 110

Lys Lys Val Gly Leu Glu Asn Gly Thr Thr His Gln Arg Tyr Leu Gln
        115                 120                 125

Asp Lys Gln Gln Ala Ile Thr Pro Val Ala Tyr Asp Ser Tyr Leu Asn
    130                 135                 140

Ala Phe Thr Asp Leu Lys Asn Asn Arg Leu Glu Gly Val Phe Gly Asp
145                 150                 155                 160

Val Ala Ala Ile Gly Lys Trp Leu Lys Asn Asn Pro Asp Tyr Ala Ile
                165                 170                 175
```

```
Met Asp Glu Arg Ala Ser Asp Pro Tyr Asn Ser Asp Asn Val Tyr Ile
            180                 185                 190

Met Ala Asp Lys Gln Lys Asn Gly Ile Lys Ala Asn Phe Lys Ile Arg
        195                 200                 205

His Asn Val Glu Asp Gly Ser Val Gln Leu Ala Asp His Tyr Gln Gln
    210                 215                 220

Asn Thr Pro Ile Gly Asp Gly Pro Val Leu Leu Pro Asp Asn His Tyr
225                 230                 235                 240

Leu Ser Phe Gln Ser Val Leu Ser Lys Asp Pro Asn Glu Lys Arg Asp
                245                 250                 255

His Met Val Leu Leu Glu Phe Val Thr Ala Ala Gly Ile Thr Leu Gly
            260                 265                 270

Met Asp Glu Leu Tyr Asn Val Asp Gly Gly Ser Gly Gly Thr Gly Ser
        275                 280                 285

Lys Gly Glu Glu Leu Phe Thr Gly Val Val Pro Ile Leu Val Glu Leu
    290                 295                 300

Asp Gly Asp Val Asn Gly His Lys Phe Ser Val Ser Gly Glu Gly Glu
305                 310                 315                 320

Gly Asp Ala Thr Tyr Gly Lys Leu Thr Leu Lys Leu Ile Cys Thr Thr
                325                 330                 335

Gly Lys Leu Pro Val Pro Trp Pro Thr Leu Val Thr Thr Leu Gly Tyr
            340                 345                 350

Gly Leu Lys Cys Phe Ala Arg Tyr Pro Asp His Met Lys Gln His Asp
        355                 360                 365

Phe Phe Lys Ser Ala Met Pro Glu Gly Tyr Val Gln Glu Arg Thr Ile
    370                 375                 380

Phe Phe Lys Asp Asp Gly Asn Tyr Lys Thr Arg Ala Glu Val Lys Phe
385                 390                 395                 400

Glu Gly Asp Thr Leu Val Asn Arg Ile Glu Leu Lys Gly Ile Gly Phe
                405                 410                 415

Lys Glu Asp Gly Asn Ile Leu Gly His Lys Leu Glu Tyr Asn Asp Tyr
            420                 425                 430

Tyr Gly Lys Gly Leu Gly Ile Ala Val Arg Lys Asp Asn Asp Ala Leu
        435                 440                 445

Leu Gln Glu Ile Asn Ala Ala Leu Asp Lys Val Lys Ala Ser Pro Glu
    450                 455                 460

Tyr Ala Gln Met Gln Glu Lys Trp Phe Thr Gln
465                 470                 475
```

<210> SEQ ID NO 32
<211> LENGTH: 474
<212> TYPE: PRT
<213> ORGANISM: Artificial Sequence
<220> FEATURE:
<223> OTHER INFORMATION: sensor

<400> SEQUENCE: 32

```
Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60
```

```
Lys Phe Asp Ala Val Ile Ala Gly Met Asp Met Thr Pro Lys Arg Glu
65                  70                  75                  80

Gln Gln Val Ser Phe Ser Gln Pro Tyr Tyr Glu Gly Leu Ser Ala Val
                85                  90                  95

Val Val Thr Arg Lys Gly Ala Tyr His Thr Phe Ala Asp Leu Lys Gly
            100                 105                 110

Lys Lys Val Gly Leu Glu Asn Gly Thr Thr His Gln Arg Tyr Leu Gln
        115                 120                 125

Asp Lys Gln Gln Ala Ile Thr Pro Val Ala Tyr Asp Ser Tyr Leu Asn
    130                 135                 140

Ala Phe Thr Asp Leu Lys Asn Asn Arg Leu Glu Gly Val Phe Gly Asp
145                 150                 155                 160

Val Ala Ala Ile Gly Lys Trp Leu Lys Asn Asn Pro Asp Tyr Ala Ile
                165                 170                 175

Met Asp Glu Arg Ala Ser Asp Pro Tyr Asn Ser Asp Asn Val Tyr Ile
            180                 185                 190

Met Ala Asp Lys Gln Lys Asn Gly Ile Lys Ala Asn Phe Lys Ile Arg
        195                 200                 205

His Asn Val Glu Asp Gly Ser Val Gln Leu Ala Asp His Tyr Gln Gln
    210                 215                 220

Asn Thr Pro Ile Gly Asp Gly Pro Val Leu Leu Pro Asp Asn His Tyr
225                 230                 235                 240

Leu Ser Phe Gln Ser Val Leu Ser Lys Asp Pro Asn Glu Lys Arg Asp
                245                 250                 255

His Met Val Leu Leu Glu Phe Val Thr Ala Ala Gly Ile Thr Leu Gly
            260                 265                 270

Met Asp Glu Leu Tyr Asn Val Asp Gly Gly Ser Gly Gly Thr Gly Ser
        275                 280                 285

Lys Gly Glu Glu Leu Phe Thr Gly Val Val Pro Ile Leu Val Glu Leu
    290                 295                 300

Asp Gly Asp Val Asn Gly His Lys Phe Ser Val Ser Gly Glu Gly Glu
305                 310                 315                 320

Gly Asp Ala Thr Tyr Gly Lys Leu Thr Leu Lys Leu Ile Cys Thr Thr
                325                 330                 335

Gly Lys Leu Pro Val Pro Trp Pro Thr Leu Val Thr Thr Leu Gly Tyr
            340                 345                 350

Gly Leu Lys Cys Phe Ala Arg Tyr Pro Asp His Met Lys Gln His Asp
        355                 360                 365

Phe Phe Lys Ser Ala Met Pro Glu Gly Tyr Val Gln Glu Arg Thr Ile
    370                 375                 380

Phe Phe Lys Asp Asp Gly Asn Tyr Lys Thr Arg Ala Glu Val Lys Phe
385                 390                 395                 400

Glu Gly Asp Thr Leu Val Asn Arg Ile Glu Leu Lys Gly Ile Gly Phe
                405                 410                 415

Lys Glu Asp Gly Asn Ile Leu Gly His Lys Leu Glu Tyr Asn Tyr Tyr
            420                 425                 430

Gly Lys Gly Leu Gly Ile Ala Val Arg Lys Asp Asn Asp Ala Leu Leu
        435                 440                 445

Gln Glu Ile Asn Ala Ala Leu Asp Lys Val Lys Ala Ser Pro Glu Tyr
    450                 455                 460

Ala Gln Met Gln Glu Lys Trp Phe Thr Gln
465                 470
```

<210> SEQ ID NO 33
<211> LENGTH: 473
<212> TYPE: PRT
<213> ORGANISM: Artificial Sequence
<220> FEATURE:
<223> OTHER INFORMATION: sensor

<400> SEQUENCE: 33

Ala Ser Val Ser Ala Arg Thr Leu His Phe Gly Thr Ser Ala Thr Tyr
1 5 10 15

Ala Pro Tyr Glu Phe Val Asp Ala Asp Asn Lys Ile Val Gly Phe Asp
20 25 30

Ile Asp Val Ala Asn Ala Val Cys Lys Glu Met Gln Ala Glu Cys Ser
35 40 45

Phe Thr Asn Gln Ser Phe Asp Ser Leu Ile Pro Ser Leu Arg Phe Lys
50 55 60

Lys Phe Asp Ala Val Ile Ala Gly Met Asp Met Thr Pro Lys Arg Glu
65 70 75 80

Gln Gln Val Ser Phe Ser Gln Pro Tyr Tyr Glu Gly Leu Ser Ala Val
85 90 95

Val Val Thr Arg Lys Gly Ala Tyr His Thr Phe Ala Asp Leu Lys Gly
100 105 110

Lys Lys Val Gly Leu Glu Asn Gly Thr Thr His Gln Arg Tyr Leu Gln
115 120 125

Asp Lys Gln Gln Ala Ile Thr Pro Val Ala Tyr Asp Ser Tyr Leu Asn
130 135 140

Ala Phe Thr Asp Leu Lys Asn Asn Arg Leu Glu Gly Val Phe Gly Asp
145 150 155 160

Val Ala Ala Ile Gly Lys Trp Leu Lys Asn Asn Pro Asp Tyr Ala Ile
165 170 175

Met Asp Glu Arg Ala Ser Asp Pro Tyr Asn Ser Asp Asn Val Tyr Ile
180 185 190

Met Ala Asp Lys Gln Lys Asn Gly Ile Lys Ala Asn Phe Lys Ile Arg
195 200 205

His Asn Val Glu Asp Gly Ser Val Gln Leu Ala Asp His Tyr Gln Gln
210 215 220

Asn Thr Pro Ile Gly Asp Gly Pro Val Leu Leu Pro Asp Asn His Tyr
225 230 235 240

Leu Ser Phe Gln Ser Val Leu Ser Lys Asp Pro Asn Glu Lys Arg Asp
245 250 255

His Met Val Leu Leu Glu Phe Val Thr Ala Ala Gly Ile Thr Leu Gly
260 265 270

Met Asp Glu Leu Tyr Asn Val Asp Gly Gly Ser Gly Gly Thr Gly Ser
275 280 285

Lys Gly Glu Glu Leu Phe Thr Gly Val Val Pro Ile Leu Val Glu Leu
290 295 300

Asp Gly Asp Val Asn Gly His Lys Phe Ser Val Ser Gly Glu Gly Glu
305 310 315 320

Gly Asp Ala Thr Tyr Gly Lys Leu Thr Leu Lys Leu Ile Cys Thr Thr
325 330 335

Gly Lys Leu Pro Val Pro Trp Pro Thr Leu Val Thr Thr Leu Gly Tyr
340 345 350

Gly Leu Lys Cys Phe Ala Arg Tyr Pro Asp His Met Lys Gln His Asp
355 360 365

```
Phe Phe Lys Ser Ala Met Pro Glu Gly Tyr Val Gln Glu Arg Thr Ile
    370                 375                 380

Phe Phe Lys Asp Asp Gly Asn Tyr Lys Thr Arg Ala Glu Val Lys Phe
385                 390                 395                 400

Glu Gly Asp Thr Leu Val Asn Arg Ile Glu Leu Lys Gly Ile Gly Phe
                405                 410                 415

Lys Glu Asp Gly Asn Ile Leu Gly His Lys Leu Glu Tyr Asn Tyr Gly
            420                 425                 430

Lys Gly Leu Gly Ile Ala Val Arg Lys Asp Asn Asp Ala Leu Leu Gln
        435                 440                 445

Glu Ile Asn Ala Ala Leu Asp Lys Val Lys Ala Ser Pro Glu Tyr Ala
    450                 455                 460

Gln Met Gln Glu Lys Trp Phe Thr Gln
465                 470


<210> SEQ ID NO 34
<211> LENGTH: 472
<212> TYPE: PRT
<213> ORGANISM: Artificial Sequence
<220> FEATURE:
<223> OTHER INFORMATION: sensor

<400> SEQUENCE: 34

Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Tyr Glu Gly Leu Ser Ala Val
                85                  90                  95

Val Val Thr Arg Lys Gly Ala Tyr His Thr Phe Ala Asp Leu Lys Gly
            100                 105                 110

Lys Lys Val Gly Leu Glu Asn Gly Thr Thr His Gln Arg Tyr Leu Gln
        115                 120                 125

Asp Lys Gln Gln Ala Ile Thr Pro Val Ala Tyr Asp Ser Tyr Leu Asn
    130                 135                 140

Ala Phe Thr Asp Leu Lys Asn Asn Arg Leu Glu Gly Val Phe Gly Asp
145                 150                 155                 160

Val Ala Ala Ile Gly Lys Trp Leu Lys Asn Asn Pro Asp Tyr Ala Ile
                165                 170                 175

Met Asp Glu Arg Ala Ser Asp Pro Tyr Asn Ser Asp Asn Val Tyr Ile
            180                 185                 190

Met Ala Asp Lys Gln Lys Asn Gly Ile Lys Ala Asn Phe Lys Ile Arg
        195                 200                 205

His Asn Val Glu Asp Gly Ser Val Gln Leu Ala Asp His Tyr Gln Gln
    210                 215                 220

Asn Thr Pro Ile Gly Asp Gly Pro Val Leu Leu Pro Asp Asn His Tyr
225                 230                 235                 240

Leu Ser Phe Gln Ser Val Leu Ser Lys Asp Pro Asn Glu Lys Arg Asp
                245                 250                 255
```

His Met Val Leu Leu Glu Phe Val Thr Ala Ala Gly Ile Thr Leu Gly
260 265 270

Met Asp Glu Leu Tyr Asn Val Asp Gly Gly Ser Gly Gly Thr Gly Ser
275 280 285

Lys Gly Glu Glu Leu Phe Thr Gly Val Val Pro Ile Leu Val Glu Leu
290 295 300

Asp Gly Asp Val Asn Gly His Lys Phe Ser Val Ser Gly Glu Gly Glu
305 310 315 320

Gly Asp Ala Thr Tyr Gly Lys Leu Thr Leu Lys Leu Ile Cys Thr Thr
325 330 335

Gly Lys Leu Pro Val Pro Trp Pro Thr Leu Val Thr Thr Leu Gly Tyr
340 345 350

Gly Leu Lys Cys Phe Ala Arg Tyr Pro Asp His Met Lys Gln His Asp
355 360 365

Phe Phe Lys Ser Ala Met Pro Glu Gly Tyr Val Gln Glu Arg Thr Ile
370 375 380

Phe Phe Lys Asp Asp Gly Asn Tyr Lys Thr Arg Ala Glu Val Lys Phe
385 390 395 400

Glu Gly Asp Thr Leu Val Asn Arg Ile Glu Leu Lys Gly Ile Gly Phe
405 410 415

Lys Glu Asp Gly Asn Ile Leu Gly His Lys Leu Glu Tyr Asn Gly Lys
420 425 430

Gly Leu Gly Ile Ala Val Arg Lys Asp Asn Asp Ala Leu Leu Gln Glu
435 440 445

Ile Asn Ala Ala Leu Asp Lys Val Lys Ala Ser Pro Glu Tyr Ala Gln
450 455 460

Met Gln Glu Lys Trp Phe Thr Gln
465 470

<210> SEQ ID NO 35
<211> LENGTH: 471
<212> TYPE: PRT
<213> ORGANISM: Artificial Sequence
<220> FEATURE:
<223> OTHER INFORMATION: sensor

<400> SEQUENCE: 35

Ala Ser Val Ser Ala Arg Thr Leu His Phe Gly Thr Ser Ala Thr Tyr
1 5 10 15

Ala Pro Tyr Glu Phe Val Asp Ala Asp Asn Lys Ile Val Gly Phe Asp
20 25 30

Ile Asp Val Ala Asn Ala Val Cys Lys Glu Met Gln Ala Glu Cys Ser
35 40 45

Phe Thr Asn Gln Ser Phe Asp Ser Leu Ile Pro Ser Leu Arg Phe Lys
50 55 60

Lys Phe Asp Ala Val Ile Ala Gly Met Asp Met Thr Pro Lys Arg Glu
65 70 75 80

Gln Gln Val Ser Phe Ser Gln Pro Tyr Tyr Glu Gly Leu Ser Ala Val
85 90 95

Val Val Thr Arg Lys Gly Ala Tyr His Thr Phe Ala Asp Leu Lys Gly
100 105 110

Lys Lys Val Gly Leu Glu Asn Gly Thr Thr His Gln Arg Tyr Leu Gln
115 120 125

Asp Lys Gln Gln Ala Ile Thr Pro Val Ala Tyr Asp Ser Tyr Leu Asn
130 135 140

Ala Phe Thr Asp Leu Lys Asn Asn Arg Leu Glu Gly Val Phe Gly Asp
145 150 155 160

Val Ala Ala Ile Gly Lys Trp Leu Lys Asn Asn Pro Asp Tyr Ala Ile
165 170 175

Met Asp Glu Arg Ala Ser Asp Pro Tyr Asn Ser Asp Asn Val Tyr Ile
180 185 190

Met Ala Asp Lys Gln Lys Asn Gly Ile Lys Ala Asn Phe Lys Ile Arg
195 200 205

His Asn Val Glu Asp Gly Ser Val Gln Leu Ala Asp His Tyr Gln Gln
210 215 220

Asn Thr Pro Ile Gly Asp Gly Pro Val Leu Leu Pro Asp Asn His Tyr
225 230 235 240

Leu Ser Phe Gln Ser Val Leu Ser Lys Asp Pro Asn Glu Lys Arg Asp
245 250 255

His Met Val Leu Leu Glu Phe Val Thr Ala Ala Gly Ile Thr Leu Gly
260 265 270

Met Asp Glu Leu Tyr Asn Val Asp Gly Gly Ser Gly Gly Thr Gly Ser
275 280 285

Lys Gly Glu Glu Leu Phe Thr Gly Val Val Pro Ile Leu Val Glu Leu
290 295 300

Asp Gly Asp Val Asn Gly His Lys Phe Ser Val Ser Gly Glu Gly Glu
305 310 315 320

Gly Asp Ala Thr Tyr Gly Lys Leu Thr Leu Lys Leu Ile Cys Thr Thr
325 330 335

Gly Lys Leu Pro Val Pro Trp Pro Thr Leu Val Thr Thr Leu Gly Tyr
340 345 350

Gly Leu Lys Cys Phe Ala Arg Tyr Pro Asp His Met Lys Gln His Asp
355 360 365

Phe Phe Lys Ser Ala Met Pro Glu Gly Tyr Val Gln Glu Arg Thr Ile
370 375 380

Phe Phe Lys Asp Asp Gly Asn Tyr Lys Thr Arg Ala Glu Val Lys Phe
385 390 395 400

Glu Gly Asp Thr Leu Val Asn Arg Ile Glu Leu Lys Gly Ile Gly Phe
405 410 415

Lys Glu Asp Gly Asn Ile Leu Gly His Lys Leu Glu Tyr Asn Lys Gly
420 425 430

Leu Gly Ile Ala Val Arg Lys Asp Asn Asp Ala Leu Leu Gln Glu Ile
435 440 445

Asn Ala Ala Leu Asp Lys Val Lys Ala Ser Pro Glu Tyr Ala Gln Met
450 455 460

Gln Glu Lys Trp Phe Thr Gln
465 470

<210> SEQ ID NO 36
<211> LENGTH: 473
<212> TYPE: PRT
<213> ORGANISM: Artificial Sequence
<220> FEATURE:
<223> OTHER INFORMATION: sensor

<400> SEQUENCE: 36

Ala Ser Val Ser Ala Arg Thr Leu His Phe Gly Thr Ser Ala Thr Tyr
1 5 10 15

Ala Pro Tyr Glu Phe Val Asp Ala Asp Asn Lys Ile Val Gly Phe Asp
20 25 30

-continued

```
Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Tyr Glu Gly Leu Ser Ala Val
                85                  90                  95

Val Val Thr Arg Lys Gly Ala Tyr His Thr Phe Ala Asp Leu Lys Gly
            100                 105                 110

Lys Lys Val Gly Leu Glu Asn Gly Thr Thr His Gln Arg Tyr Leu Gln
        115                 120                 125

Asp Lys Gln Gln Ala Ile Thr Pro Val Ala Tyr Asp Ser Tyr Leu Asn
    130                 135                 140

Ala Phe Thr Asp Leu Lys Asn Asn Arg Leu Glu Gly Val Phe Gly Asp
145                 150                 155                 160

Val Ala Ala Ile Gly Lys Trp Leu Lys Asn Asn Pro Asp Tyr Ala Ile
                165                 170                 175

Met Asp Glu Arg Ala Ser Asp Pro Asp Tyr Asn Ser Asp Asn Val Tyr
            180                 185                 190

Ile Met Ala Asp Lys Gln Lys Asn Gly Ile Lys Ala Asn Phe Lys Ile
        195                 200                 205

Arg His Asn Val Glu Asp Gly Ser Val Gln Leu Ala Asp His Tyr Gln
    210                 215                 220

Gln Asn Thr Pro Ile Gly Asp Gly Pro Val Leu Leu Pro Asp Asn His
225                 230                 235                 240

Tyr Leu Ser Phe Gln Ser Val Leu Ser Lys Asp Pro Asn Glu Lys Arg
                245                 250                 255

Asp His Met Val Leu Leu Glu Phe Val Thr Ala Ala Gly Ile Thr Leu
            260                 265                 270

Gly Met Asp Glu Leu Tyr Asn Val Asp Gly Gly Ser Gly Gly Thr Gly
        275                 280                 285

Ser Lys Gly Glu Glu Leu Phe Thr Gly Val Val Pro Ile Leu Val Glu
    290                 295                 300

Leu Asp Gly Asp Val Asn Gly His Lys Phe Ser Val Ser Gly Glu Gly
305                 310                 315                 320

Glu Gly Asp Ala Thr Tyr Gly Lys Leu Thr Leu Lys Leu Ile Cys Thr
                325                 330                 335

Thr Gly Lys Leu Pro Val Pro Trp Pro Thr Leu Val Thr Thr Leu Gly
            340                 345                 350

Tyr Gly Leu Lys Cys Phe Ala Arg Tyr Pro Asp His Met Lys Gln His
        355                 360                 365

Asp Phe Phe Lys Ser Ala Met Pro Glu Gly Tyr Val Gln Glu Arg Thr
    370                 375                 380

Ile Phe Phe Lys Asp Asp Gly Asn Tyr Lys Thr Arg Ala Glu Val Lys
385                 390                 395                 400

Phe Glu Gly Asp Thr Leu Val Asn Arg Ile Glu Leu Lys Gly Ile Gly
                405                 410                 415

Phe Lys Glu Asp Gly Asn Ile Leu Gly His Lys Leu Glu Tyr Asn Gly
            420                 425                 430

Lys Gly Leu Gly Ile Ala Val Arg Lys Asp Asn Asp Ala Leu Leu Gln
        435                 440                 445
```

```
Glu Ile Asn Ala Ala Leu Asp Lys Val Lys Ala Ser Pro Glu Tyr Ala
    450                 455                 460

Gln Met Gln Glu Lys Trp Phe Thr Gln
465                 470


<210> SEQ ID NO 37
<211> LENGTH: 473
<212> TYPE: PRT
<213> ORGANISM: Artificial Sequence
<220> FEATURE:
<223> OTHER INFORMATION: sensor

<400> SEQUENCE: 37

Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Tyr Glu Gly Leu Ser Ala Val
                85                  90                  95

Val Val Thr Arg Lys Gly Ala Tyr His Thr Phe Ala Asp Leu Lys Gly
            100                 105                 110

Lys Lys Val Gly Leu Glu Asn Gly Thr Thr His Gln Arg Tyr Leu Gln
        115                 120                 125

Asp Lys Gln Gln Ala Ile Thr Pro Val Ala Tyr Asp Ser Tyr Leu Asn
    130                 135                 140

Ala Phe Thr Asp Leu Lys Asn Asn Arg Leu Glu Gly Val Phe Gly Asp
145                 150                 155                 160

Val Ala Ala Ile Gly Lys Trp Leu Lys Asn Asn Pro Asp Tyr Ala Ile
                165                 170                 175

Met Asp Glu Arg Ala Ser Asp Pro Asp Tyr Tyr Asn Ser Asp Asn Val
            180                 185                 190

Tyr Ile Met Ala Asp Lys Gln Lys Asn Gly Ile Lys Ala Asn Phe Lys
        195                 200                 205

Ile Arg His Asn Val Glu Asp Gly Ser Val Gln Leu Ala Asp His Tyr
    210                 215                 220

Gln Gln Asn Thr Pro Ile Gly Asp Gly Pro Val Leu Leu Pro Asp Asn
225                 230                 235                 240

His Tyr Leu Ser Phe Gln Ser Val Leu Ser Lys Asp Pro Asn Glu Lys
                245                 250                 255

Arg Asp His Met Val Leu Leu Glu Phe Val Thr Ala Ala Gly Ile Thr
            260                 265                 270

Leu Gly Met Asp Glu Leu Tyr Asn Val Asp Gly Gly Ser Gly Gly Thr
        275                 280                 285

Gly Ser Lys Gly Glu Glu Leu Phe Thr Gly Val Val Pro Ile Leu Val
    290                 295                 300

Glu Leu Asp Gly Asp Val Asn Gly His Lys Phe Ser Val Ser Gly Glu
305                 310                 315                 320

Gly Glu Gly Asp Ala Thr Tyr Gly Lys Leu Thr Leu Lys Leu Ile Cys
                325                 330                 335
```

Thr Thr Gly Lys Leu Pro Val Pro Trp Pro Thr Leu Val Thr Thr Leu
340 345 350

Gly Tyr Gly Leu Lys Cys Phe Ala Arg Tyr Pro Asp His Met Lys Gln
355 360 365

His Asp Phe Phe Lys Ser Ala Met Pro Glu Gly Tyr Val Gln Glu Arg
370 375 380

Thr Ile Phe Phe Lys Asp Asp Gly Asn Tyr Lys Thr Arg Ala Glu Val
385 390 395 400

Lys Phe Glu Gly Asp Thr Leu Val Asn Arg Ile Glu Leu Lys Gly Ile
405 410 415

Gly Phe Lys Glu Asp Gly Asn Ile Leu Gly His Lys Leu Glu Tyr Asn
420 425 430

Lys Gly Leu Gly Ile Ala Val Arg Lys Asp Asn Asp Ala Leu Leu Gln
435 440 445

Glu Ile Asn Ala Ala Leu Asp Lys Val Lys Ala Ser Pro Glu Tyr Ala
450 455 460

Gln Met Gln Glu Lys Trp Phe Thr Gln
465 470

<210> SEQ ID NO 38
<211> LENGTH: 475
<212> TYPE: PRT
<213> ORGANISM: Artificial Sequence
<220> FEATURE:
<223> OTHER INFORMATION: sensor

<400> SEQUENCE: 38

Ala Ser Val Ser Ala Arg Thr Leu His Phe Gly Thr Ser Ala Thr Tyr
1 5 10 15

Ala Pro Tyr Glu Phe Val Asp Ala Asp Asn Lys Ile Val Gly Phe Asp
20 25 30

Ile Asp Val Ala Asn Ala Val Cys Lys Glu Met Gln Ala Glu Cys Ser
35 40 45

Phe Thr Asn Gln Ser Phe Asp Ser Leu Ile Pro Ser Leu Arg Phe Lys
50 55 60

Lys Phe Asp Ala Val Ile Ala Gly Met Asp Met Thr Pro Lys Arg Glu
65 70 75 80

Gln Gln Val Ser Phe Ser Gln Pro Tyr Tyr Glu Gly Leu Ser Ala Val
85 90 95

Val Val Thr Arg Lys Gly Ala Tyr His Thr Phe Ala Asp Leu Lys Gly
100 105 110

Lys Lys Val Gly Leu Glu Asn Gly Thr Thr His Gln Arg Tyr Leu Gln
115 120 125

Asp Lys Gln Gln Ala Ile Thr Pro Val Ala Tyr Asp Ser Tyr Leu Asn
130 135 140

Ala Phe Thr Asp Leu Lys Asn Asn Arg Leu Glu Gly Val Phe Gly Asp
145 150 155 160

Val Ala Ala Ile Gly Lys Trp Leu Lys Asn Asn Pro Asp Tyr Ala Ile
165 170 175

Met Asp Glu Arg Ala Ser Asp Pro Asp Tyr Tyr Tyr Asn Ser Asp Asn
180 185 190

Val Tyr Ile Met Ala Asp Lys Gln Lys Asn Gly Ile Lys Ala Asn Phe
195 200 205

Lys Ile Arg His Asn Val Glu Asp Gly Ser Val Gln Leu Ala Asp His
210 215 220

```
Tyr Gln Gln Asn Thr Pro Ile Gly Asp Gly Pro Val Leu Leu Pro Asp
225                 230                 235                 240

Asn His Tyr Leu Ser Phe Gln Ser Val Leu Ser Lys Asp Pro Asn Glu
                245                 250                 255

Lys Arg Asp His Met Val Leu Leu Glu Phe Val Thr Ala Ala Gly Ile
            260                 265                 270

Thr Leu Gly Met Asp Glu Leu Tyr Asn Val Asp Gly Gly Ser Gly Gly
        275                 280                 285

Thr Gly Ser Lys Gly Glu Glu Leu Phe Thr Gly Val Val Pro Ile Leu
    290                 295                 300

Val Glu Leu Asp Gly Asp Val Asn Gly His Lys Phe Ser Val Ser Gly
305                 310                 315                 320

Glu Gly Glu Gly Asp Ala Thr Tyr Gly Lys Leu Thr Leu Lys Leu Ile
                325                 330                 335

Cys Thr Thr Gly Lys Leu Pro Val Pro Trp Pro Thr Leu Val Thr Thr
            340                 345                 350

Leu Gly Tyr Gly Leu Lys Cys Phe Ala Arg Tyr Pro Asp His Met Lys
        355                 360                 365

Gln His Asp Phe Phe Lys Ser Ala Met Pro Glu Gly Tyr Val Gln Glu
    370                 375                 380

Arg Thr Ile Phe Phe Lys Asp Asp Gly Asn Tyr Lys Thr Arg Ala Glu
385                 390                 395                 400

Val Lys Phe Glu Gly Asp Thr Leu Val Asn Arg Ile Glu Leu Lys Gly
                405                 410                 415

Ile Gly Phe Lys Glu Asp Gly Asn Ile Leu Gly His Lys Leu Glu Tyr
            420                 425                 430

Asn Gly Lys Gly Leu Gly Ile Ala Val Arg Lys Asp Asn Asp Ala Leu
        435                 440                 445

Leu Gln Glu Ile Asn Ala Ala Leu Asp Lys Val Lys Ala Ser Pro Glu
    450                 455                 460

Tyr Ala Gln Met Gln Glu Lys Trp Phe Thr Gln
465                 470                 475


<210> SEQ ID NO 39
<211> LENGTH: 474
<212> TYPE: PRT
<213> ORGANISM: Artificial Sequence
<220> FEATURE:
<223> OTHER INFORMATION: sensor

<400> SEQUENCE: 39

Ala Ser Val Ser Ala Arg Thr Leu His Phe Gly Thr Ser Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Tyr Glu Gly Leu Ser Ala Val
                85                  90                  95

Val Val Thr Arg Lys Gly Ala Tyr His Thr Phe Ala Asp Leu Lys Gly
            100                 105                 110
```

```
Lys Lys Val Gly Leu Glu Asn Gly Thr Thr His Gln Arg Tyr Leu Gln
        115                 120                 125

Asp Lys Gln Gln Ala Ile Thr Pro Val Ala Tyr Asp Ser Tyr Leu Asn
    130                 135                 140

Ala Phe Thr Asp Leu Lys Asn Asn Arg Leu Glu Gly Val Phe Gly Asp
145                 150                 155                 160

Val Ala Ala Ile Gly Lys Trp Leu Lys Asn Asn Pro Asp Tyr Ala Ile
                165                 170                 175

Met Asp Glu Arg Ala Ser Asp Pro Asp Tyr Tyr Tyr Asn Ser Asp Asn
            180                 185                 190

Val Tyr Ile Met Ala Asp Lys Gln Lys Asn Gly Ile Lys Ala Asn Phe
        195                 200                 205

Lys Ile Arg His Asn Val Glu Asp Gly Ser Val Gln Leu Ala Asp His
    210                 215                 220

Tyr Gln Gln Asn Thr Pro Ile Gly Asp Gly Pro Val Leu Leu Pro Asp
225                 230                 235                 240

Asn His Tyr Leu Ser Phe Gln Ser Val Leu Ser Lys Asp Pro Asn Glu
                245                 250                 255

Lys Arg Asp His Met Val Leu Leu Glu Phe Val Thr Ala Ala Gly Ile
            260                 265                 270

Thr Leu Gly Met Asp Glu Leu Tyr Asn Val Asp Gly Gly Ser Gly Gly
        275                 280                 285

Thr Gly Ser Lys Gly Glu Glu Leu Phe Thr Gly Val Val Pro Ile Leu
    290                 295                 300

Val Glu Leu Asp Gly Asp Val Asn Gly His Lys Phe Ser Val Ser Gly
305                 310                 315                 320

Glu Gly Glu Gly Asp Ala Thr Tyr Gly Lys Leu Thr Leu Lys Leu Ile
                325                 330                 335

Cys Thr Thr Gly Lys Leu Pro Val Pro Trp Pro Thr Leu Val Thr Thr
            340                 345                 350

Leu Gly Tyr Gly Leu Lys Cys Phe Ala Arg Tyr Pro Asp His Met Lys
        355                 360                 365

Gln His Asp Phe Phe Lys Ser Ala Met Pro Glu Gly Tyr Val Gln Glu
    370                 375                 380

Arg Thr Ile Phe Phe Lys Asp Asp Gly Asn Tyr Lys Thr Arg Ala Glu
385                 390                 395                 400

Val Lys Phe Glu Gly Asp Thr Leu Val Asn Arg Ile Glu Leu Lys Gly
                405                 410                 415

Ile Gly Phe Lys Glu Asp Gly Asn Ile Leu Gly His Lys Leu Glu Tyr
            420                 425                 430

Asn Lys Gly Leu Gly Ile Ala Val Arg Lys Asp Asn Asp Ala Leu Leu
        435                 440                 445

Gln Glu Ile Asn Ala Ala Leu Asp Lys Val Lys Ala Ser Pro Glu Tyr
    450                 455                 460

Ala Gln Met Gln Glu Lys Trp Phe Thr Gln
465                 470
```

<210> SEQ ID NO 40
<211> LENGTH: 472
<212> TYPE: PRT
<213> ORGANISM: Artificial Sequence
<220> FEATURE:
<223> OTHER INFORMATION: sensor

<400> SEQUENCE: 40

```
Ala Ser Val Ser Ala Arg Thr Leu His Phe Gly Thr Asn Ala Thr Tyr
1               5                   10                  15

Ala Pro Tyr Glu Phe Val Asp Ala Asp Asn Lys Ile Val Gly Phe Asp
            20                  25                  30

Ile Asp Val Ala Asn Ala Val Cys Lys Glu Met Gln Ala Glu Cys Ser
        35                  40                  45

Phe Thr Asn Gln Ser Phe Asp Ser Leu Ile Pro Ser Leu Arg Phe Lys
    50                  55                  60

Lys Phe Asp Ala Val Ile Ala Gly Met Asp Met Thr Pro Lys Arg Glu
65                  70                  75                  80

Gln Gln Val Ser Phe Ser Gln Pro Tyr Tyr Tyr Asn Ser Asp Asn Val
                85                  90                  95

Tyr Ile Met Ala Asp Lys Gln Lys Asn Gly Ile Lys Ala Asn Phe Lys
            100                 105                 110

Ile Arg His Asn Val Glu Asp Gly Ser Val Gln Leu Ala Asp His Tyr
        115                 120                 125

Gln Gln Asn Thr Pro Ile Gly Asp Gly Pro Val Leu Leu Pro Asp Asn
    130                 135                 140

His Tyr Leu Ser Phe Gln Ser Val Leu Ser Lys Asp Pro Asn Glu Lys
145                 150                 155                 160

Arg Asp His Met Val Leu Leu Glu Phe Val Thr Ala Ala Gly Ile Thr
                165                 170                 175

Leu Gly Met Asp Glu Leu Tyr Asn Val Asp Gly Gly Ser Gly Gly Thr
            180                 185                 190

Gly Ser Lys Gly Glu Glu Leu Phe Thr Gly Val Val Pro Ile Leu Val
        195                 200                 205

Glu Leu Asp Gly Asp Val Asn Gly His Lys Phe Ser Val Ser Gly Glu
    210                 215                 220

Gly Glu Gly Asp Ala Thr Tyr Gly Lys Leu Thr Leu Lys Leu Ile Cys
225                 230                 235                 240

Thr Thr Gly Lys Leu Pro Val Pro Trp Pro Thr Leu Val Thr Thr Leu
                245                 250                 255

Gly Tyr Gly Leu Lys Cys Phe Ala Arg Tyr Pro Asp His Met Lys Gln
            260                 265                 270

His Asp Phe Phe Lys Ser Ala Met Pro Glu Gly Tyr Val Gln Glu Arg
        275                 280                 285

Thr Ile Phe Phe Lys Asp Asp Gly Asn Tyr Lys Thr Arg Ala Glu Val
    290                 295                 300

Lys Phe Glu Gly Asp Thr Leu Val Asn Arg Ile Glu Leu Lys Gly Ile
305                 310                 315                 320

Gly Phe Lys Glu Asp Gly Asn Ile Leu Gly His Lys Leu Glu Tyr Asn
                325                 330                 335

Ser Ala Val Val Val Thr Arg Lys Gly Ala Tyr His Thr Phe Ala Asp
            340                 345                 350

Leu Lys Gly Lys Lys Val Gly Leu Glu Asn Gly Thr Thr His Gln Arg
        355                 360                 365

Tyr Leu Gln Asp Lys Gln Gln Ala Ile Thr Pro Val Ala Tyr Asp Ser
    370                 375                 380

Tyr Leu Asn Ala Phe Thr Asp Leu Lys Asn Asn Arg Leu Glu Gly Val
385                 390                 395                 400
```

Phe Gly Asp Val Ala Ala Ile Gly Lys Trp Leu Lys Asn Asn Pro Asp
405 410 415

Tyr Ala Ile Met Asp Glu Arg Ala Ser Asp Pro Asp Tyr Tyr Gly Lys
420 425 430

Gly Leu Gly Ile Ala Val Arg Lys Asp Asn Asp Ala Leu Leu Gln Glu
435 440 445

Ile Asn Ala Ala Leu Asp Lys Val Lys Ala Ser Pro Glu Tyr Ala Gln
450 455 460

Met Gln Glu Lys Trp Phe Thr Gln
465 470

<210> SEQ ID NO 41
<211> LENGTH: 472
<212> TYPE: PRT
<213> ORGANISM: Artificial Sequence
<220> FEATURE:
<223> OTHER INFORMATION: sensor

<400> SEQUENCE: 41

Ala Ser Val Ser Ala Arg Thr Leu His Phe Gly Thr Ser Ala Thr Tyr
1 5 10 15

Ala Pro Tyr Glu Phe Val Asp Ala Asp Asn Lys Ile Val Gly Phe Asp
20 25 30

Ile Asp Val Ala Asn Ala Val Cys Lys Glu Met Gln Ala Glu Cys Ser
35 40 45

Phe Thr Asn Gln Ser Phe Asp Ser Leu Ile Pro Ser Leu Arg Phe Lys
50 55 60

Lys Phe Asp Ala Val Ile Ala Gly Met Asp Met Thr Pro Lys Arg Glu
65 70 75 80

Gln Gln Val Ser Phe Ser Gln Pro Tyr Tyr Tyr Asn Ser Asp Asn Val
85 90 95

Tyr Ile Met Ala Asp Lys Gln Lys Asn Gly Ile Lys Ala Asn Phe Lys
100 105 110

Ile Arg His Asn Val Glu Asp Gly Ser Val Gln Leu Ala Asp His Tyr
115 120 125

Gln Gln Asn Thr Pro Ile Gly Asp Gly Pro Val Leu Leu Pro Asp Asn
130 135 140

His Tyr Leu Ser Phe Gln Ser Val Leu Ser Lys Asp Pro Asn Glu Lys
145 150 155 160

Arg Asp His Met Val Leu Leu Glu Phe Val Thr Ala Ala Gly Ile Thr
165 170 175

Leu Gly Met Asp Glu Leu Tyr Asn Val Asp Gly Gly Ser Gly Gly Thr
180 185 190

Gly Ser Lys Gly Glu Glu Leu Phe Thr Gly Val Val Pro Ile Leu Val
195 200 205

Glu Leu Asp Gly Asp Val Asn Gly His Lys Phe Ser Val Ser Gly Glu
210 215 220

Gly Glu Gly Asp Ala Thr Tyr Gly Lys Leu Thr Leu Lys Leu Ile Cys
225 230 235 240

Thr Thr Gly Lys Leu Pro Val Pro Trp Pro Thr Leu Val Thr Thr Leu
245 250 255

Gly Tyr Gly Leu Lys Cys Phe Ala Arg Tyr Pro Asp His Met Lys Gln
260 265 270

His Asp Phe Phe Lys Ser Ala Met Pro Glu Gly Tyr Val Gln Glu Arg
275 280 285

```
Thr Ile Phe Phe Lys Asp Asp Gly Asn Tyr Lys Thr Arg Ala Glu Val
    290                 295                 300

Lys Phe Glu Gly Asp Thr Leu Val Asn Arg Ile Glu Leu Lys Gly Ile
305                 310                 315                 320

Gly Phe Lys Glu Asp Gly Asn Ile Leu Gly His Lys Leu Glu Tyr Asn
                325                 330                 335

Ser Ala Val Val Val Thr Arg Lys Gly Ala Tyr His Thr Phe Ala Asp
            340                 345                 350

Leu Lys Gly Lys Lys Val Gly Leu Glu Asn Gly Thr Thr His Gln Arg
        355                 360                 365

Tyr Leu Gln Asp Lys Gln Gln Ala Ile Thr Pro Val Ala Tyr Asp Ser
    370                 375                 380

Tyr Leu Asn Ala Phe Thr Asp Leu Lys Asn Asn Arg Leu Glu Gly Val
385                 390                 395                 400

Phe Gly Asn Val Ala Ala Ile Gly Lys Trp Leu Lys Asn Asn Pro Asp
                405                 410                 415

Tyr Ala Ile Met Asp Glu Arg Ala Ser Asp Pro Asp Tyr Tyr Gly Lys
            420                 425                 430

Gly Leu Gly Ile Ala Val Arg Lys Asp Asn Asp Ala Leu Leu Gln Glu
        435                 440                 445

Ile Asn Ala Ala Leu Asp Lys Val Lys Ala Ser Pro Glu Tyr Ala Gln
    450                 455                 460

Met Gln Glu Lys Trp Phe Thr Gln
465                 470
```

<210> SEQ ID NO 42
<211> LENGTH: 1416
<212> TYPE: DNA
<213> ORGANISM: Artificial Sequence
<220> FEATURE:
<223> OTHER INFORMATION: sensor

<400> SEQUENCE: 42

```
gccagcgtga gcgcccgtac cctgcatttt ggcaccaatg ccacctacgc gccgtatgag      60

ttcgtggacg cggataacaa gatcgtgggt tttgacattg atgtggcgaa cgccgtgtgc     120

aaagagatgc aggctgaatg cagcttcacc aaccagagct ttgacagcct gatcccgagc     180

ctgcgtttca agaaatttga cgctgtgatt gccggcatgg atatgacccc gaagcgcgag     240

cagcaggtga gcttcagcca gccgtactat tacaacagcg acaacgtcta tatcatggcc     300

gacaagcaga agaacggcat caaggccaac ttcaagatcc gccacaacgt cgaggacggc     360

agcgtgcagc tcgccgacca ctaccagcag aacaccccca tcggcgacgg ccccgtgctg     420

ctgcccgaca accactacct gagcttccag tccgtcctga gcaaagaccc caacgagaag     480

cgcgatcaca tggtcctgct ggagttcgtg accgccgccg ggatcactct cggcatggac     540

gagctgtaca acgtggatgg cggtagcggt ggcaccggca gcaagggcga ggagctgttc     600

accggggtgg tgcccatcct ggtcgagctg gacggcgacg taaacggcca caagttcagc     660

gtgtccggcg agggcgaggg cgatgccacc tacggcaagc tgaccctgaa gctgatctgc     720

accaccggca agctgcccgt gccctggccc accctcgtga ccaccctcgg ctacggcctg     780

aagtgcttcg cccgctaccc cgaccacatg aagcagcacg acttcttcaa gtccgccatg     840

cccgaaggct acgtccagga gcgcaccatc ttcttcaagg acgacggcaa ctacaagacc     900

cgcgccgagg tgaagttcga gggcgacacc ctggtgaacc gcatcgagct gaagggcatc     960
```

-continued

| | |
|---|---|
| ggcttcaagg aggacggcaa catcctgggg cacaagctgg agtacaacag cgccgtggtg | 1020 |
| gtgacccgta agggtgccta ccacaccttt gcggacctga aaggcaagaa ggtgggcctg | 1080 |
| gagaatggca ccacccacca gcgttacctg caagataagc agcaggctat caccccggtg | 1140 |
| gcctacgaca gctatctgaa cgcgttcacc gatctgaaaa acaaccgtct ggagggcgtg | 1200 |
| ttcggcgacg tggcggccat tggcaagtgg ctgaaaaaca acccggacta cgccattatg | 1260 |
| gatgaacgtg cgagcgaccc ggattactat ggcaagggtc tgggcatcgc tgtgcgcaaa | 1320 |
| gacaacgatg ccctgctgca agaaattaac gctgccctgg ataaggtgaa agcgagcccg | 1380 |
| gagtatgctc agatgcagga aaaatggttt acccag | 1416 |

ARGININE FLUORESCENT PROBE, PREPARATION METHOD THEREFOR AND APPLICATION THEREOF

TECHNICAL FIELD

The present invention relates to the field of optical sensor technology, especially to an arginine optical sensor, preparation method therefor and application thereof.

CROSS-REFERENCE TO RELATED APPLICATION

This application is a U.S. National Stage Application, pursuant to 35 U.S.C. § 371, of PCT International Application No. PCT/CN2021/076314, filed Feb. 9, 2021, which claims priority to and the benefit of Chinese Application No. 202010098995.5, filed Feb. 18, 2020, the entire contents of each of which are incorporated herein by reference in their entirety.

SEQUENCE LISTING

This application contains a Sequence Listing which has been submitted electronically in ASCII format and is hereby incorporated by reference in its entirety. Said ASCII copy, created on Jan. 27, 2023, is named 197276_seq_EN.txt, and is 161,367 bytes in size.

BACKGROUND ART

As one of the 20 natural amino acids, arginine was originally isolated and extracted from the plant lupin seedlings by Schlus in 1886. Its molecular structure was clear and could be synthesized artificially in the early 20th century. Arginine exerts biological functions in vivo in the form of physiologically active L-arginine. Arginine is not only a component of body proteins, but also a synthetic precursor of various biologically active substances, such as polyamines and NO, and participates in biological processes such as endocrine regulation and body-specific immune regulation by stimulating the secretion of some hormones; In addition, it also acts as an intermediate of the urea cycle to relieve ammonia poisoning through the urea cycle and avoid metabolic disorders caused by excess ammonia; it plays an important role in the homogeneous metabolism of the body and can be used in a variety of metabolic pathways, including arginase, Nitric oxide synthase, arginine/glycine guanidinotransferase, arginyl-tRNA synthase, etc. Therefore, the various biological functions of arginine have attracted extensive attention of researchers and become one of the hotspots in current amino acid research.

There are two main pathways for the metabolism of arginine in mammals. First is that arginine is decomposed into ornithine and urea under the action of arginase. Ornithine is a precursor for the synthesis of polyamines, and polyamines are important for regulating cell growth and development. Second, under the action of nitric oxide synthase, arginine is decomposed into equal molecules of citrulline and NO. NO is a messenger molecule for intracellular, intercellular and neurotransmitter functions, and is widely involved in intercellular and intracellular signal transmission. In addition, arginine, glycine and methionine co-synthesized guanidinoacetic acid and phosphocreatine as amidino group donors for the amidino transfer reaction. In nervous tissue, arginine also synthesizes gamma-arginine butyric acid (Delforge J et al., Eur J Biochem. 1975, 57(1):231-239; Fernandez M L et al., J. Bacteriol. 2004, 86(18):6142-6149; Fernandez M L et al, J. Bacteriol. 2008, 190(18):3018-3025).

Arginine is one of three substrates for the formation of creatine, an important nutrient (deficiencies can lead to mental retardation) that is also used to form ascites and is a signaling molecule in the body. Arginine is an intermediate product in the urea (containing L-ornithine, L-citrulline and argininosuccinic acid) and nitric oxide cycle (containing ornithine and argininosuccinic acid), and produce polyamine structures that can regulate cell function through ornithine. Arginine deficiency (inducible by increasing the activity of arginase, the enzyme that converts arginine to ornithine) impairs B cell function (immunity) and impairs hair and muscle growth and may also impair neuromuscular function. Arginase is known to be overexpressed in patients with type II diabetes and is a risk factor for the development of cardiovascular disease in this population cohort, and patients with renal failure may have reduced arginase.

It is precisely because arginine has the above-mentioned important role, so the detection of arginine content is also particularly important. The commonly used detection method of arginine is capillary electrophoresis (Li X-t et al., Chem Res Chin Univ 2013, 29(3):434-438; Meng J et al, The Analyst 2010, 135(7):1592-1599), high performance liquid chromatography (Tateda N et al., Analytical sciences: the international journal of the Japan Society for Analytical Chemistry 2001, 17(6):775-778; Wadud S et al., Journal of chromatography B, Analytical technologies in the biomedical and life sciences 2002, 767(2):369-374), ELISA and UV-Vis spectrophotometry (Hortpro M A et al, J Am Chem So 2003, 125(1):20-21; Pu F et al, Anal Chem 2010, 82(19):8211-8216; Du J et al, Chemical communications (Cambridge, England) 2013, 49(47):5399-5401; Engeser M et al, Chemical Communications 1999, (13):1191-1192) and fluorescence spectrometry (Engeser M et al. Chemical Communications 1999, (13): 1191-1192).

However, these detection methods have great defects in live cell research, requiring time-consuming sample processing procedures: cell disruption, separation, extraction and purification, etc., and it cannot perform in situ, real-time, dynamic, high-throughput, and high spatiotemporal resolution detection in living cells and subcellular organelles. There remains a need in the art for methods for in situ, quantitative, high-throughput detection of arginine in and out of cells in real time.

SUMMARY OF INVENTION

In view of this, the purpose of the present invention is to provide an arginine fluorescent sensor for real-time localization, high-throughput, and quantitative detection of arginine inside or outside cells.

To achieve the above object, the invention provides the following technical solutions:

The present invention provides an arginine optical sensor (probe) comprising an arginine-sensitive polypeptide or a functional variant thereof and an optically active polypeptide or a functional variant thereof, wherein the optically active polypeptide or functional variant thereof is located within the sequence of the arginine-sensitive polypeptide or functional variant thereof. The arginine-sensitive polypeptide or the functional variant thereof are divided into Part I and Part II by the optically active polypeptide or the functional variant thereof.

The invention provides an arginine optical sensor comprising arginine-sensitive polypeptide B and optically active polypeptide A, wherein the optically active polypeptide A is located in the sequence of the arginine-sensitive polypeptide B, dividing the arginine-sensitive polypeptide B into the first part B1 and the second part B2, forming a sensor structure of type B1-A-B2.

In one embodiment, the arginine-sensitive polypeptide comprises a arginine binding domain of a arginine binding protein and mutant thereof. In one embodiment, the arginine-sensitive polypeptide is a arginine binding protein or a functional fragment thereof. In one embodiment, the arginine binding protein is the STM4351 protein. In one embodiment, the arginine-sensitive polypeptide has the sequence shown in SEQ ID NO: 1 or having at least 35%, at least 40%, at least 50%, at least 60%, at least 70%, at least 80%, at least 85%, at least 90%, at least 95%, at least 97%, at least 99% sequence identity with SEQ ID NO: 1 and retains arginine-sensitive.

In one embodiment, the optically active polypeptide is a fluorescent protein or a functional fragment or variant thereof. In one embodiment, the fluorescent protein is selected from the group consisting of yellow fluorescent protein (cpYFP as shown in SEQ ID No: 2), orange fluorescent protein, red fluorescent protein, green fluorescent protein (cpGFP as shown in SEQ ID No: 3), blue fluorescent protein (cpBFP as shown in SEQ ID No: 4), and apple red fluorescent protein (cpmApple as shown in SEQ ID No: 5). Preferably, the optically active polypeptide is cpYFP. In one embodiment, the fluorescent protein has a sequence as shown in any of SEQ ID Nos: 2-5.

In one embodiment, the optical sensor further comprises one or more linkers flanking the optically active polypeptide. In one embodiment, the optically active polypeptide is flanked by a linker of no more than 5 amino acids, such as a linker of 0, 1, 2, 3, 4 amino acids. In one embodiment, the linker flanking the optically active polypeptide comprises amino acid Y. In one embodiment, linker Y is located N-terminal and/or C-terminal to the optically active polypeptide. In one embodiment, the optical sensor is shown as follows: the first part of the arginine-sensitive polypeptide B1-Y-optically active polypeptide A-the second part B2 of the arginine-sensitive polypeptide. In one embodiment, the present optical sensor does not comprise a linker.

In one embodiment, the optically active polypeptide is located between residues 103-111 and/or 197-209 of the arginine-sensitive polypeptide, wherein the numbering corresponding to the full length of the arginine-binding protein. In one embodiment, the optically active polypeptide replaces one or more amino acids between residues 102-112 and/or 196-210 of the arginine-sensitive polypeptide, wherein the numbering corresponding to the full length of the arginine-binding protein.

In one embodiment, the optically active polypeptide is located in the arginine-sensitive polypeptide at one or more sites selected from the group consisting of: 103/104, 103/105, 103/106, 103/107, 103/108, 103/109, 103/110, 103/111, 104/105, 104/106, 104/107, 104/108, 104/109, 104/110, 104/111, 105/106, 105/107, 105/108, 105/109, 105/110, 105/111, 106/107, 106/108, 106/109, 106/110, 106/111, 107/108, 107/109, 107/110, 107/111, 108/109, 108/110, 108/111, 109/110, 109/111, 110/111, 197/198, 197/199, 197/200, 197/201, 197/202, 197/203, 197/204, 197/205, 197/206, 197/207, 197/208, 197/209, 198/199, 198/200, 198/201, 198/202, 198/203, 198/204, 198/205, 198/206, 198/207, 198/208, 198/209, 199/200, 199/201, 199/202, 199/203, 199/204, 199/205, 199/206, 199/207, 199/208, 199/209, 200/201, 200/202, 200/203, 200/204, 200/205, 200/206, 200/207, 200/208, 200/209, 201/202, 201/203, 201/204, 201/205, 201/206, 201/207, 201/208, 201/209, 202/203, 202/204, 202/205, 202/206, 202/207, 202/208, 202/209, 203/204, 203/205, 203/206, 203/207, 203/208, 203/209, 204/205, 204/206, 204/207, 204/208, 204/209, 205/206, 205/207, 205/208, 205/209, 206/207, 206/208, 206/209, 207/208, 207/209 or 208/209.

Preferably, the optically active polypeptide is located at one or more positions of an arginine-sensitive polypeptide selected from the group consisting of: 103/104, 103/106, 103/107, 103/108, 103/109, 103/110, 104/105, 104/106, 104/108, 104/109, 104/110, 104/111, 105/106, 105/107, 105/108, 105/109, 105/110, 105/111, 106/107, 106/108, 106/109, 107/108, 107/109, 107/110, 107/111, 108/109, 108/111, 109/110, 109/111, 110/111, 197/198, 197/199, 197/200, 197/201, 197/202, 197/203, 197/204, 197/205, 197/206, 197/208, 198/201, 198/202, 198/203, 198/204, 198/205, 198/206, 198/208, 198/209, 199/200, 199/201, 199/202, 199/203, 199/204, 199/205, 199/206, 199/208, 200/203, 200/204, 200/205, 200/206, 200/207, 200/208, 201/202, 201/203, 201/204, 201/205, 201/206, 201/208, 201/209, 202/203, 202/205, 202/206, 203/204, 203/206, 204/205, 204/206, 204/208, 205/206, 205/207, 205/208 or 206/207. These sensors were more responsive to arginine than controls.

Preferably, the optically active polypeptide is located at one or more positions of an arginine-sensitive polypeptide selected from the group consisting of: 104/109, 104/110, 104/111, 105/106, 105/107, 105/110, 106/108, 106/109, 107/109, 107/111, 110/111, 197/199, 197/203, 197/204, 198/202, 198/203, 198/204, 199/200, 199/201, 199/202, 199/204, 199/205, 200/203, 200/204, 200/205, 200/206, 201/202, 201/203, 201/204, 201/205, 201/206, 202/205, 203/206, 204/205 or 204/206. These sensors responded more than 1.5-fold to arginine than controls.

Preferably, the optically active polypeptide is located at one or more positions of an arginine-sensitive polypeptide selected from the group consisting of: 104/110, 104/111, 105/106, 105/110, 106/109, 107/109, 107/111, 197/203, 197/204, 198/202, 199/200, 199/202, 200/203, 200/205, 201/202, 201/205, 202/205, 203/206, 204/205 or 204/206. These sensors responded more than 2-fold to arginine than controls.

In an exemplary embodiment, the optical sensor of the present invention may be a sensor with a cpYFP inserted at one or more sites selected from: 104/110, 104/111, 105/106, 105/110, 106/109, 107/109, 107/111, 197/203, 197/204, 198/202, 199/200, 199/202, 200/203, 200/205, 201/202, 201/205, 202/205, 203/206, 204/205 or 204/206. In one embodiment, the optical sensors of the present invention have or consist of the sequences shown in SEQ ID NOs: 6-39.

The present invention also provides mutants of arginine-sensitive polypeptides having one or more mutations. The amino acid mutation includes amino acid modification, substitution, deletion or sequence truncation. In one embodiment, the mutations are at 1, 2 or 3 of positions 30 (S), 96 (R) and 177 (D) of the arginine binding protein. Preferably, the mutation is selected from 1, 2 or 3 of S13N, D160N, R79M and R79K.

The present invention also provides optical sensors comprising arginine-sensitive polypeptides with one or more mutations. In one or more embodiments, the optical sensor is any optical sensor inserted with an optically active polypeptide as described above, and the arginine-sensitive polypeptide in the optical sensor has mutations at 1, 2 or 3 sites selected from S13, R79 and D160. In one or more embodiments, an optical sensor comprising a mutated arginine-sensitive polypeptide is no less responsive to arginine than its unmutated counterpart. Preferably, the mutation is selected from 1, 2 or 3 of S13N, D160N, R79M and R79K.

In an exemplary embodiment, the optical sensor of the present invention may be a sensor with cpYFP inserted into the 107/111 position of the arginine binding protein and having one or more mutations selected from S13N, D160N, R79M and R79K. Preferably, the optical sensor of the present invention is a sensor with cp YFP inserted into the 107/111 site of the arginine-binding protein and having a selected from S13N or D160N. In one embodiment, the optical sensors of the present invention have or consist of the sequences shown in SEQ ID NOs: 40-41.

The optical sensors of the present invention comprise any of the amino acid sequence of SEQ ID Nos: 6-41 or a variant thereof. In one embodiment, the optical sensors of the present invention comprise sequences having at least 35%, at least 40%, at least 50%, at least 60%, at least 70%, at least 80%, at least 85%, at least 90%, at least 95%, at least 99% sequence identity with any one of the amino acid sequences of SEQ ID Nos: 6-41.

The invention also provides fusion polypeptides comprising the optical sensors described herein and other polypeptides. In some embodiments, other polypeptides are located N- and/or C-terminal to the said optical sensor. In some embodiments, other polypeptides include polypeptides that localize optical sensors to different organelles or subcellular organelles, tags for purification, or tags for immunoblotting.

The invention also provides nucleic acid sequences comprising the coding sequences for the polypeptide, sensor, or protein described herein or a complementary sequence or fragment thereof. In one embodiment, the nucleic acid sequence of the present invention is selected from the group consisting of (1) the coding sequence of any of the amino acid sequences shown in SEQ ID Nos: 6-41 or complementary sequences thereof, (2) the sequences with at least 99%, 95%, 90%, 80%, 70% or 50% identity with (1), (3) the fragments of (1) or (2). In one embodiment, the nucleic acid sequence of the invention comprises SEQ ID No: 42 or a variant or fragment thereof. In one or more embodiments, the fragments are primers.

The invention also relates to complementary sequences of the nucleic acid sequences described above or variants thereof, including nucleic acid sequences encoding the fragments, analogs, derivatives, soluble fragments and variants of the optical sensors or fusion proteins of the invention or the complementary sequences thereof.

The invention also provides nucleic acid constructs comprising the nucleic acid sequences described herein, or their complementary sequences, which encode the optical sensors or fusion polypeptides described herein. In one or more embodiments, the nucleic acid construct is a cloning vector, expression vector, or recombinant vector. In one or more embodiments, the nucleic acid sequence is operably linked to an expression control sequence. In some embodiments, the expression vector is selected from the group consisting of prokaryotic expression vector, eukaryotic expression vector, and viral vector.

The invention also provides cells comprising the nucleic acid sequences or expression vector described in the invention. In one or more embodiments, the cells express an optical sensor or fusion polypeptide described herein.

The invention also provides a detection test kit comprising an optical sensor or fusion polypeptide or polynucleotide described herein, or an optical sensor or fusion polypeptide prepared according to the method described herein.

The invention provides methods for preparing the optical sensors described herein, comprising providing cells expressing the optical sensors or fusion polypeptides described herein, culturing the cells under conditions in which the cells express them, and isolating the optical sensors or fusion polypeptides.

The invention also provides a method for detecting arginine in a sample, comprising contacting the sample with an optical sensor or fusion polypeptide described herein, or an optical sensor or fusion polypeptide prepared according to the method described herein, and detecting changes in an optically active polypeptide. The detecting may be performed in vivo, in vitro, subcellularly, or in situ. Said sample is such as blood.

The invention also provides a method for quantitating arginine in a sample, comprising contacting the sample with an optical sensor or fusion polypeptide described herein or an optical sensor or fusion polypeptide prepared according to the method described herein, detecting changes in optically active polypeptide, and quantitating arginine in the sample according to the changes in optically active polypeptide.

The invention also provides a method for screening compounds, such as pharmaceuticals, comprising contacting a candidate compound with an optical sensor or fusion polypeptide described herein, or an optical sensor or fusion polypeptide prepared as described herein, detecting changes in the optically active polypeptide, and screening the compounds according to the changes in the optically active polypeptide. Said method allows high-throughput screening of compounds.

The invention also provides use of a arginine optical sensor or fusion polypeptide described herein or a arginine optical sensor or fusion polypeptide prepared according to the methods described herein in intracellular/extracellular localization of arginine. In one or more embodiments, the localization is in real time.

Beneficial effects of the present invention: the arginine fluorescent sensor provided by the present invention includes arginine-sensitive polypeptide B and fluorescent protein A; the fluorescent protein A is inserted into the polypeptide B, and the B is divided into two parts, the polypeptide B1 and the polypeptide B2, to form a sensor structure of the formula B1-A-B2; the B1-A-B2 type arginine fluorescent sensor provided by the invention is easy to mature, has large dynamic change of fluorescence and good specificity, and can be expressed in cells by means of gene manipulation, and can be real-time localized, high-throughput, and quantitatively detected arginine in and out of cells. Time-consuming sample handling steps are eliminated. The experimental results show that the highest response of the arginine fluorescent sensor provided by the present application to arginine is more than 11 times, and the localization of cells can be detected in subcellular structures such as cytoplasm, mitochondria, nucleus, Golgi apparatus, peroxisomes and lysosomes, and high-throughput compound screening and quantitative detection of arginine in blood can be performed.

The present invention also provides a method for preparing the above-mentioned arginine optical sensor, comprising the following steps: 1) incorporating the nucleic acid sequence encoding the arginine optical sensor described herein into an expression vector; 2) transferring the expression vector into the host cell; 2) culturing the host cell under conditions suitable for the expression of the expression vector, 3) separation of arginine optical sensors.

BRIEF DESCRIPTION OF THE DRAWINGS

The invention is further illustrated below in combination with the drawings and examples.

DETAILED DESCRIPTION

Figure 1:
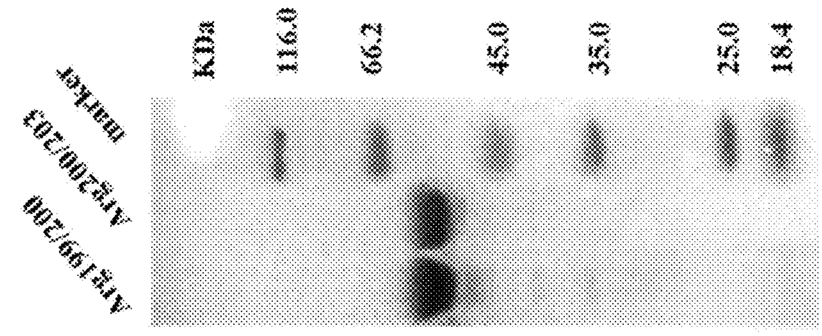
FIG. 1 is a graph of SDS-PAGE analysis of the arginine fluorescent sensor in Example 2.

When a value or range is given, the term "about" used herein means that the value or range is within 20%, within 10%, and within 5% of the given value or range.

The terms "comprise", "include", and equivalent forms thereof include the meaning of "contain" as well as "consist of", for example a composition "comprising" X may consist of X alone or may contain other substances, such as X+Y.

The term "arginine-sensitive polypeptide" or "arginine-responsive polypeptide" used herein refers to a polypeptide which responds to arginine production including any response in chemical, biological, electrical, or physiological parameters of a polypeptide that interacts with the sensitive-polypeptide. The response includes small changes, for example, changes in the orientation of the amino acid or peptide fragment of the polypeptide and, for example, changes in the primary, secondary or tertiary structure of the polypeptide, including, for example, changes in protonation, electrochemical potential and/or conformation. "Conformation" is the three-dimensional arrangement of the primary, secondary, and tertiary structure of a molecule containing side groups in the molecule; when the three-dimensional structure of the molecule changes, the conformation changes. Examples of conformational changes include transitions from a-helix to β-fold or from β-fold to α-helix. It should be understood that detectable alterations need not be conformational changes as long as the fluorescence of the fluorescent protein moiety is altered. The arginine-sensitive polypeptide described herein may also include functional variants thereof. The functional variants of the arginine-sensitive polypeptide include, but are not limited to, variants that can interact with arginine and thereby undergo the same or similar changes as the parent arginine-sensitive polypeptide.

The arginine-sensitive polypeptides of the present invention include, but are not limited to, the arginine-binding protein STM4351 derived from *Salmonella Typhimurium* or the arginine periplasmic binding protein derived from *Escherichia coli* or have variants with more than 90% homology. These binding proteins consist of two domains connected by two flexible amino acid peptide chains. Arginine-binding proteins can sense changes in arginine concentration, and the spatial conformation of arginine-binding proteins also changes greatly during the dynamic change of arginine concentration. STM4351 consists of an arginine-binding/regulatory domain and a DNA-binding domain. An exemplary STM4351 protein is shown in SEQ ID NO:1. In one or more embodiments, the arginine-sensitive polypeptide comprises the arginine-binding domain of the STM4351 protein, but does not include the DNA-binding domain.

The term "optical probe" or "optical sensor" as used herein refers to an arginine-sensitive polypeptide fused to an optically active polypeptide. The inventors discovered that the conformational changes produced by binding an arginine-sensitive polypeptide, such as an arginine binding protein to a physiological concentration of arginine specifically by arginine sensitive polypeptides causes conformational changes in an optically active polypeptides, such as fluorescent proteins, which in turn result in the alteration of the optical properties of the optically active polypeptides. A standard curve is plotted with the help of the fluorescence of fluorescent proteins determined at different concentrations of arginine allows the presence and/or level of arginine to be detected and analyzed. When describing the optical sensors of the invention (eg, when describing insertion sites or mutation sites), references to amino acid residue numbering refer to SEQ ID NO:1.

In the present optical sensor, an optically active polypeptide, such as a fluorescent protein, is operably inserted into a arginine-sensitive polypeptide. The protein-based "optically active polypeptides" are polypeptides with the ability to emit fluorescence. In the present optical sensor, an optically active polypeptide, such as a fluorescent protein, is operably inserted into a arginine-sensitive polypeptide. Preferably, the protein substrate is selected to have fluorescence properties that are easily distinguishable in the unactivated and activated conformational states. The optically active polypeptide described herein may also be a functional variant thereof. A functional variant of the optically active polypeptide includes, but is not limited to, a variant for which the same or similar change in fluorescence property may occur as the parent optically active polypeptide.

The term "fluorescent protein" used herein refers to a protein that fluoresces upon irradiation with excitation light. Fluorescent proteins have been used as basic detection means in the field of biological sciences, such as green fluorescent protein (GFP) commonly used in biotechnology and circularly rearranged blue fluorescent protein (cpBFP), circularly rearranged green fluorescent protein (cpGFP), circularly rearranged yellow fluorescent protein (cpYFP) derived from mutations in this protein, etc; there are also a red fluorescent protein (RFP) commonly used in the art, and circularly rearranged proteins derived from this protein, such as cpmApple, cpmOrange, cpmKate, and others. Those skilled in the art know fluorescent proteins and sequences thereof that can be used for the invention. Exemplarily, cpYFP as shown in SEQ ID No: 2; cpGFP as shown in SEQ ID No: 3; cpBFP as shown in SEQ ID No: 4; and cpmApple as shown in SEQ ID No: 5.

A "linker" or "linker region" refers to an amino acid or nucleotide sequence linking two parts in a polypeptide, protein, or nucleic acid of the invention. Exemplarily, the number of amino acids at the amino terminus of the linker region of the arginine-sensitive polypeptide to the optically active polypeptide in the invention is selected to be 0-3, and the number of amino acids at the carboxyl terminus is selected to be 0-2; when a recombinant optical sensor is linked to a functional protein as a basic unit, it can be fused at the amino or carboxyl terminus of the recombinant optical sensor. The linker sequence may be a short peptide chain composed of one or more flexible amino acids, as in Y.

The arginine optical sensors of the invention include arginine-sensitive polypeptide B, such as a arginine binding protein or its variants, and optically active polypeptide A, such as a fluorescent protein. The optically active polypeptide A is inserted into the arginine sensitive polypeptide B, and B was divided into two parts, B1 and B2, to form the sensor structure of the formula B1-A-B2; the interaction between the arginine-sensitive polypeptide B and arginine results in a stronger optical signal for optically active polypeptide A.

In the present optical sensor, the optically active polypeptide may be located anywhere in the arginine-sensitive polypeptide. In one embodiment, the optically active polypeptide is located anywhere in N—C direction over a arginine-sensitive polypeptide in N—C direction. Specifically, the optically active polypeptide is located in a flexible region of a arginine-sensitive polypeptide that refers to some specific structures present in higher structures of a protein such as loop domains, which are more mobile and flexible than other higher structures of the protein, and this region may undergo dynamic changes in spatial structural conformation upon binding of this protein and a ligand. The flexible region mentioned in the present invention mainly refers to the region where the insertion site is located in the arginine-binding protein, such as the regions of amino acid residues 102-112 and 196-210. In one embodiment, the optically active polypeptide is located at one or more sites of an arginine-sensitive polypeptide selected from the group consisting of: 103/104, 103/105, 103/106, 103/107, 103/108, 103/109, 103/110, 103/111, 104/105, 104/106, 104/107, 104/108, 104/109, 104/110, 104/111, 105/106, 105/107, 105/108, 105/109, 105/110, 105/111, 106/107, 106/108, 106/109, 106/110, 106/111, 107/108, 107/109, 107/110, 107/111, 108/109, 108/110, 108/111, 109/110, 109/111, 110/111, 197/198, 197/199, 197/200, 197/201, 197/202, 197/203, 197/204, 197/205, 197/206, 197/207, 197/208, 197/209, 198/199, 198/200, 198/201, 198/202, 198/203, 198/204, 198/205, 198/206, 198/207, 198/208, 198/209, 199/200, 199/201, 199/202, 199/203, 199/204, 199/205, 199/206, 199/207, 199/208, 199/209, 200/201, 200/202, 200/203, 200/204, 200/205, 200/206, 200/207, 200/208, 200/209, 201/202, 201/203, 201/204, 201/205, 201/206, 201/207, 201/208, 201/209, 202/203, 202/204, 202/205, 202/206, 202/207, 202/208, 202/209, 203/204, 203/205, 203/206, 203/207, 203/208, 203/209, 204/205, 204/206, 204/207, 204/208, 204/209, 205/206, 205/207, 205/208, 205/209, 206/207, 206/208, 206/209, 207/208, 207/209 or 208/209. In the present invention, if the two numbers in a site represented in "X/Y" form are consecutive integers, this means that the optically active polypeptide is located between the amino acids stated by those numbers. For example, insertion site 93/94 indicates that the optically active polypeptide is located between amino acids 93 and 94 of the arginine-sensitive polypeptide. If the two numbers in a site represented in "X/Y" form are not consecutive integers, it indicates that the optically active polypeptide displaces the amino acids between the amino acids indicated by those numbers. For example, insertion site 93/97 indicates the replacement of amino acids 94-96 of the lactate-sensitive polypeptide by an optically active polypeptide. Preferably, the optically active polypeptide is located at one or more positions of an arginine-sensitive polypeptide selected from the group consisting of: 104/110, 104/111, 105/106, 105/110, 106/109, 107/109, 107/111, 197/203, 197/204, 198/202, 199/200, 199/202, 200/203, 200/205, 201/202, 201/205, 202/205, 203/206, 204/205 or 204/206.

When referring to a certain polypeptide or protein, the term "variant" or "mutant" used herein includes variants that have the same function of said polypeptide or protein but differ in sequence. Variants of polypeptides or proteins can include: homologous sequences, conservative variants, allelic variants, natural mutants, induced mutants. These variants include, but are not limited to: deletions, insertions and/or substitutions of one or more (usually 1-30, preferably 1-20, more preferably 1-10, most preferably 1-5) amino acids in the sequence of the polypeptide or protein, and sequences obtained by adding one or more (usually within 20, preferably within 10, more preferably within 5) amino acids to its carboxy terminus and/or amino terminus. These variants may also comprise at least about 70%, at least about 75%, at least about 80%, at least about 85%, at least about 90%, at least about 95%, at least about 98%, at least about 99% or 100% sequence identity to the polypeptide or protein. Not limited by theory, an amino acid residue is altered without changing the overall configuration and function of the polypeptide or protein, i.e., a functionally conserved mutation. For example, in the art, substitution with amino acids of approaching or similar property generally does not alter the function of a polypeptide or protein. In the art, amino acids with similar property tend to refer to families of amino acids with similar side chains, which have been well defined in the art. These families include amino acids with basic side chain (e.g., lysine, arginine, histidine), amino acids with acidic side chain (e.g., aspartic acid, glutamic acid), amino acids with uncharged polar side chain (e.g., glycine, asparagine, glutamine, serine, threonine, tyrosine, cysteine), amino acids with non-polar side chain (e.g., alanine, valine, leucine, isoleucine, arginine, phenylalanine, methionine, tryptophan), amino acids with β-branched side chain (e.g., threonine, valine, isoleucine) and amino acids with aromatic side chain (e.g., tyrosine, phenylalanine, tryptophan, histidine). For another example, the addition of one or more amino acids to the amino terminus and/or carboxy terminus also generally does not alter the function of a polypeptide or protein. The conservative amino acid substitutions of many commonly known non-genetic coding amino acids are known in the art. Conservative substitutions of other non-coding amino acids can be determined based on a comparison of their physical properties with those of the amino acids that are genetically encoded.

In two or more sequences of a polypeptide or nucleic acid molecule, the terms "identity" or "percent identity" refer to when the maximum correspondence is compared and aligned by manual alignment and visual inspection using methods known in the art such as sequence comparison algorithms, in a comparison window or a specified region, two or more sequences or subsequences are identical or have a certain percentage of amino acid residues or nucleotides that are identical in the specified region (e.g., 60%, 65%, 70%, 75%, 80%, 85%, 90%, 91%, 92%, 93%, 94%, 95%, 96%, 97%, 98%, 99%, or 100% identical). For example, the preferred algorithms suitable for determination of percent identity and percent similarity are the BLAST and BLAST 2.0 algorithms, respectively, see Altschul et al., (1977) nucleic acids res. 25:3389 and Altschul et al., (1990) J. mol. Biol 215:403.

Those skilled in the art is well known that in gene cloning operation, it is often necessary to design a suitable restriction enzyme cutting site, which is bound to introduce one or more incoherent residues at the ends of the expressed polypeptide or protein, and this does not affect the activity of the polypeptide or protein of interest. Also for constructing fusion proteins, facilitating the expression of recombinant proteins, obtaining recombinant proteins that are automatically secreted outside the host cell, or facilitating the purification of recombinant proteins, it is often necessary to add some amino acids to the N-terminus, C-terminus, or other suitable regions within the recombinant protein, for example, including but not limited to, suitable linker peptides, signal peptides, leader peptides, terminal extensions, glutathione S-transferases (GSTs) maltose E-binding protein, Protein A, tags such as 6His or flag, or the proteolytic enzyme sites of Factor Xa or thrombin or enterokinase.

The present optical sensor may comprise a arginine-sensitive polypeptide with a mutation. In one embodiment, the mutations are at positions 30(S), 96(R) and 177(D) of the arginine binding protein. Exemplarily, the mutations are S13N, D160N, R79M, R79K. The arginine-sensitive polypeptide in the optical sensor of the present invention may be the mutant. In an exemplary embodiment, the optical sensor of the present invention may be a sensor with cpYFP inserted into the 107/111 position of the arginine binding protein and having one or more mutations selected from the group consisting of S13N, D160N, R79M and R79K.

The terms "functional fragment", "derivative", and "analog" used herein refer to proteins that maintain essentially the same biological function or activity as the original polypeptide or protein (e.g., an arginine binding protein or a fluorescent protein). Functional variants, derivatives, or analogues of a polypeptide or protein (e.g., a arginine binding protein or a fluorescent protein) of the invention may be (i) a protein having one or more conservative or nonconservative amino acid residues (preferably conservative amino acid residues) substituted, whereas such substituted amino acid residues may or may not be encoded by the genetic code, or (ii) a protein having a substituted group in one or more amino acid residues, or (iii) a protein formed by the fusion of the mature protein to another compound, such as a compound that extends the half-life of the protein, such as polyethylene glycol, or (iv) a protein formed by the fusion of an additional amino acid sequence to this protein sequence (such as a secretory sequence or the sequence or protein used to purify this protein, or the fusion protein formed with an antigenic IgG fragment). According to the teaching herein, these functional variants, derivatives, and analogues belong to the common knowledge to those skilled in the art.

The difference of said analogues from the original polypeptide or protein may be a difference in amino acid sequence, a difference in modified form that does not affect the sequence, or both. These proteins include natural or induced genetic variants. Induced variants can be derived by various techniques, such as random mutagenesis by radiation or exposure to mutagens and can also be obtained by site directed mutagenesis or other known techniques in molecular biology.

The analogues also include analogues with a residue (such as a D-amino acid) different from the natural L-amino acid, as well as those with a non-natural or synthetic amino acids (such as B, y-amino acids). It is understood that the arginine-sensitive polypeptides of the present invention are not limited to the representative proteins, variants, derivatives, and analogues above. Modified (usually without changing the primary structure) forms include chemically derived forms of the protein such as acetylated or carboxylated forms, in vivo or in vitro. Modifications also include glycosylation, such as those resulting from glycosylation modifications either in the synthesis and processing of the protein or in further processing steps. This modification can be accomplished by exposing the protein to enzymes for glycosylation, such as mammalian glycosylases or deglycosylases. The modified forms also include sequences with phosphorylated amino acid residues such as phosphotyrosine, phosphoserine, phosphothreonine. Proteins that were modified to improve their antiproteolytic properties or optimize the solubilization properties were also included.

The present fusion polypeptide comprises the optical sensor described herein and an additional polypeptide. In some embodiments, the optical sensor described herein also comprises another polypeptide fused to it. The additional polypeptide described herein does not affect the property of the optical sensor. The additional polypeptide may be located N- and/or C-terminal to the optical sensor. In some embodiments, other polypeptides include polypeptides that localize optical sensors to different organelles or subcellular organelles, tags for purification, or tags for immunoblotting. There may be a linker between the optical sensor and the additional polypeptide in the fusion polypeptide described herein.

The subcellular organelles described here include cytosol, mitochondria, nucleus, endoplasmic reticulum, cell membrane, Golgi apparatus, lysosome, and peroxisome, among others. In some embodiments, the tag for purification or the tag for immunoblotting include 6 histidine (6*His), glutathione sulfurtransferase (GST), Flag.

The expression vector of the present invention comprises the nucleic acid sequence of the present invention or a complementary sequence thereof operably linked to an expression control sequence, the nucleic acid sequence encoding the optical sensor or fusion polypeptide of the present invention. The terms "nucleic acid" or "nucleotide" or "polynucleotide" or "nucleic acid sequence" used herein may be in the form of DNA or in the form of RNA. DNA form includes cDNA, genomic DNA, or artificially synthesized DNA. DNA can be single stranded or double stranded. DNA can be either the coding or noncoding strand. When referring to nucleic acids, the term "variant" used herein may be a naturally occurring allelic variant or a non-naturally occurring variant. These nucleotide variants include degenerate variants, substitution variants, deletion variants, and insertion variants. As is known in the art, an allelic variant is a form of substitution of a nucleic acid, which may be a substitution, deletion, or insertion of one or more nucleotides but does not substantially alter the function of the protein it encodes. The nucleic acid of the invention may comprise a nucleotide sequence having sequence identity of at least about 50%, at least about 60%, at least about 70%, at least about 75%, at least about 80%, at least about 85%, at least about 90%, at least about 95%, at least about 98%, at least about 99%, or 100% to the nucleic acid sequence. The invention also relates to a nucleic acid fragment that hybridizes to the sequences described above. As used herein, a "nucleic acid fragment" is at least 15 nucleotides in length, preferably at least 30 nucleotides, more preferably at least 50 nucleotides, and even more preferably at least 100 nucleotides or more. The nucleic acid fragment can be used in amplification techniques of nucleic acids (such as PCR).

The full-length sequences or fragments thereof of the optical sensors or fusion proteins of the invention can often be obtained by PCR amplification, artificial synthesis or recombinant procedures. For PCR amplification, primers can be designed according to the nucleotide sequences disclosed in the invention and the sequences in interest can be amplified with a commercially available cDNA library or a cDNA library prepared by conventional methods known to those skilled in the art as template. When the nucleotide sequence is greater than 2500 bp, it is preferable to perform 2~6 rounds of PCR amplification, and then the individually amplified fragments are spliced together in the correct order. There is no special limit to the procedures and systems for PCR amplification described herein, and conventional PCR amplification procedures and systems in the art may be used. Recombination can also be used to obtain relevant sequences in bulk. This is usually by cloning into a vector, retransferring into cells, and then isolating and purifying the polypeptide or protein in inserest from proliferated host cells by conventional methods. In addition, synthetic methods are also available to synthesize the sequence in interest, especially for short fragments. In the present invention, when the nucleotide sequence of the optical sensor is less than 2500 bp, it may be synthesized by an artificial synthetic method. The artificial synthetic method is a conventional artificial synthetic method for DNA in the art with no other special requirements. In general, many small fragments are first synthesized, and then ligated to obtain a very long sequence. At present, it has become possible to obtain, entirely by chemical synthesis, DNA sequences encoding the proteins of the invention (or functional variants, derivatives, or analogs thereof). This DNA sequence can then be introduced into a variety of existing DNA molecules known in the art, such as vectors, and into cells. Mutations can be introduced into the protein sequence of the invention by methods such as mutation PCR or chemical synthesis.

The invention also relates to a nucleic acid construct containing the polynucleotides described herein, and one or more regulatory sequences operably linked to such sequences. The polynucleotides described herein can be manipulated in a variety of ways to guarantee expression of said polypeptide or protein. The nucleic acid construct can be manipulated according to the difference or requirements of the expression vector prior to insertion of the nucleic acid construct into the vector. Techniques that utilize recombinant DNA methods to alter polynucleotide sequences are known in the art.

In certain embodiments, the nucleic acid construct is a vector. The vector may be a cloning vector, an expression vector, or a homologous recombination vector. The polynucleotides of the present invention can be cloned into many types of vectors, e.g., plasmids, phagemids, phage derivatives, animal viruses, and cosmids. Cloning vectors can be used to provide coding sequences for proteins or polypeptides of the invention. Expression vectors can be provided to cells in the form of bacterial or viral vectors. Expression of the present polynucleotides is generally achieved by operably linking the polynucleotides of the invention to a promoter and incorporating the construct into an expression vector. This vector may be suitable for replicating and integrating eukaryotic cells. A typical expression vector contains an expression control sequence that can be used to regulate the expression of the desired nucleic acid sequence. In one or more embodiments, the cloning vector and the expression vector are one vector, i.e., a cloning expression vector. Homologous recombination vectors are used to integrate the expression frame described herein into the host genome.

The term "expression control sequence" used herein refers to elements that regulate the transcription, translation, and expression of a gene of interest and can be operably linked to the gene of interest, which may be a replication origin, promoter, marker gene, or translational control element, including enhancers, operons, terminators, ribosome binding sites, etc., and the choice of expression control sequence depends on the host cell used. In recombinant expression vectors, "operable ligation" refers to the attachment of the nucleotide sequence of interest to a regulatory sequence in a manner that allows the expression of the nucleotide sequence. Those skilled in the art are well known of methods for constructing expression vectors containing the present fusion protein coding sequences and suitable transcription/translation control signals. These include in vitro recombinant DNA techniques, DNA synthesis techniques, in vivo recombination techniques, etc. Said DNA sequence can be effectively ligated to an appropriate promoter in an expression vector to direct mRNA synthesis. Representative examples of these promoters are: the lac or trp promoter of *E. coli*; A-phage PL promoter; eukaryotic promoters including the CMV immediate early promoter, the HSV thymidine kinase promoter, the early and late SV40 promoters, the LTR of retroviruses, and several other promoters known to control gene expression in prokaryotic or eukaryotic cells or their viruses. The expression vector also includes a ribosome binding site for translation initiation and a transcription terminator. In one embodiment, the expression vector may use a commercially available pET28a vector with no other special requirements. Exemplarily, BamHI and EcoRI were employed to double digest the nucleotide sequence encoding the optical sensor and the expression vector, respectively, and then the enzymatic cleavage products of both were ligated to give recombinant expression vectors. The present invention makes no special limitation to the specific steps and parameters of enzymatic cleavage and ligation, and those conventional in the art would work.

After a recombinant expression vector is obtained, this vector is transformed into host cells to produce a protein or peptide including the fusion protein. This transfer process can be performed with conventional techniques well known to those skilled in the art, such as transformation or transfection. The host cells described herein refer to cells capable of receiving and accommodating recombinant DNA molecules, which are sites of recombinant gene amplification, and ideally the recipient cell should satisfy both conditions of easy access and proliferation. The "host cells" of the invention may include prokaryotic cells and eukaryotic cells, specifically including bacterial cells, yeast cells, insect cells, and mammalian cells. Specific examples can be bacterial cells of *E. coli, Streptomyces* spp., *Salmonella typhimurium*, fungal cells such as yeast, plant cells, insect cells of *Drosophila* S2 or Sf9, CHO, COS, HEK293, HeLa cells, or animal cells such as Bowes melanoma cells, among others, including but not limited to those host cells described above. The host cells are said to prefer a variety of cells favouring the expression or fermentative production of the gene product, such cells being well known and commonly used in the art. An exemplary host cell used in the examples of the present invention is *Escherichia coli* JM109-DE3 strain. Those skilled in the art well know how to select appropriate vectors, promoters, enhancers, and host cells.

The methods of transfer to host cells described herein are conventional methods in the art, including calcium phosphate or calcium chloride coprecipitation, DEAE-mannan-mediated transfection, lipofection, naturally competent cells, chemically mediated transfer, or electroporation. When the host is a prokaryote such as *E. coli*, the process described is preferably $CaCl_2$) method or $MgCl_2$ method, and their steps used are well known in the art. When the host cell is a eukaryotic cell, the following DNA transfection methods are used: calcium phosphate coprecipitation, conventional mechanical methods such as microinjection, electroporation, liposome packaging, etc.

After transferring the expression vector into host cells, the host cells transferred with the expression vector are subjected to expansion and expression culture, and the arginine optical sensor is isolated. The host cells are expanded for expression by conventional methods. Depending on the host cell species used, the medium used in culture may be various conventional media. Culture is performed under conditions suitable for host cell growth.

In the present invention, an optical sensor is expressed intracellularly, on the cell membrane, or secreted outside the cell. Recombinant proteins can be isolated or purified by various separation methods, if desired, using their physical, chemical, and other properties. The present invention does not have a special limit to a process for separating said arginine fluorescent proteins, and a conventional method for the isolation of fusion proteins in the art would work. These methods are well known to those skilled in the art and include, but are not limited to: conventional renaturation treatments, salting out methods, centrifugation, osmotic disruption, sonication, ultra centrifugation, molecular sieving chromatography, adsorption chromatography, ion exchange chromatography, high performance liquid chromatography (HPLC) and other liquid chromatography techniques and the combination of these methods. In one embodiment, His tag affinity chromatography is utilized for optical sensor isolation.

The invention also provides use of said arginine optical sensors in real-time localization, quantitative detection of arginine as well as high-throughput compound screening. In one aspect, said arginine optical sensor, preferably linked with signal peptides at different parts of the cell, is transferred into cells for real-time localization of arginine by detecting the strength of fluorescence signals in cells; corresponding quantitative detection of arginine is performed by a arginine standard titration curve. The arginine standard titration curve described herein is plotted from the fluorescence signals of an arginine optical sensor in the presence of different concentrations of arginine. The arginine optical sensor described herein is directly transferred into cells, which is more accurate without time-consuming sample processing process during the real-time localization and quantitative detection of arginine. The present arginine optical sensor, when performing high-throughput compound screening, adds different compounds to the cell culture fluid, determines changes in arginine content, and thus screens out compounds that influence the changes in arginine content. The use of the arginine optical sensors described herein in real-time localization, quantitative detection of arginine as well as high-throughput compound screening are all non-diagnostic and therapeutic purposes, not related to the diagnosis and treatment of diseases.

Concentrations, contents, percentages, and other values may be expressed with ranges available herein. It is also understood that use of these ranges is only for convenience and conciseness, which should be interpreted elastically to include values explicitly mentioned in the upper and lower limits of the range, but also to include all individual values or sub ranges included in the ranges.

Example

The arginine fluorescent sensors provided by the invention are described in detail below in combination with the examples, but they cannot be understood as defining the scope of protection of the invention.

I. Experimental Materials and Reagents

The conventional molecular biology cloning methods for genetic engineering and cell culture and imaging methods mainly used in examples are well known to those skilled in the art, for example, Roskams, J., *Molecular Biology Laboratory Handbook*, J. Sambrook, D. W. Russell ed, *Molecular Cloning: A Laboratory Manual*, translated by Peitang Huang et al. (3rd edition, August 2002, Science Press); R. I. Freshney et al., *Culture of Animal Cells: a Manual of Basic Technique* (5th edition), translated by Jingbo Zhang and Cunquan Xu; Juan S. Bonifacino, M. Daso, et al., *Short Protocols in Cell Biology*, translated by Jingbo Zhang et al.

The pET28a-cpYFP based, pET28a-arginine binding protein plasmid used in examples was constructed by the Protein Laboratory of East China University of Science and Technology, and the pET28a plasmid vector was purchased from Invitrogen. All the primers used for PCR were synthesized, purified, and identified to be correct by mass spectrometry (MS) by Shanghai Generay Biotech Co., Ltd. The expression plasmids constructed in examples were all sequenced by BGI and Jie Li Sequencing. For each example, Taq DNA polymerase was purchased from Dongsheng Bio, pfu DNA polymerase was purchased from Tiangen Biochemical Technology (Beijing) Co., Ltd, primeSTAR DNA polymerase was purchased from Takara, and all three polymerases were purchased with corresponding polymerase buffer and dNTPs. Restriction enzymes such as BamHI, BglII, HindIII, NdeI, XhoI, EcoRI, SpeI, T4 ligase, and T4 phosphorylase (T4 PNK) were purchased from Fermentas with corresponding buffers and the like. Transfection reagent Lip2000 Kit was purchased from Invitrogen. Arginine and the like were purchased from Sigma. Chemical reagents such as inorganic salts were purchased from sigma-aldrich unless specifically stated. HEPES salt, Ampicillin (Amp), and puromycin were purchased from Ameresco. 96 well detection black plates, 384 well fluorescence detection black plates were purchased from Grenier.

The DNA purification kit used in examples was purchased from BBI (Canada), and the common Plasmid Mini Preparation Kit was purchased from Tiangen Biochemical Technology (Beijing) Co., Ltd. Clonal strain Mach1 was purchased from Invitrogen. Nickel column affinity chromatography columns and desalting column packing were from GE Healthcare.

The main instruments used in examples: Biotek Synergy 2 multi-purpose microplate reader (Bio-Tek, USA), X-15R high-speed refrigerated centrifuge (Beckman, USA), Microfuge22R tabletop high-speed refrigerated centrifuge (Beckman, USA), PCR amplimer (Biometra, Germany), ultrasonic disruptor (Ningbo SCIENTZ), nucleic acid electrophoresis instrument (Shennengbocai company), spectrofluorometer (Varian, USA), CO2 constant temperature cell culture incubator (SANYO), and inverted fluorescence microscope (Nikon, Japan).

II. Molecular Biology Methods and Cellular Experimental Methods

II.1 Polymerase Chain Reaction (PCR):

1. PCR Amplification of Target Fragments:

This method was mainly used for gene fragment amplification and colony PCR to identify positive clones. The reaction system for PCR amplification was as follows: template sequence 0.5-1 μl, the forward primer (25 μM) 0.5 μl, the reverse primer (25 μM) 0.5 μl, 10×pfu buffer 5 μl, pfu DNA polymerase 0.5 μl, dNTP (10 mM) 1 μl, sterilized ultrapure water (ddH2O) 41.5-42 μl, to a total volume of 50 μl. The PCR amplification program was as follows: denaturation at 95° C. for 2-10 min, 30 cycles (94-96° C. for 30-45 s, 50-65° C. for 30-45 s, 72° C. for a period (600 bp/min)), and extension at 72° C. for 10 min.

2. PCR Amplification of Long Fragments (>2500 bp):

Long fragment amplification, primarily inverse PCR amplification vector, used in the invention is a technique used to obtain site directed mutations in examples below. Reverse PCR primers were designed at the variation site, where the 5' end of one primer contained the variant nucleotide sequence. Amplified products contained the corresponding mutation site. The reaction system of amplification PCR of long fragments were as follows: template sequence (10 μg-1 ng) 1 μl, the forward primer (25 μM) 0.5 μl, the reverse primer (25 μM) 0.5 μl, 5×PrimerSTAR buffer 10 μl, PrimerSTAR DNA polymerase 0.5 μl, dNTPs (2.5 mM) 4 μl, sterilized ultrapure water (ddH2O) 33.5 μl, to a total volume of 50 μl. The PCR amplification program was as follows: denaturation at 95° C. for 5 min, 30 cycles (98° C. for 10 s, 50-68° C. for 5-15 s, 72° C. for a period (1000 bp/min)), and extension at 72° C. for 10 min; or denaturation at 95° C. for 5 min, 30 cycles (98° C. for 10 s, 68° C. for a period (1000 bp/min)), and extension at 72° C. for 10 min.

II.2 Endonuclease Digestion Reaction:

The system for double digestion of plasmid vectors was as follows: plasmid vector 20 μl (approximately 1.5 μg), 10×Buffer 5 μl, restriction endonuclease 11-2 μl, restriction endonuclease 21-2 μl, made up to a total volume of 50 μl with sterilized ultrapure water. Reaction conditionsL 37° C. for 1-7 hours.

II.3 5' Phosphorylation Reaction of DNA Fragments

Because the plasmid or genomic end extracted from microorganisms contains phosphate groups, but the PCR product does not, the 5' end base of the PCR product needs to be subjected to a phosphate group addition reaction, and only the DNA molecule with phosphate groups on its end allows ligation reaction. The phosphorylation reaction system was as follows: the PCR product fragments DNA sequences 5-8 μl, 10×T4 ligase buffer 1 μl, T4 polynucleotide kinase (T4 PNK) 1 μl, sterilized ultrapure water 0-3 μl, to a total volume of 10 μl. The reaction conditions were 37° C. for 30 min-2 hours followed by inactivation at 72° C. for 20 min.

II.4 Ligation of Target Fragments and Vectors

There are differences in the ligation method between different fragments and vectors, and three ligation methods are used in this invention.

1. Ligation of Blunt End Short Fragments and Linearized Vectors

The principle of this method is that the blunt end product obtained by PCR, after phosphorylation of the 5' end of the DNA fragment by T4 PNK, is ligated with a linearized vector in the presence of PEG4000 and T4 DNA ligase to obtain a recombinant plasmid. The homologous recombination ligation system was as follows: T4 PNK treated DNA fragment 4 μl, linearized vector fragment 4 μl, PEG4000 1 μl, 10×T4 ligase buffer 1 μl, T4 DNA ligase 1 μl, to total of 10 μl. The reaction condition was 22° C. for 30 min.

2. Ligation of DNA Fragments Containing Cohesive Ends and Vector Fragments Containing Cohesive Ends DNA fragments cleaved by restriction enzymes often give rise to overhang sticky ends and can therefore be joined with sticky end vector fragments containing sequence complementarity to form recombinant plasmids. The ligation reaction system was as follows: digested PCR product fragments DNA 1-7 μl, digested plasmid 0.5-7 μl, 10×T4 ligase buffer 1 μl, T4 DNA ligase 1 μl, sterilized ultrapure water added to a total volume of 10 μl. The reaction condition was 16° C. for 4-8 hours.

3. Ligation Reactions in which the Products of DNA Fragments Phosphorylated at the 5' End were Self Circularized after Site Directed Mutagenesis were Introduced by Inverse PCR The recombinant plasmid was generated by ligating the 3' and 5' ends of the linearized vector into a DNA fragment phosphorylated at the 5' end by a self circularization ligation reaction. The reaction system for self cyclization ligation was as follows: phosphorylation reaction system 10 μl, T4 ligase (5 U/μl) 0.5 μl, to a total volume of 10.5 μl. The reaction condition was 16° C. for 4-16 hours.

II.5 Preparation and Transformation of Competent Cells

Preparation of Competent Cells:

1. A single colony (e.g., Mach1) is picked and inoculated in 5 ml LB medium at 37° C. on a shaker overnight.
2. 0.5-1 ml of overnight cultured broth was taken and transferred into 50 ml LB medium and incubated at 37° C. at 220 rpm for 3 to 5 hours until the OD600 reached 0.5.
3. The cells were precooled in ice bath for 2 hours.
4. 4° C., centrifugation at 4000 rpm for 10 min.
5. The supernatant was discarded, the cells were resuspended with 5 ml of precooled buffer, and resuspension buffer was added again after homogenization to a final volume of 50 ml.
6. Ice bath for 45 min.
7. 4° C., centrifugation at 4000 rpm for 10 min, the bacteria were resuspended with 5 ml ice precooled storage buffer.
8. 100 μl of broth was loaded to each EP tube and frozen at −80° C. or in liquid nitrogen.

Resuspension buffer: $CaCl_2$ (100 mM), $MgCl_2$ (70 mM), NaAc (40 mM)

Storage buffer: 0.5 mL DMSO, 1.9 mL 80% glycol, 1 mL 10×$CaCl_2$) (1 M), 1 mL 10×$MgCl_2$ (700 mM), 1 mL 10×NaAc (400 mM), 4.6 mL ddH2O Transformation of Component Cells:

1. Take 100 μl competent cells were taken and thawed on an ice bath.
2. The appropriate volume of ligation product was added, mixed by gently pipetting, and incubated in ice bath for 30 min. The volume of ligation product normally added was less than 1/10 of the volume of competent cells.
3. The broth was put into a 42° C. water bath for heat shock for 90 s and quickly transferred to an ice bath for 5 min.
4. 500 μl LB was added and incubated at 200 rpm on a constant temperature shaker at 37° C. for 1 hour.
5. The broth was centrifuged at 4000 rpm for 3 min and 200 μl supernatant was added to mix the bacteria well and spread evenly on the surface of the agar plate containing appropriate antibiotics, and the plate is inverted in a 37° C. incubator overnight.

II.6 Expression, Purification, and Fluorescent Detection of Proteins

1. The pET28a based arginine sensor plasmid was transformed into JM109 (DE3), incubated inverted overnight, and the clones were picked from the plates into 250 ml Erlenmeyer flasks, placed in a shaker at 37° C. and incubated at 220 rpm to OD=0.4-0.8, then 1/1000 (V/V) of IPTG (1 M) was added to induce expression at 18° C. for 24-36 h.
2. Upon completion of inducible expression, cells were harvested by centrifugation at 4000 rpm for 30 min, resuspended in 50 mM phosphate buffer and disrupted ultrasonically until the broth were clear, centrifuged at 9600 rpm at 4° C. for 20 min.
3. The centrifuged supernatant was used to obtain protein by purification through a self packed nickel column affinity chromatography column, and the protein obtained after nickel column affinity chromatography was further used to obtain protein dissolved in 20 mM MOPS buffer (pH 7.4) or phosphate buffer PBS.
4. After purified arginine-binding protein muteins were subjected to SDS-PAGE, sensors were diluted to a protein solution having a final concentration of 5-10 μM using assay buffer (100 mm HEPES, 100 mM NaCl, pH 7.3) or phosphate buffer PBS. Arginine was formulated as a stock solution at a final concentration of 1 M with assay buffer (20 mM MOPS, pH 7.4) or phosphate buffer PBS.
5. 100 μl 5 μM of protein solution was taken, incubated at 37° C. for 5 min, arginine was added to mix to a final concentration of 100 mM, respectively, the optical absorption of the protein at 340 nm was determined using a multifunctional fluorescence microplate reader.
6. 100 μl 1 μM of fluorescent sensor solution was taken, incubated at 37° C. for 5 min, arginine was added for titration, and the fluorescence intensity of 528 nm emission after 485 nm fluorescence excitation of the protein was measured. The fluorescence excitation and emission determination of the samples were done using a multifunctional fluorescence microplate reader.
7. 100 μl 1 μM of fluorescent sensor solution was taken, incubated at 37° C. for 5 min, and arginine was added to determine the absorption and fluorescence spectra of the sensor proteins. Determination of the absorption and fluorescence spectra of the samples was done by spectrophotometer and spectrofluorometer.

II.6 Expression, Purification, and Fluorescent Detection of Proteins

1. PAAV-based arginine optical sensor plasmids were transfected into HeLa by using the transfection reagent Lipofectamine2000 (Invitrogen) and incubated in a cell incubator at 37° C. with 5% CO2. After the exogenous gene was fully expressed for 24~36 hours, the fluorescence detection was performed.
2. After induction of expression, adherent HeLa cells were washed three times with PBS and placed in HBSS solution for fluorescence microscopy and microplate reader assays, respectively.

Example 1. Arginine Binding Protein Plasmid

The STM4351 gene in the *Agrobacterium tumefaciens* gene was amplified by PCR and digested with BamHI and EcoRI after gel electrophoresis of the PCR products, while the same double digestion of the pET28a vector was performed. After ligation with T4 DNA ligase, the ligation product was transformed into Trans5a, and the transformed Trans5a was spread on LB plates (kanamycin 100 ug/mL) and incubated at 37° C. overnight. After growing Trans5a transformants were subjected to plasmid extraction, they were subjected to PCR. Positive plasmids were sequenced to be correct for subsequent plasmid construction.

Example 2: Expression and Detection of Optical Sensors with cpYFP Inserted at Different Sites In this example, based on pET28a-STM4351, the insertion of cpYFP at the following sites was selected according to the crystal structure of arginine-binding protein to obtain the corresponding plasmids: 103/104, 103/105, 103/106, 103/107, 103/108, 103/109, 103/110, 103/111, 104/105, 104/106, 104/107, 104/108, 104/109, 104/110, 104/111, 105/106, 105/107, 105/108, 105/109, 105/110, 105/111, 106/107, 106/108, 106/109, 106/110, 106/111, 107/108, 107/109, 107/110, 107/111, 108/109, 108/110, 108/111, 109/110, 109/111, 110/111, 197/198, 197/199, 197/200, 197/201, 197/202, 197/203, 197/204, 197/205, 197/206, 197/207, 197/208, 197/209, 198/199, 198/200, 198/201, 198/202, 198/203, 198/204, 198/205, 198/206, 198/207, 198/208, 198/209, 199/200, 199/201, 199/202, 199/203, 199/204, 199/205, 199/206, 199/207, 199/208, 199/209, 200/201, 200/202, 200/203, 200/204, 200/205, 200/206, 200/207, 200/208, 200/209, 201/202, 201/203, 201/204, 201/205, 201/206, 201/207, 201/208, 201/209, 202/203, 202/204, 202/205, 202/206, 202/207, 202/208, 202/209, 203/204, 203/205, 203/206, 203/207, 203/208, 203/209, 204/205, 204/206, 204/207, 204/208, 204/209, 205/206, 205/207, 205/208, 205/209, 206/207, 206/208, 206/209, 207/208, 207/209 or 208/209. Sequences of exemplary optical sensors are shown in Table 1.

TABLE 1

Sequences of optical sensors

| Sequences | Insertion site |
|---|---|
| SEQ ID NO: 6 | 104/109 |
| SEQ ID NO: 7 | 104/110 |
| SEQ ID NO: 8 | 104/111 |
| SEQ ID NO: 9 | 105/106 |
| SEQ ID NO: 10 | 105/107 |

TABLE 1-continued

| Sequences of optical sensors | |
|---|---|
| Sequences | Insertion site |
| SEQ ID NO: 11 | 105/110 |
| SEQ ID NO: 12 | 106/108 |
| SEQ ID NO: 13 | 106/109 |
| SEQ ID NO: 14 | 107/109 |
| SEQ ID NO: 15 | 107/111 |
| SEQ ID NO: 16 | 110/111 |
| SEQ ID NO: 17 | 197/199 |
| SEQ ID NO: 18 | 197/203 |
| SEQ ID NO: 19 | 197/204 |
| SEQ ID NO: 20 | 198/202 |
| SEQ ID NO: 21 | 198/203 |
| SEQ ID NO: 22 | 199/200 |
| SEQ ID NO: 23 | 199/201 |
| SEQ ID NO: 24 | 199/202 |
| SEQ ID NO: 25 | 199/204 |
| SEQ ID NO: 26 | 199/205 |
| SEQ ID NO: 27 | 200/203 |
| SEQ ID NO: 28 | 200/204 |
| SEQ ID NO: 29 | 200/205 |
| SEQ ID NO: 30 | 200/206 |
| SEQ ID NO: 31 | 201/202 |
| SEQ ID NO: 32 | 201/203 |
| SEQ ID NO: 33 | 201/204 |
| SEQ ID NO: 34 | 201/205 |
| SEQ ID NO: 35 | 201/206 |
| SEQ ID NO: 36 | 202/205 |
| SEQ ID NO: 37 | 203/206 |
| SEQ ID NO: 38 | 204/205 |
| SEQ ID NO: 39 | 204/206 |

The DNA fragment of cpYFP was generated by PCR, and the DNA fragment was inactivated by phosphorylation at the 5' end, and at the same time, a pET28a-arginine-binding protein linearized vector containing different breaking sites was generated by inverse PCR, the linearized pET28a-STM4351 and the 5'-terminal phosphorylated cp YFP fragment were ligated under the action of PEG4000 and T4 DNA ligase to generate a recombinant plasmid. These plates were placed on the Kodak multifunctional in vivo imaging system, and the clones with yellow fluorescence under the excitation of the FITC channel were picked and sequenced by Beijing Liuhe Huada Gene Technology Co., Ltd. Shanghai Branch.

After being sequenced correctly, the recombinant plasmid was transformed into JM109 (DE3) to induce expression, and the protein was purified, and the size was around 55 Kda by SDS-PAGE. This size corresponds to the size of the STM4351-cpYFP fusion protein containing His-tag purified label expressed from pET28a-STM4351-cpYFP. The results are shown in FIG. 1.

Figure 2:
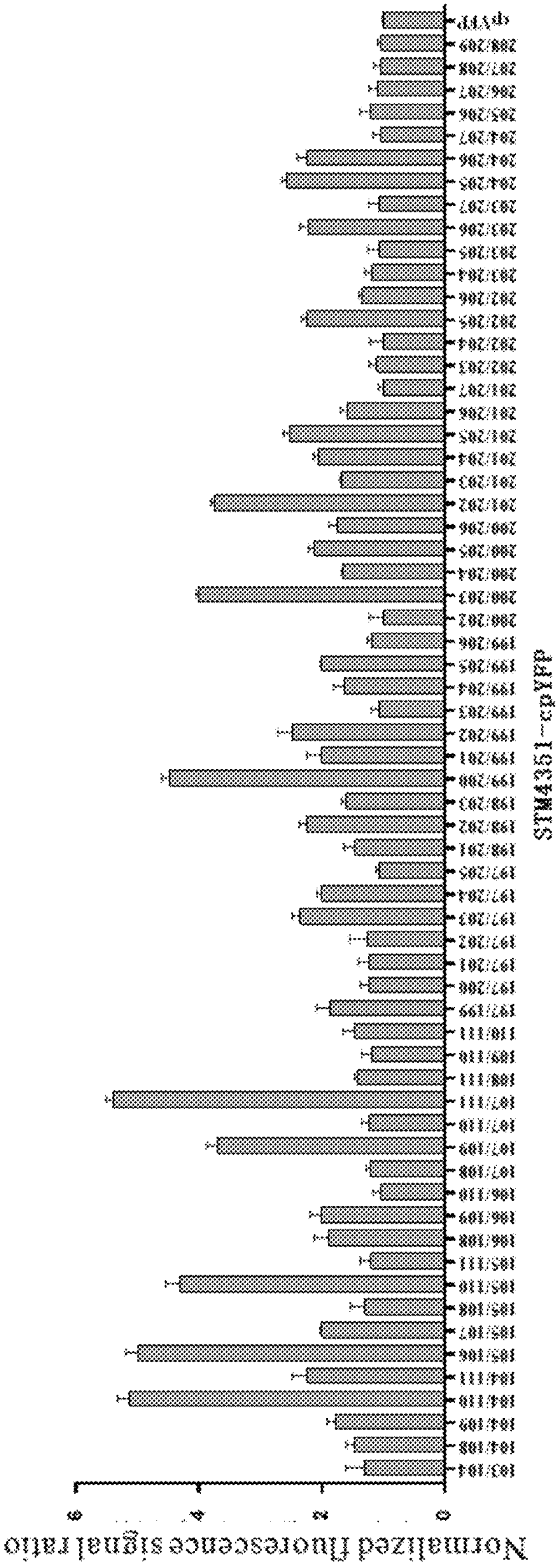
FIG. 2 is a graph showing the response changes of arginine fluorescent sensors to arginine, the sensors are formed by the yellow fluorescent protein cpYFP inserted at different sites of arginine-binding proteins to arginine.

The purified STM4351-cpYFP fusion protein was screened for arginine response, and the detection signal of the fusion fluorescent protein containing 100 mM arginine was divided by the detection signal of the fusion fluorescent protein without arginine. The results are shown in FIG. 2, and the detection results showed that optical sensors that responded more than 2-fold to arginine than control had insertion sites of 104/110, 105/106, 105/109, 105/110, 105/111, 106/108, 106/109, 107/109, 107/111, 197/203, 198/201, 199/200, 199/202, 199/203, 199/204, 200/202, 200/203, 200/204, 200/205, 200/206, 201/202, 201/205, 204/205.

Figure 3:
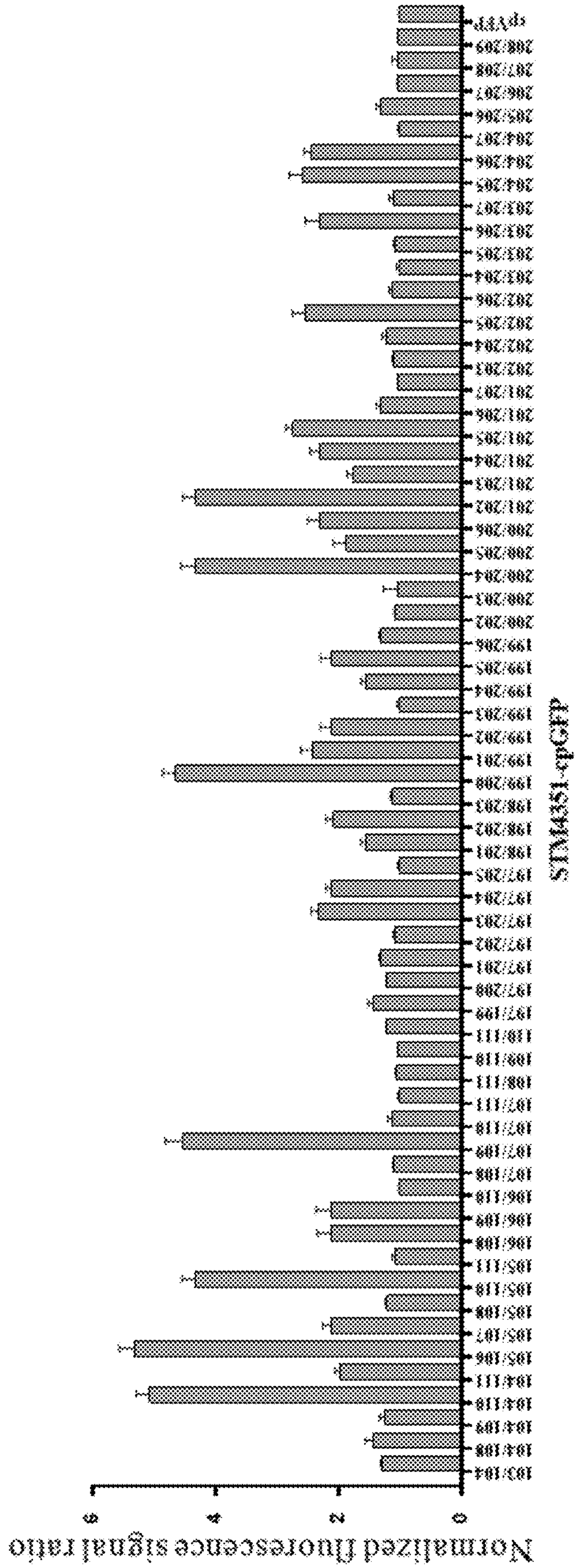
FIG. 3 is a graph showing the response changes of arginine fluorescent sensors to arginine, the sensors are formed by green fluorescent protein cpGFP inserted at different sites of arginine-binding proteins to arginine.

Example 3. Expression and Detection of cpGFP Optical Sensors with Different Insertion Sites According to the method in Example 1, cpYFP was replaced with green fluorescent protein cpGFP, and it was fused to arginine-binding protein to construct an arginine-green fluorescent protein fluorescent sensor, which was expressed and detected according to the method in Example 2. The fluorescence detection results are shown in FIG. 3, and the detection results showed that optical sensors that responded more than 2-fold to arginine than control had insertion sites of 104/110, 105/106, 105/109, 105/110, 105/111, 106/108, 106/109, 107/109, 107/111, 197/203, 198/201, 199/200, 199/202, 199/203, 199/204, 200/202, 200/203, 200/204, 200/205, 200/206, 201/202, 201/205, 204/205.

Figure 4:
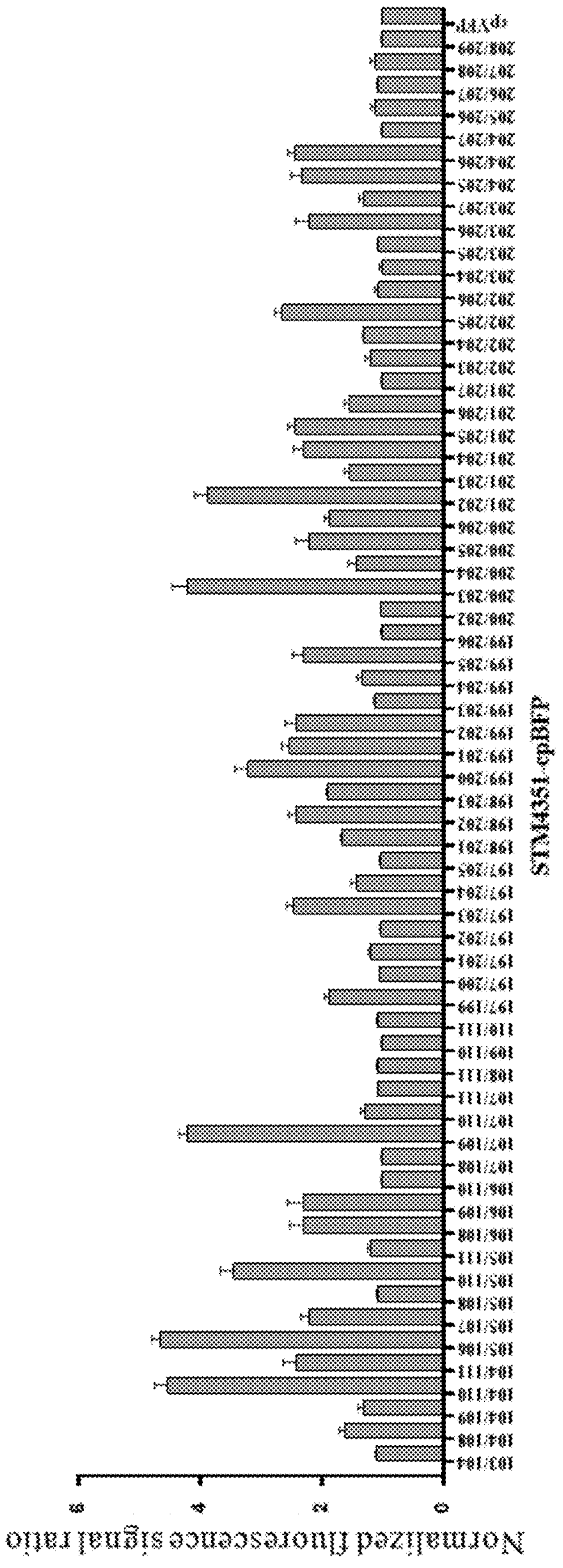
FIG. 4 is a graph showing the response changes of arginine fluorescent sensors to arginine, the sensors are formed by the blue fluorescent protein cpBFP inserted at different sites of arginine-binding proteins to arginine.

Example 4. Expression and Detection of Optical Sensors Having cpBFP Inserted at Different Sites According to the method in Example 1, cpYFP was replaced with the blue fluorescent protein cpBFP, and it was fused into the arginine-binding protein to construct an arginine blue fluorescent protein fluorescent sensor, which was expressed and detected according to the method in Example 2. The fluorescence detection results are shown in FIG. 4, and the detection results showed that optical sensors that responded more than 2-fold to arginine than control had insertion sites of 104/110, 105/106, 105/109, 105/110, 105/111, 106/108, 106/109, 107/109, 107/111, 197/203, 198/201, 199/200, 199/202, 199/203, 199/204, 200/202, 200/203, 200/204, 200/205, 200/206, 201/202, 201/205, 204/205.

Figure 5:
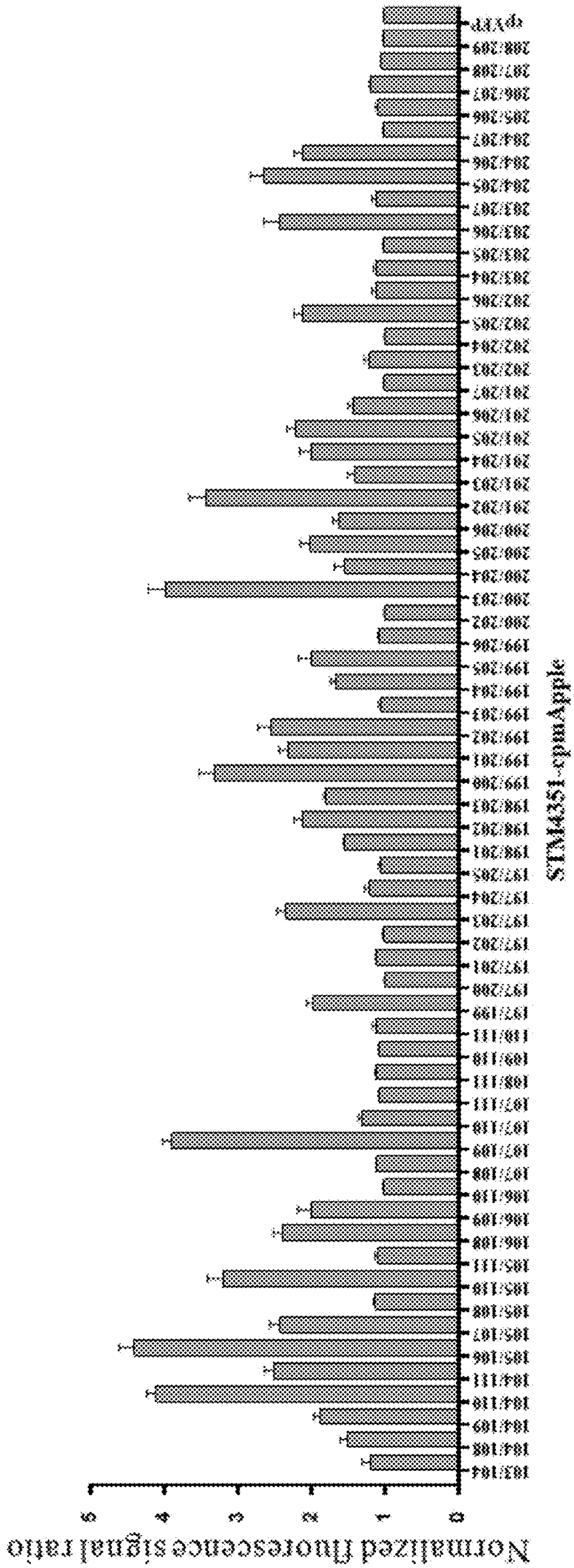
FIG. 5 is a graph showing the response changes of arginine fluorescent sensors to arginine, the sensors are formed by apple red fluorescent protein cpmApple inserted at different sites of arginine-binding proteins.

Example 5. Expression and Detection of Optical Sensors Having cpmApple Inserted at Different Sites According to the method of Example 1, cpYFP was replaced with the apple red fluorescent protein cpmApple, and it was fused into the arginine-binding protein to construct an arginine red fluorescent protein fluorescent sensor, which was expressed and detected according to the method of Example 2. The fluorescence detection results are shown in FIG. 5, and the detection results showed that optical sensors that responded more than 2-fold to arginine than control had insertion sites of 104/110, 105/106, 105/109, 105/110, 105/111, 106/108, 106/109, 107/109, 107/111, 197/203, 198/201, 199/200, 199/202, 199/203, 199/204, 200/202, 200/203, 200/204, 200/205, 200/206, 201/202, 201/205, 204/205.

Example 6: Expression and Detection of Mutated cpYFP Optical Sensors

The plasmid pET28a-STM4351-107/111-cpYFP was linearized by inverse PCR, and the primers contained the base sequence of the desired mutation site, and the obtained PCR product was ligated with phosphorus under the action of PNK, T4 DNA ligase and PEG4000 to obtain S13, R79, D160, the site-directed mutagenesis plasmids of these three sites, were sequenced by Beijing Liuhe BGI Gene Technology Co., Ltd. Shanghai Branch. It was expressed and detected according to the method in Example 2. The amino acid sequences of some mutated optical sensors are shown in SEQ ID NO: 40 (107/111-S13N) and SEQ ID NO: 41 (107/111-D160N); the nucleic acid sequences are shown in SEQ ID NO: 42 (S13N-107/111).

Figure 6:
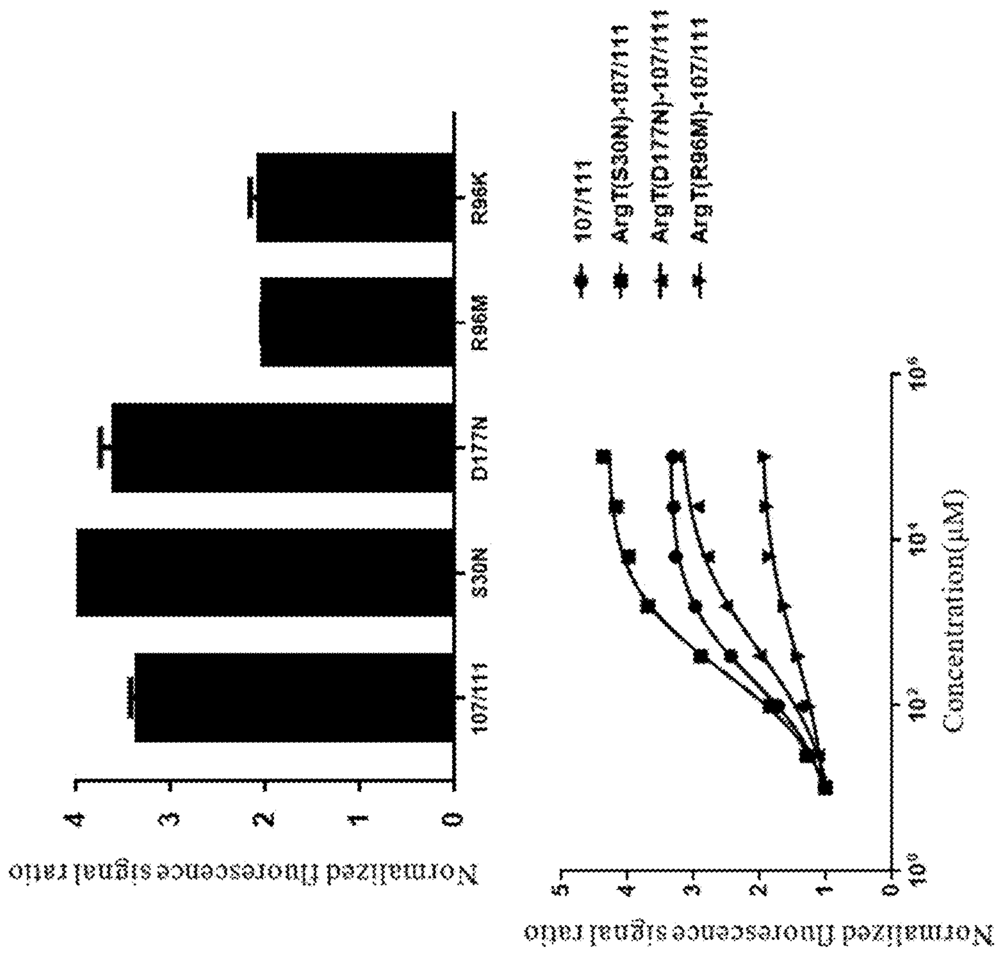
FIG. 6 is a graph showing the response changes of S13, R79 and D160 site mutations to arginine based on the arginine fluorescent sensor formed by the arginine-binding protein 107/111 insertion site of the yellow fluorescent protein cp YFP.

The results are shown in FIG. 6. The fluorescence detection results showed that the S13N-107/111 and D160N-107/111 mutants responded more than 3 times to arginine than control.

Example 7. Titration Curves and Specificity of Sensors

Figure 7A:
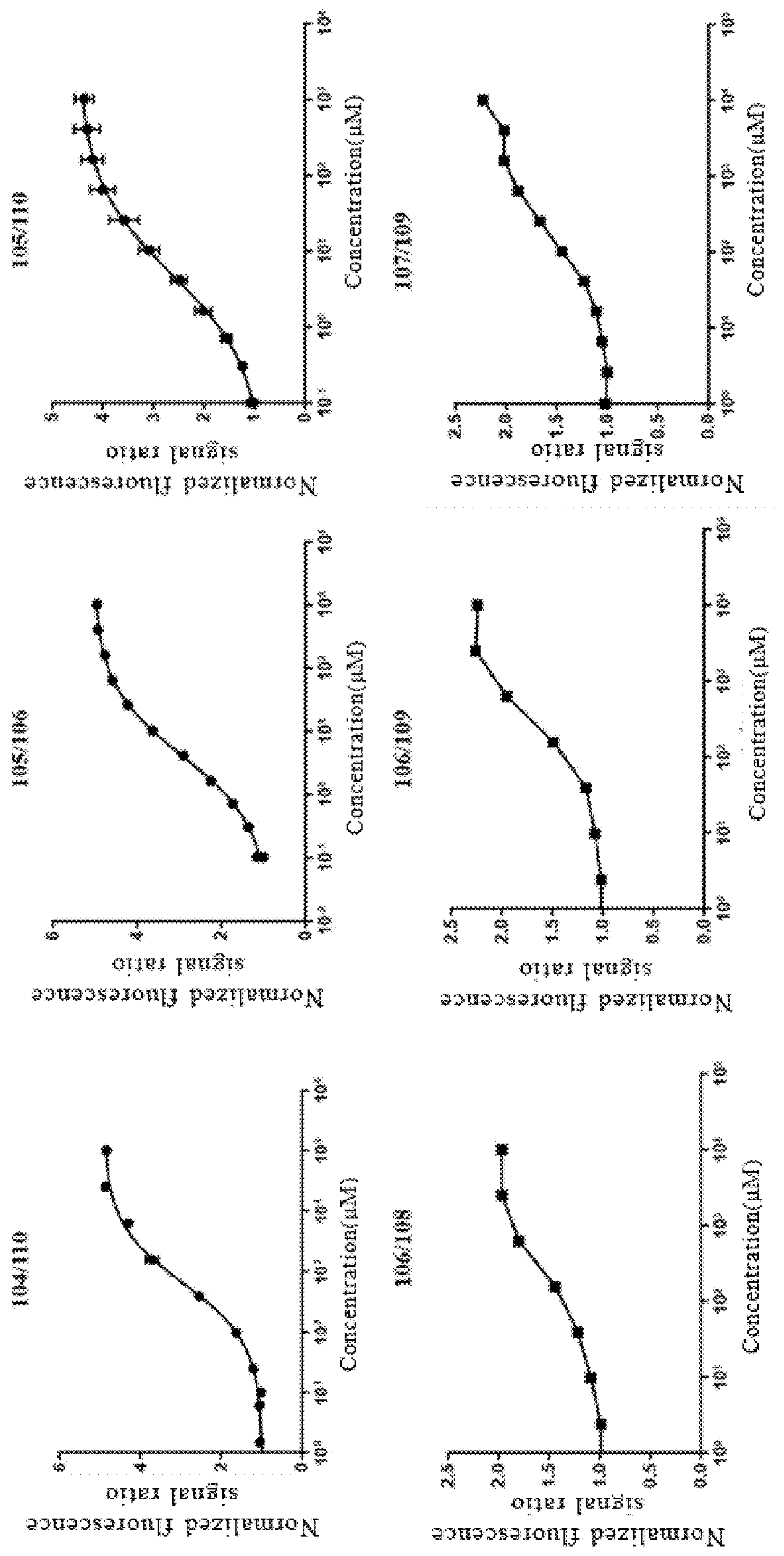
FIG. 7A, 7B, 7C, 7D, and 7E are titration curve to different concentrations of arginine of arginine fluorescent sensors with different insertion sites of 104/110, 105/106, 105/110, 106/108, 106/109, 107/109, 197/199, 197/203, 197/204, 198/201, 198/202, 198/203, 199/200, 199/201, 199/202, 199/205, 200/202, 200/203, 200/204, 200/205, 200/206, 201/202, 201/203, 201/205, 202/205, 203/206, 204/205, 204/206.
Figure 7B:
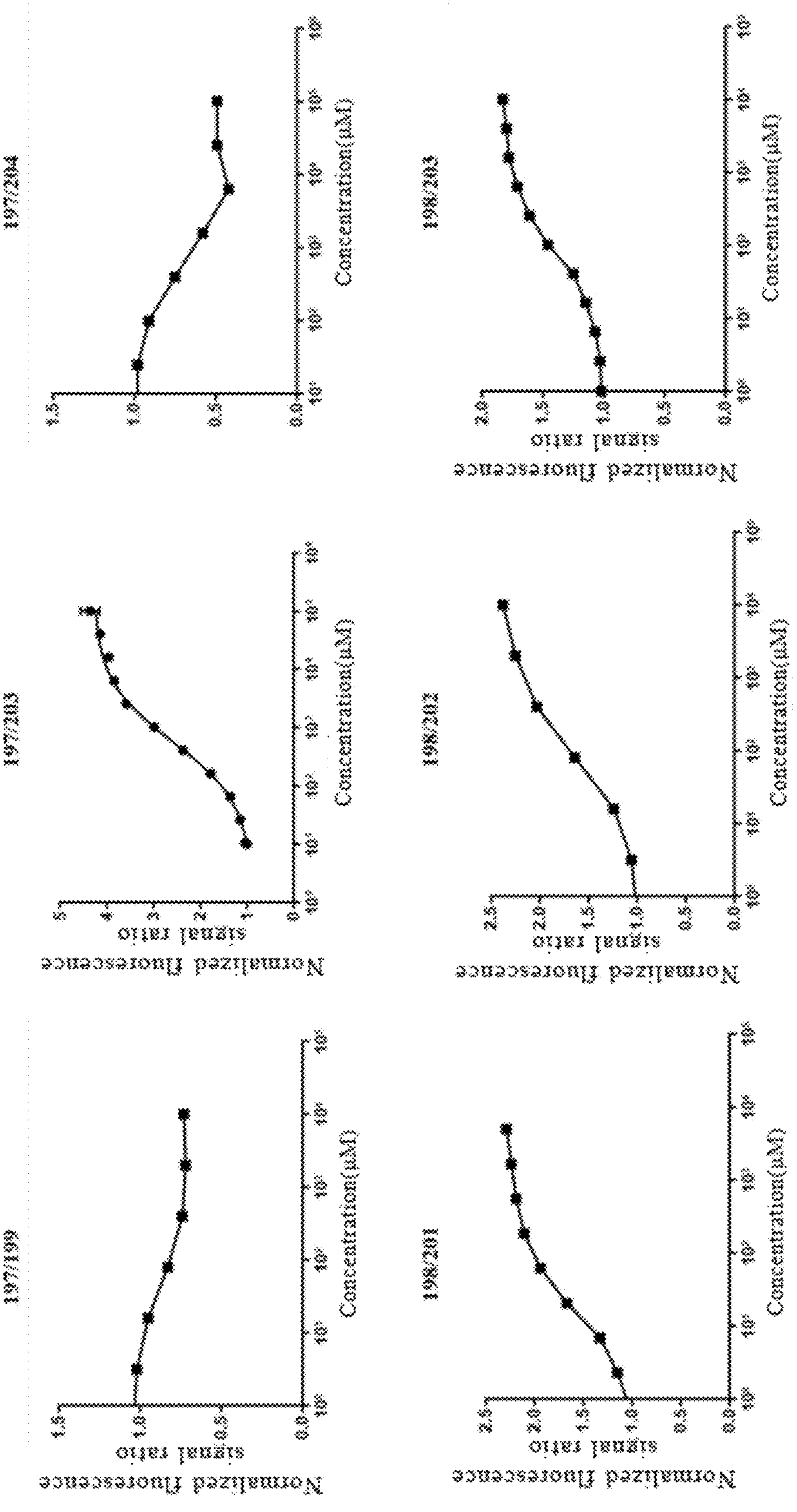
Figure 7C:
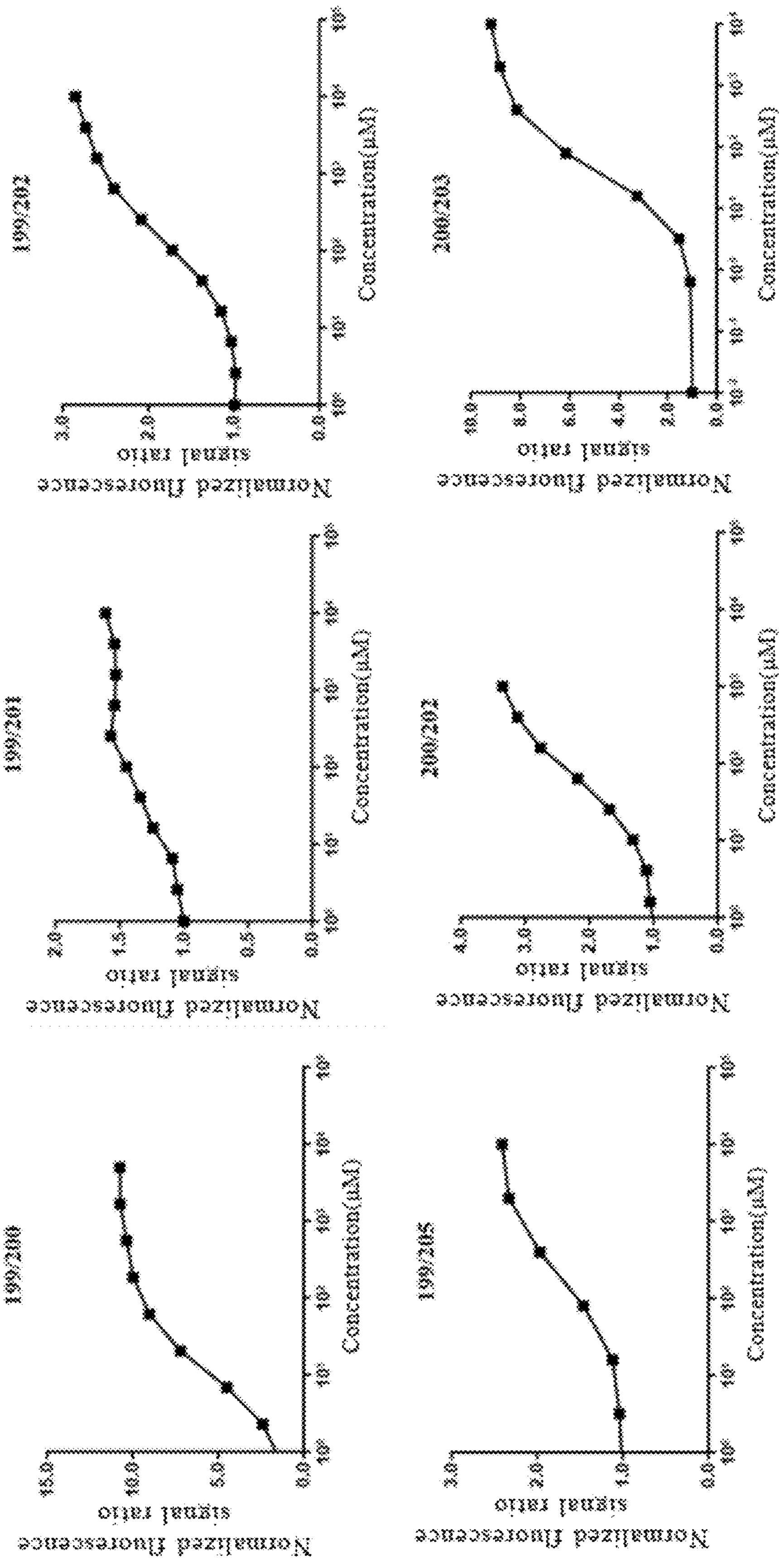
Figure 7D:
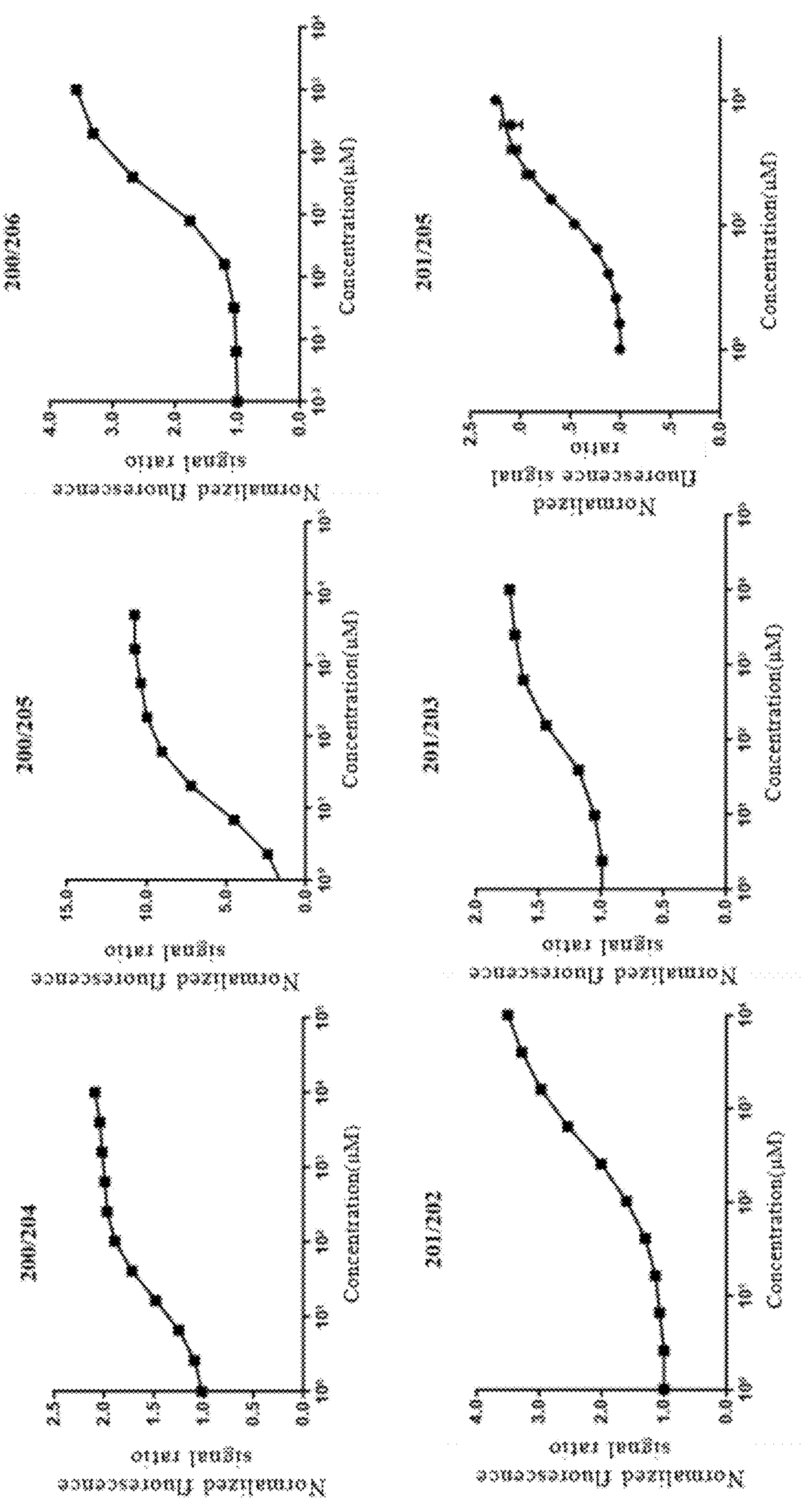
Figure 7E:
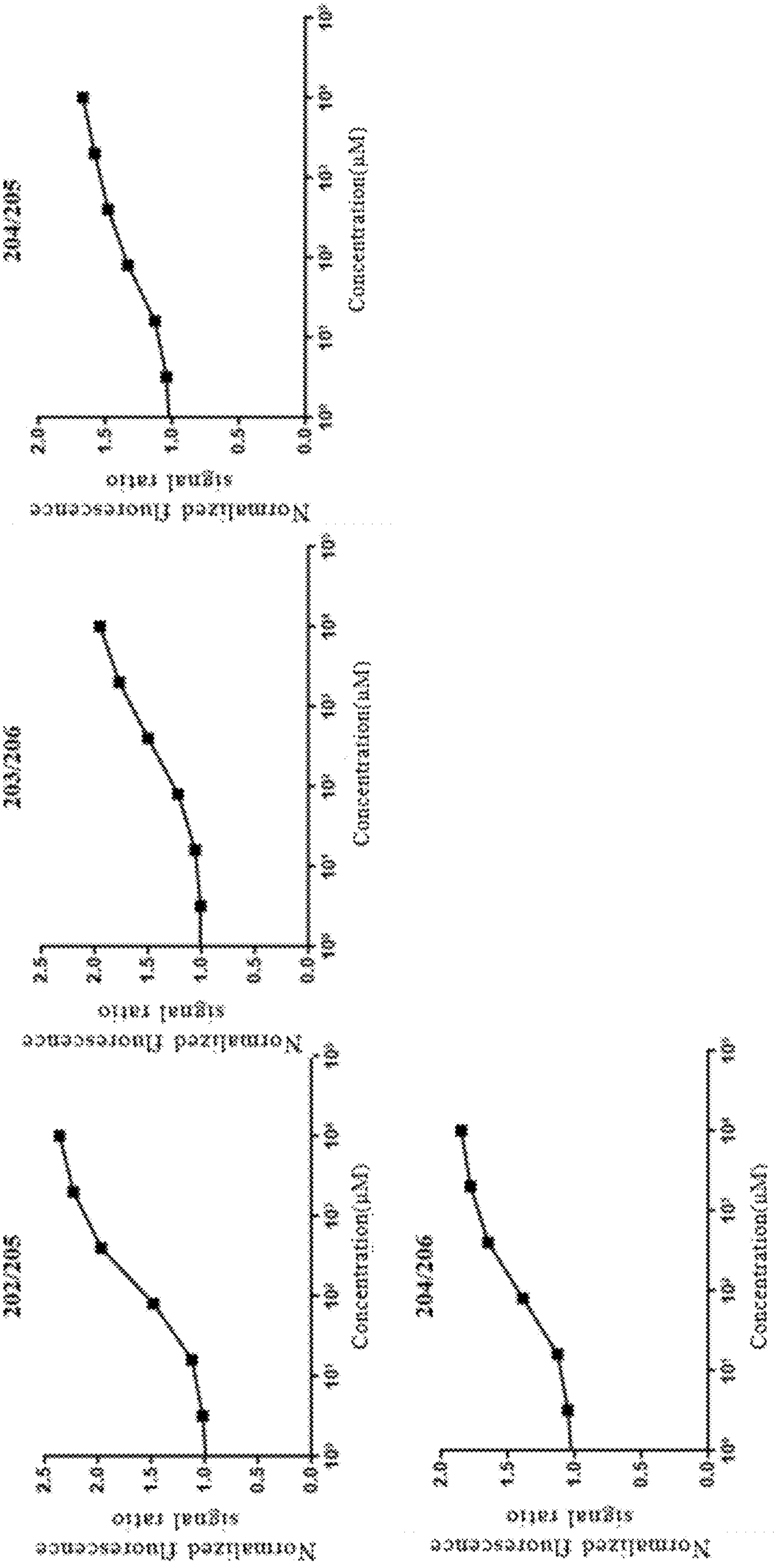
Figure 8:
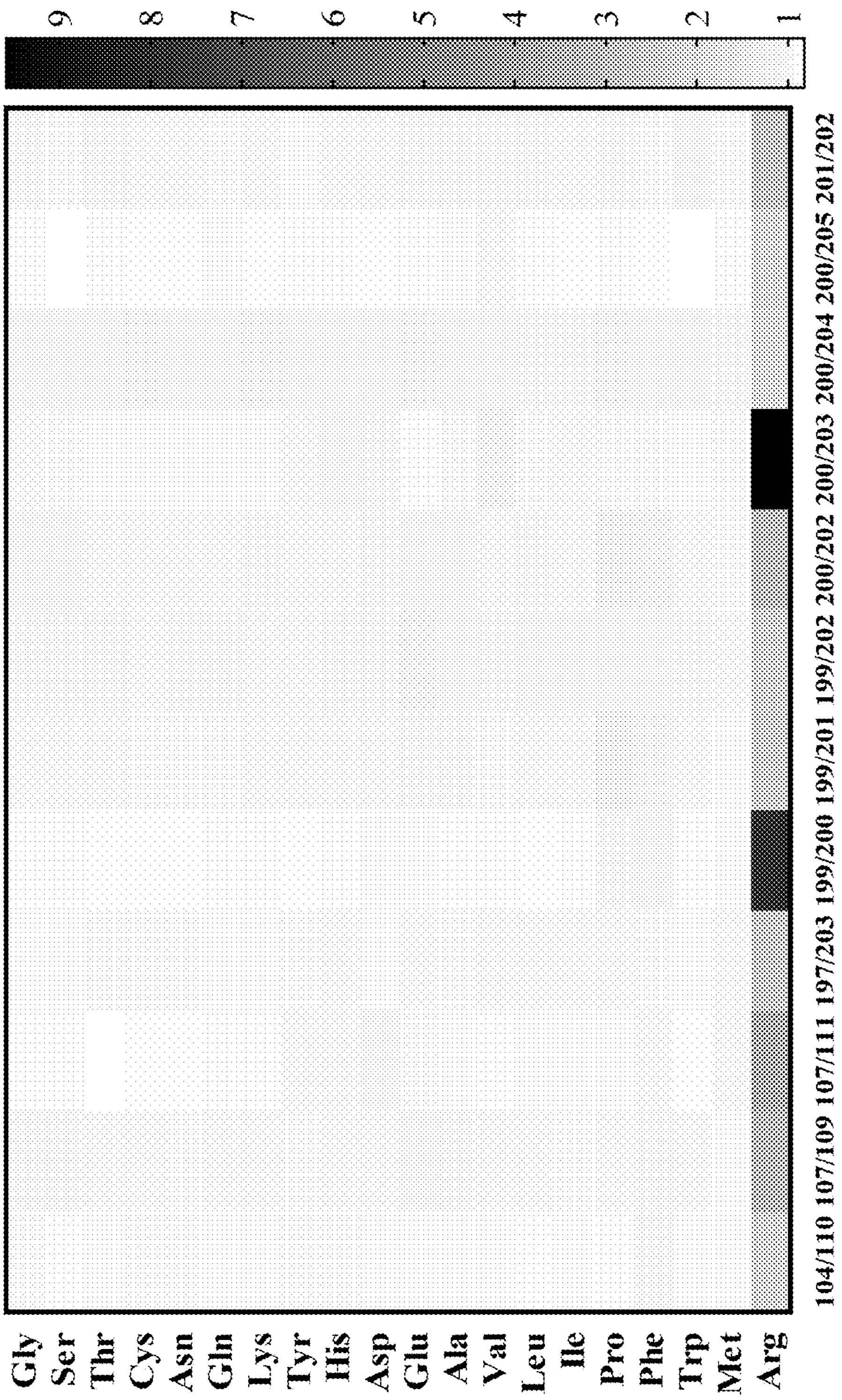
FIG. 8 shows the specific detection of 20 amino acids by arginine fluorescent sensors with different insertion sites of 104/110, 107/109, 107/111, 197/203, 199/200, 199/201, 199/202, 200/202, 200/203, 200/204, 200/205, 201/202.

Twenty-eight STM4351-cpYFP fusion proteins 104/110, 105/106, 105/110, 106/108, 106/109, 107/109, 197/199, 197/203, 197/204, 198/201, 198/202, 198/203, 199/200, 199/201, 199/202, 199/205, 200/202, 200/203, 200/204, 200/205, 200/206, 201/202, 201/203, 201/205, 202/205, 203/206, 204/205, 204/206 were selected to subject to concentration gradient arginine detection, and the variation in the ratio of the fluorescence intensity at 528 nm emission excited at 420 nm and the fluorescence intensity at 528 nm emission excited at 485 nm was detected, the Ka (binding constant) of the arginine sensors at different insertion sites 105/110, 199/200, 200/203 and 200/205 were 5.4 μM, 11.7 μM, 58.5 μM and 15 μM, respectively, and the change amplitudes were 4.3 times, 11.0 times, 8.6 times and 3.0 times, the results are shown in FIG. 7A-B. Specifically detection were performed on sensors with more folds of response having the insertion sites of: 104/110, 107/109, 107/111, 197/203, 199/200, 199/201, 199/202, 200/202, 200/203, 200/204, 200/205 and 201/202, and the results showed that the sensor had good specificity for arginine, as shown in FIG. 8.

Example 8: Spectral Properties of Sensors

Figure 9A:
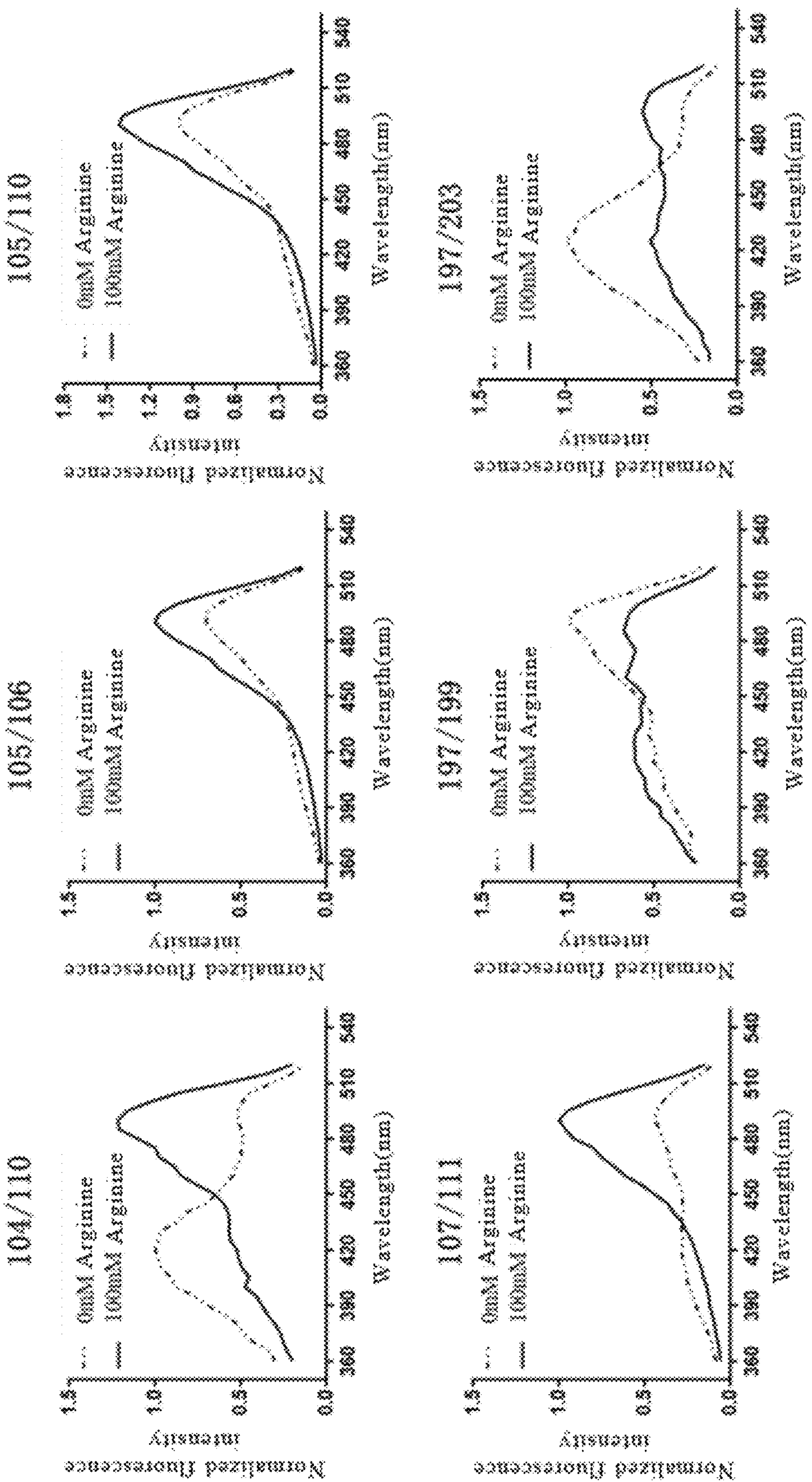
FIG. 9A, 9B, 9C, and 9D are graphs of fluorescence spectral properties of exemplary arginine fluorescent sensors.
Figure 9B:
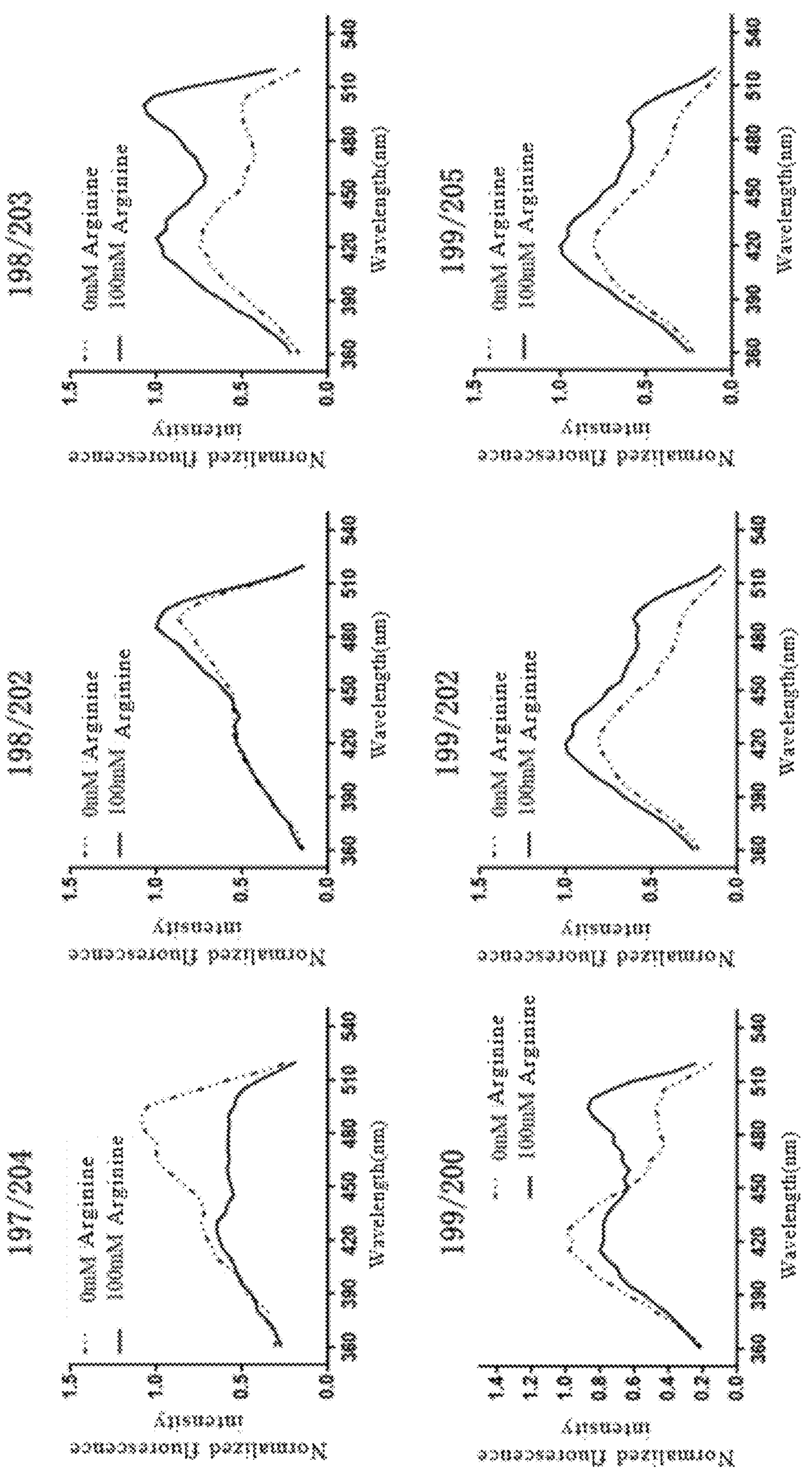
Figure 9C:
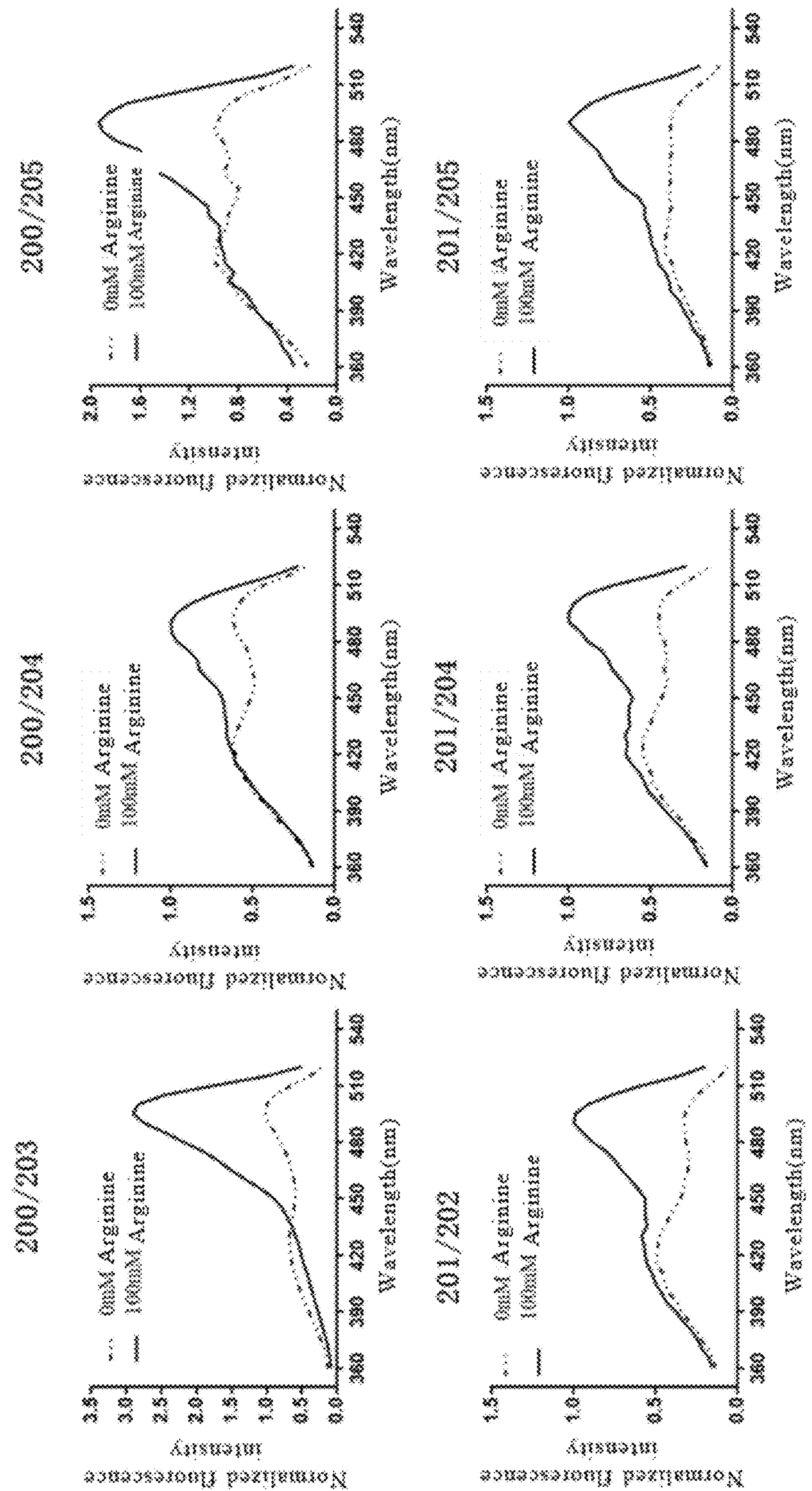
Figure 9D:
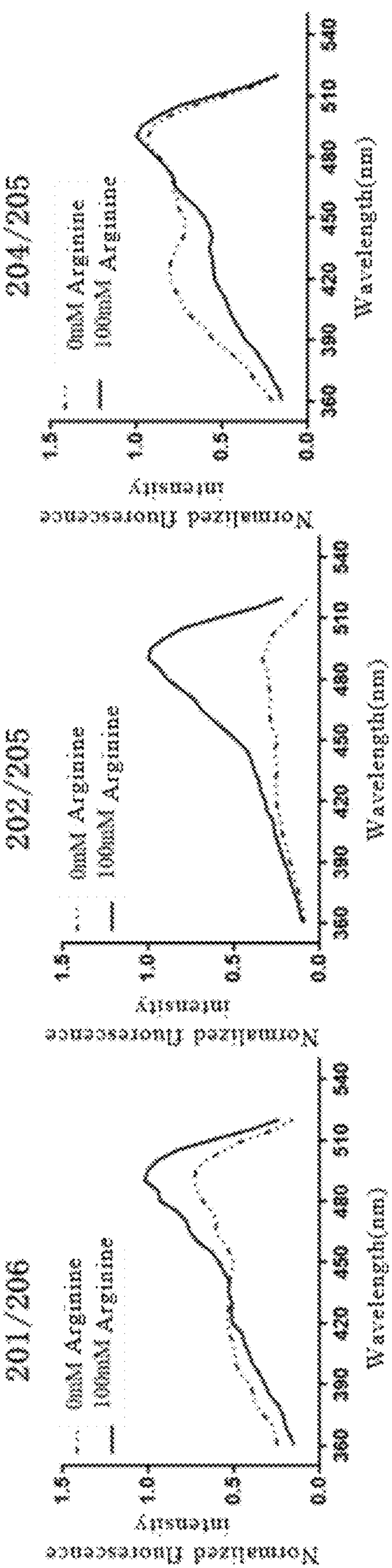

Detection of fluorescence spectra was performed using a fluorescence spectrophotometer after subjecting purified mutant STM4351-199/200-cpYFP (having high response fold and good specificity) to 0 mM and 100 mM arginine treatments for 10 min, respectively. Determination of emission spectra: excitation spectra were recorded with an excitation wavelength of 420 nm and 485 nm and an emission range of 360-540 nm, read every 5 nm. The spectral curve of the arginine fluorescent sensor STM4351-104/110-cpYFP is shown in the first panel of FIG. 9A. After adding 500 mM arginine, the fluorescence intensity of the sensor excited at 420 nm decreased to 1.4 times that of adding 0 mM arginine; and the increase in fluorescence intensity under excitation at 485 nm was 2.0-fold higher than that of adding 0 mM arginine. The 105/106, 105/110, 107/111, 197/199, 197/203, 197/204, 198/202, 198/203, 199/200, 199/202, 199/205, 200/203, 200/204, 200/205, 201/202, 201/204, 201/205, 201/206, 202/205 and 204/205 sensors were treated the same under the same conditions, and their spectral curves are shown in FIG. 9A-B.

Example 9, Subcellular Organelle Localization of Sensors and Performance within Subcellular Organelles In this example, different localization signal peptides were used to fuse to the C-terminus or N-terminus of the arginine fluorescent sensor STM4351-199/200-cp YFP, and the arginine fluorescent sensor STM4351-199/200-cpYFP was localized to different organelles.

Figure 10:
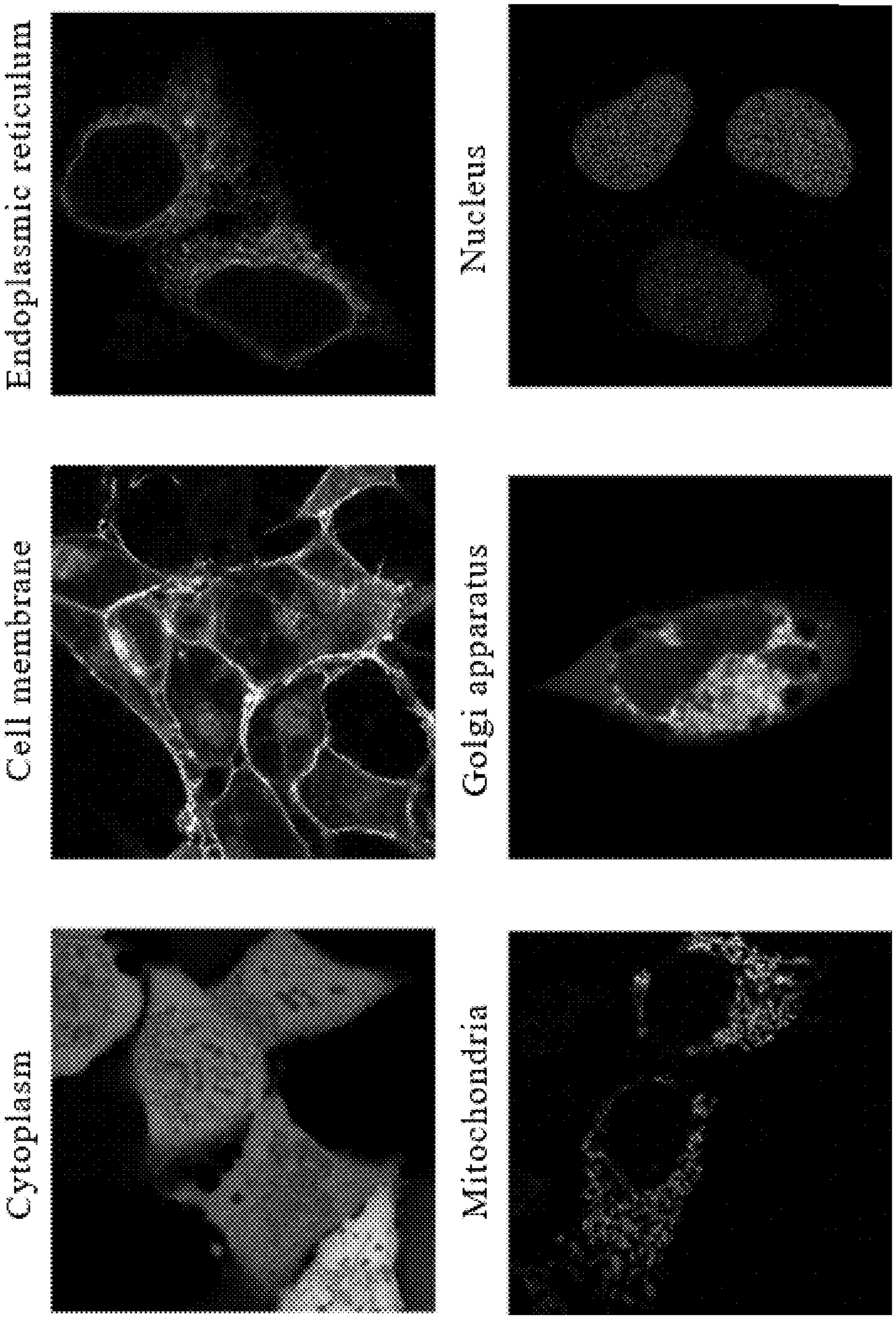
FIG. 10 is localization analysis of exemplary arginine fluorescent sensor in subcellular organs of mammalian cells.

HeLa cells were transfected for 36 hours with arginine fluorescent sensor STM4351-199/200-cpYFP gene plasmids fused with different localization signal peptides. After washing with PBS, the cells were placed in HBSS solution for fluorescence detection under the FITC channel using an inverted fluorescence microscope. We found that the arginine fluorescent sensor FLIPpro can localize to subcellular organelles including cytoplasm, mitochondria, nucleus, Golgi apparatus, endoplasmic reticulum and cell membrane by fusing with different specific localization signal peptides. The results are shown in FIG. 10. Fluorescence was present in different subcellular structures, and the distribution and intensity of fluorescence varied.

Figure 11:
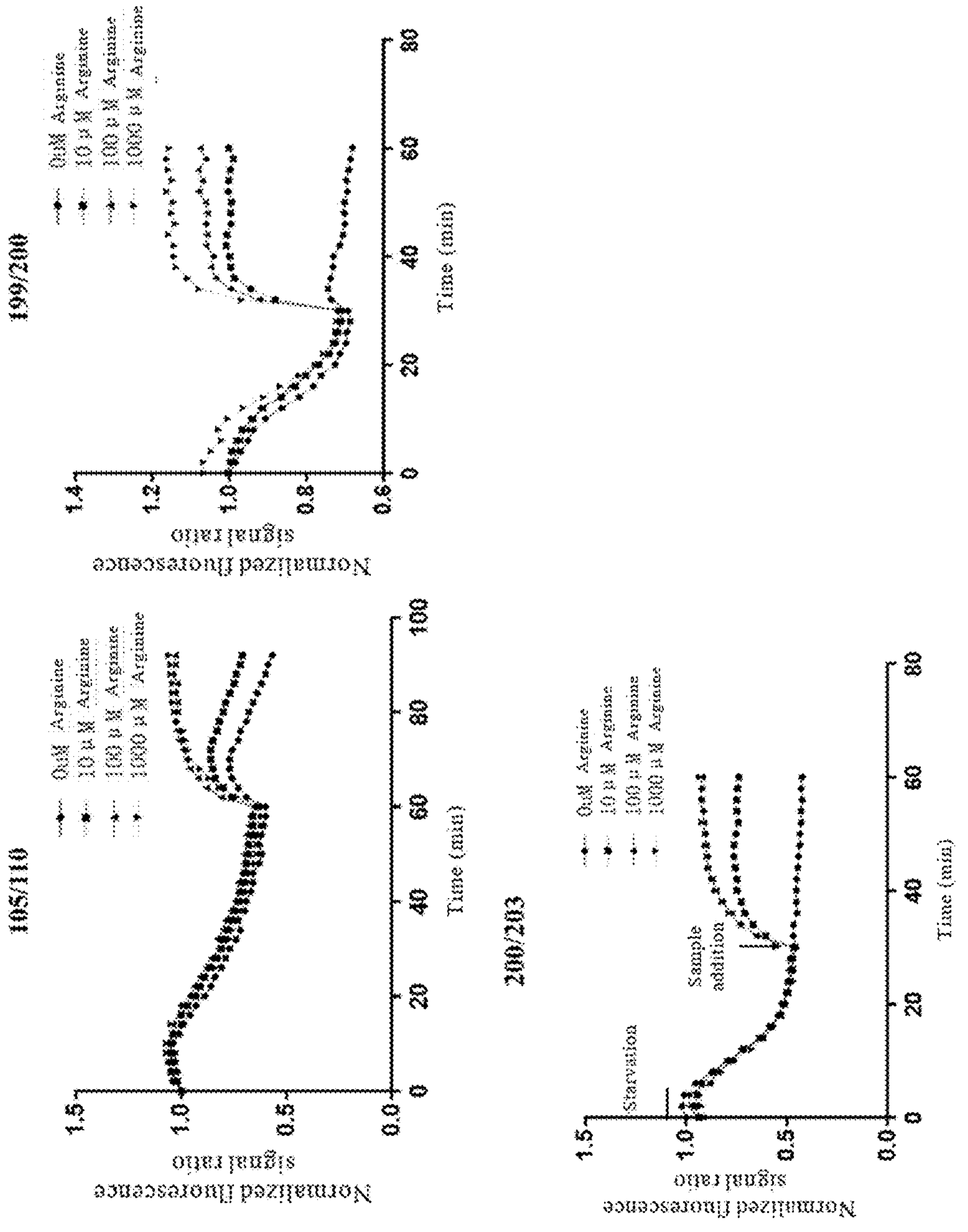
FIG. 11 is dynamic monitoring of arginine transmembrane transport in mammalian cells by the arginine fluorescent sensor.

Example 10: Dynamic Monitoring of Arginine Transmembrane Transport 36 hours after transfection of HeLa cells with plasmids encoding cytosolically expressed optical sensor STM4351-199/200-cpYFP, cells were rinsed using PBS, placed in HBSS solution, and then changes in the ratio of the fluorescence intensity at 528 nm emission excited at 420 nm to that at 528 nm emission excited at 485 nm were detected over 40 min. The results are shown in FIG. 11. After 2 hours of starvation, the ratio 485/420 increased gradually after adding 10 mM arginine for 20 minutes, and the highest ratio was 2.2 times. Same as STM4351-105/110-cpYFP sensor and STM4351-200/203-cpYFP sensor.

Example 11: Sensor-Based High-Throughput Compound Screening in Living Cells

In this example, we used HeLa cells with cytosolic expression of the arginine sensor STM4351-199/200-cpYFP for high-throughput compound screening.

Figure 12:
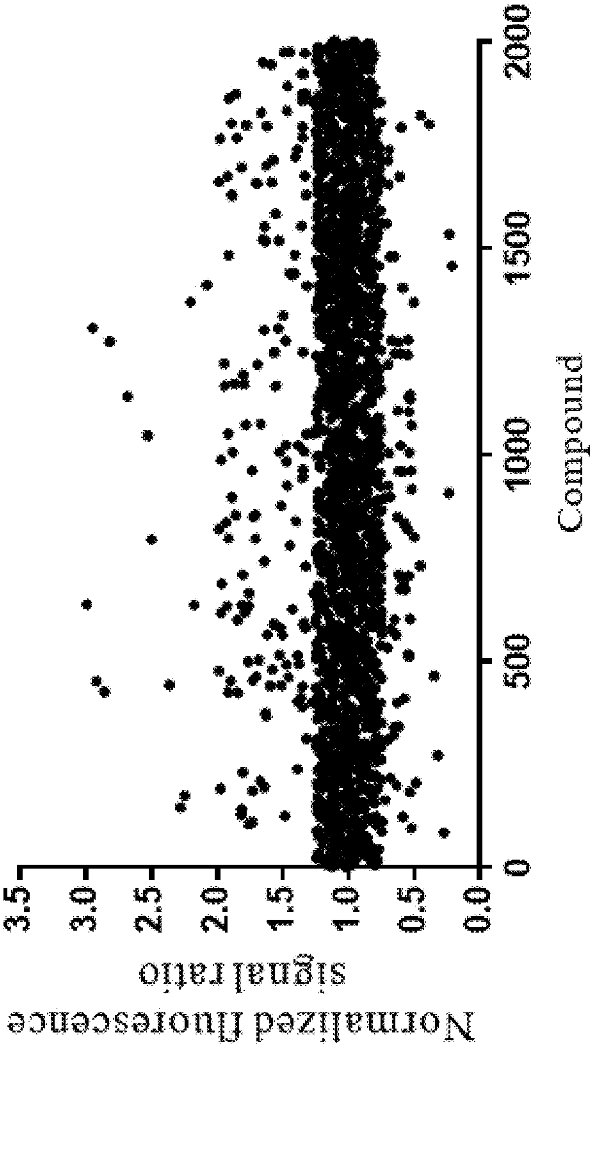
FIG. 12 is a graph of the high-throughput compound screening analysis in living cells based on arginine fluorescent sensors as described in Example 11.

HeLa cells transfected with the STM4351-199/200-cpYFP gene were rinsed using PBS, placed in HBSS solution (without arginine) for 1 hour, and treated with 10 μM of compound for 1 hour. Lactate was added in each sample. Changes in the ratio of fluorescence intensity at 528 nm emission excited at 420 nm to that of 528 nm emission excited at 485 nm were recorded using a microplate reader. Samples not treated with any compound were used as controls for normalization. The results are shown in FIG. 12. Of the 2000 compounds used, the vast majority had minimal effects on arginine's entry into cells. Sixteen compounds were able to increase the cellular uptake of arginine, and other 11 compounds were able to decrease the cellular uptake of arginine significantly.

Example 12: Quantitative Detection of Arginine in Blood by Sensor

In this example, arginine was analyzed in mouse and human blood supernatants using purified arginine fluorescent sensor STM4351-199/200-cpYFP.

Figure 13:
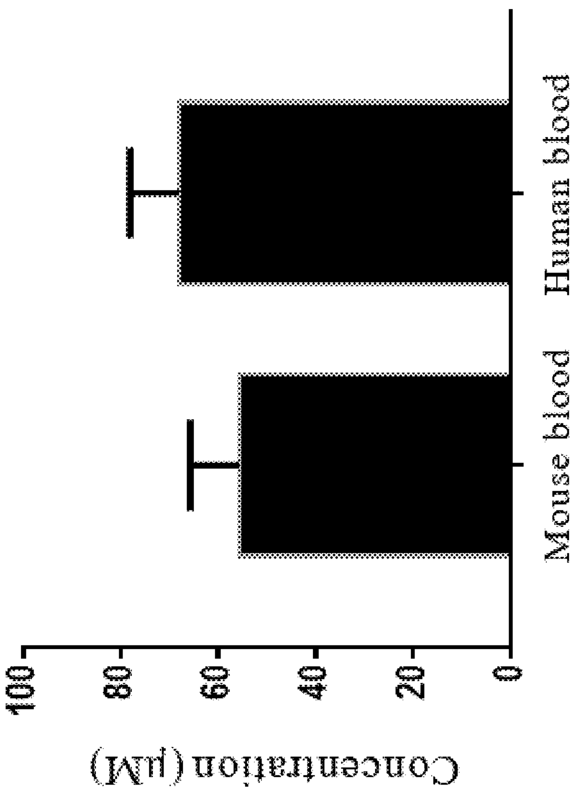
FIG. 13 is a graph showing the quantitative analysis of arginine in mouse and human blood by the arginine fluorescent sensor as described in Example 12.

After 10 min of treatment by mixing arginine fluorescent probesensor STM4351-199/200-cpYFP with diluted blood supernatants, the ratio of fluorescence intensity at 528 nm emission excited at 420 nm to that of 528 nm emission excited at 485 nm was measured using a microplate reader. Results were shown in FIG. 13, arginine levels were around 56 μM in mouse blood and around 68 μM in human blood.

It can be seen from the above examples that the arginine fluorescent sensor provided by the present invention has relatively small protein molecular weight and was prone to maturation, had large dynamic change in fluorescence, good specificity, and ability to be expressed in cells by gene manipulation methods, which could locate, quantitatively detect arginine in real time inside and outside cells; and enables high-throughput compound screening.

The above are only the preferred embodiments of the present invention. It should be pointed out that for those skilled in the art, without departing from the principles of the present invention, several improvements and modifications can be made, which should be regarded as the protection scope of the present invention.

We claim:

1. An optical sensor comprising an arginine-sensitive polypeptide and an optically active polypeptide, wherein the arginine-sensitive polypeptide has the sequence shown by SEQ ID NO: 1 or a sequence having at least 80% sequence identity with SEQ ID NO: 1 and having tryptophan binding function, the optically active polypeptide is a fluorescent protein, the optically active polypeptide is located at one or more sites of the arginine-sensitive polypeptide selected from the group consisting of: 104/110, 104/111, 105/106, 105/110, 106/109, 107/109, 107/111, 197/203, 197/204, 198/202, 199/200, 199/202, 200/203, 200/205, 201/202, 201/205, 202/205, 203/206, 204/205, and 204/206.

2. The optical sensor of claim 1 wherein the arginine-sensitive polypeptide comprises mutations at a position selected from the group consisting of: S13, R79 and D160.

3. The optical sensor of claim 2, wherein the mutations are selected from the group consisting of: S30N, D177N, R96M, R96K.

4. The optical sensor of claim 2, wherein the mutations are S13N, and/or D160N.

5. The optical sensor according to claim 1, wherein the fluorescent protein is selected from the group consisting of: yellow fluorescent protein, orange fluorescent protein, red fluorescent protein, green fluorescent protein, blue fluorescent protein, and apple red fluorescent protein.

6. The optical sensor according to claim 1, wherein the fluorescent protein has a sequence as shown by any of SEQ ID Nos: 2-5 or a sequence having at least 80% sequence identity with SEQ ID NO: 2-5.

7. A nucleic acid sequence selected from the group consisting of:
- a polynucleotide encoding the optical sensor according to claim 1;
- a fragment thereof; and
- a complement sequence of said polynucleotide or fragment thereof.

8. A nucleic acid construct comprising any of the nucleic acid sequences according to claim 7.

9. A host cell, wherein the host cell
- expresses the optical sensor according to claim 1;
- comprises a nucleic acid sequence encoding said optical sensor of; or
- comprises a nucleic acid construct comprising said nucleic acid sequence of.

10. A method for producing the optical sensor according to claim 1, comprising culturing a host cell, and separating said optical sensor from the culture, wherein the host cell:
- expresses the optical sensor according to claim 1;
- comprises a nucleic acid sequence encoding said optical sensor; or
- comprises a nucleic acid construct comprising said nucleic acid sequence of.

11. A detection kit comprising:
- the optical sensor according to claim 1;
- a nucleic acid sequence encoding said optical sensor of;
- nucleic acid construct comprising said nucleic acid sequence of; or
- a cell expressing said optical sensor; and
- additional reagents required for arginine detection by the optical sensor.

12. The nucleic acid construct of claim 8, wherein the nucleic acid construct is an expression vector.

13. A method for detecting arginine in a sample, comprising contacting the sample with an optical sensor according to claim 1, and detecting changes in an optically active polypeptide.

14. The method according to claim 13, wherein the sample is blood.

15. The method according to claim 13, wherein the detecting is performed in vivo, in vitro, subcellularly, or in situ.

16. A method for screening compounds, comprising contacting a candidate compound with an optical sensor according to claim 1, detecting changes in the optically active polypeptide, and screening the compounds according to the changes in the optically active polypeptide.

17. The method according to claim 16, wherein the candidate compound is a pharmaceutical.

* * * * *